United States Patent
Whalen et al.

(10) Patent No.: US 12,138,501 B1
(45) Date of Patent: Nov. 12, 2024

(54) UNWEIGHTING EXERCISE EQUIPMENT

(71) Applicants: Boost Treadmills, LLC, Palo Alto, CA (US); Robert Tremaine Whalen, Los Altos, CA (US)

(72) Inventors: Sean Tremaine Whalen, Los Altos, CA (US); Thomas Jack Waldo Allen, Palo Alto, CA (US); Robert Tremaine Whalen, Los Altos, CA (US)

(73) Assignee: Boost Treadmills, LLC, Palo Alto, CA (US)

( * ) Notice: Subject to any disclaimer, the term of this patent is extended or adjusted under 35 U.S.C. 154(b) by 8 days.

(21) Appl. No.: 18/244,793

(22) Filed: Sep. 11, 2023

Related U.S. Application Data

(63) Continuation of application No. 17/980,782, filed on Nov. 4, 2022, now Pat. No. 11,794,051, which is a
(Continued)

(51) Int. Cl.
*A63B 21/00* (2006.01)
*A61F 7/02* (2006.01)
(Continued)

(52) U.S. Cl.
CPC ...... *A63B 21/00181* (2013.01); *A61G 10/023* (2013.01); *A61F 2007/0239* (2013.01);
(Continued)

(58) Field of Classification Search
CPC .............. A63B 21/00181; A63B 22/02; A63B 69/0064; A63B 2208/053;
(Continued)

(56) References Cited

U.S. PATENT DOCUMENTS

| 44,198 A | 9/1864 | Jones |
| 54,530 A | 5/1866 | Hadfield |

(Continued)

FOREIGN PATENT DOCUMENTS

| CA | 2236774 C | 11/1999 |
| CN | 2034152 U | 3/1989 |

(Continued)

OTHER PUBLICATIONS

Showa Denki Taiwan ,"てらすウォーカー,, 取扱説明書・注意書"("Terasu Walker, Instruction Manual"), May 14, 2015, Taiwan.

(Continued)

*Primary Examiner* — Garrett K Atkinson
(74) *Attorney, Agent, or Firm* — Anthony Kandare; KandareIP, LLC

(57) ABSTRACT

An unweighting system for unweighting a user while using an exercise machine is provided that includes a treadmill exercise device having a treadmill frame and a rotatable belt, an unweighting assembly for applying unweighting force to the user, a system frame, and a substantially airtight chamber. The system frame includes the treadmill frame, frame elements structurally attached to the treadmill frame, and a top surface region adapted for user engagement during exercise having a surface width and a surface length. The top surface region includes a movable running surface defined by the rotatable belt that extends a run length, and a stationary deck extending about at least a portion of the movable running surface. The stationary deck defines a sealing surface having a maximum seal width greater than the belt width and less than the surface width, to which the substantially airtight chamber is attached.

20 Claims, 22 Drawing Sheets

Related U.S. Application Data continuation of application No. 17/351,226, filed on Jun. 18, 2021, now Pat. No. 11,517,781, which is a continuation of application No. 16/016,340, filed on Jun. 22, 2018, now abandoned, which is a continuation-in-part of application No. 29/643,045, filed on Apr. 4, 2018.

(60) Provisional application No. 62/523,363, filed on Jun. 22, 2017.

(51) Int. Cl.
  *A61G 10/02* (2006.01)
  *A63B 22/02* (2006.01)
  *A63B 69/00* (2006.01)

(52) U.S. Cl.
  CPC .............. *A61H 2201/1652* (2013.01); *A61H 2201/5071* (2013.01); *A63B 22/02* (2013.01); *A63B 69/0064* (2013.01); *A63B 2208/053* (2013.01); *A63B 2208/056* (2013.01)

(58) Field of Classification Search
  CPC ............ A63B 2208/056; A61G 10/023; A61F 2007/0239; A61H 2201/1652; A61H 2201/5071
  See application file for complete search history.

(56) References Cited

U.S. PATENT DOCUMENTS

| | | |
|---|---|---|
| 72,631 A | 12/1867 | Hadfield |
| 100,867 A | 3/1870 | Curran |
| 871,074 A | 11/1907 | Stockton |
| 1,152,014 A | 8/1915 | Farkell |
| 1,182,018 A * | 5/1916 | Koenig ............ A01K 3/00 256/25 |
| 1,336,774 A | 4/1920 | Cooper |
| 1,504,166 A | 8/1924 | Thornley |
| 2,262,019 A | 11/1941 | Lincoln |
| 2,785,004 A | 3/1957 | Cooper |
| 3,165,314 A | 1/1965 | Clearman |
| 3,176,793 A | 4/1965 | Hlacia |
| 3,192,014 A | 6/1965 | Leyshon |
| 3,332,176 A | 7/1967 | Knetzer |
| 3,428,015 A | 2/1969 | Cloud |
| 3,768,467 A | 10/1973 | Jennings |
| 3,911,913 A | 10/1975 | June |
| 4,149,712 A | 4/1979 | Murphy |
| 4,257,407 A | 3/1981 | Macchi |
| 4,343,302 A | 8/1982 | Dillon |
| 4,411,422 A | 10/1983 | Solloway |
| 4,509,513 A | 4/1985 | Lasley |
| 4,536,163 A | 8/1985 | Schnirch et al. |
| 4,576,376 A | 3/1986 | Miller |
| 4,614,337 A | 9/1986 | Schonenberger |
| 4,621,621 A | 11/1986 | Marsalis |
| 4,712,788 A | 12/1987 | Gaudreau, Jr. |
| 4,731,882 A | 3/1988 | Ekman |
| 4,776,581 A | 10/1988 | Shepherdson |
| 4,805,601 A | 2/1989 | Eischen, Sr. |
| 4,887,317 A | 12/1989 | Phillips, Sr. et al. |
| 4,934,694 A | 6/1990 | McIntosh |
| 4,959,047 A | 9/1990 | Tripp, Jr. |
| 4,974,829 A | 12/1990 | Gamow et al. |
| 5,029,579 A | 7/1991 | Trammell |
| 5,075,902 A | 12/1991 | McReynolds et al. |
| 5,109,837 A | 5/1992 | Gamow |
| 5,129,647 A | 7/1992 | Castellanos |
| 5,133,339 A * | 7/1992 | Whalen ............ A63B 21/00181 482/52 |
| 5,221,241 A | 6/1993 | Bare, II |
| 5,242,339 A | 9/1993 | Thornton |
| 5,356,361 A | 10/1994 | Watenpaugh |
| 5,360,001 A | 11/1994 | Brill et al. |
| 5,368,532 A | 11/1994 | Farnet |
| 5,470,293 A | 11/1995 | Schonenberger |
| 5,527,242 A | 6/1996 | Gangloff |
| 5,571,062 A | 11/1996 | Saganovsky |
| 5,577,598 A | 11/1996 | Schoenenberger |
| 5,582,561 A | 12/1996 | Gonzalez |
| 5,623,944 A | 4/1997 | Nashner |
| 5,662,311 A | 9/1997 | Waedekin et al. |
| 5,678,543 A | 10/1997 | Bower |
| 5,700,232 A | 12/1997 | Clausen et al. |
| 5,702,323 A | 12/1997 | Poulton |
| 5,704,881 A | 1/1998 | Dudley |
| 5,706,822 A | 1/1998 | Khavari |
| 5,738,612 A | 4/1998 | Tsuda |
| 5,799,652 A | 9/1998 | Kotliar |
| 5,830,162 A | 11/1998 | Giovannetti |
| 5,919,419 A | 7/1999 | Majuri |
| 5,921,892 A | 7/1999 | Easton |
| 5,960,480 A | 10/1999 | Neustater et al. |
| 6,027,464 A | 2/2000 | Dahlquist |
| 6,033,344 A | 3/2000 | Trulaske et al. |
| 6,042,537 A | 3/2000 | Kaiser |
| 6,146,315 A | 11/2000 | Schonenberger |
| 6,220,992 B1 | 4/2001 | Shafik |
| 6,273,844 B1 | 8/2001 | Kelsey et al. |
| 6,332,290 B1 | 12/2001 | Delamare |
| 6,332,354 B1 | 12/2001 | Lalor et al. |
| 6,348,025 B1 | 2/2002 | Schonenberger |
| 6,405,685 B1 | 6/2002 | Cox |
| 6,482,128 B1 | 11/2002 | Michalow |
| 6,527,678 B1 | 3/2003 | Wang et al. |
| 6,539,946 B2 | 4/2003 | Weyergans |
| 6,554,747 B1 | 4/2003 | Rempe |
| 6,565,624 B2 | 5/2003 | Kutt et al. |
| 6,609,054 B2 | 8/2003 | Wallace |
| 6,645,126 B1 | 11/2003 | Martin et al. |
| 6,656,091 B1 | 12/2003 | Abelbeck et al. |
| 6,666,831 B1 | 12/2003 | Edgerton et al. |
| D495,384 S | 8/2004 | Rolfes |
| 6,783,482 B2 | 8/2004 | Oglesby et al. |
| D497,961 S | 11/2004 | Rolfes |
| 6,821,233 B1 | 11/2004 | Colombo et al. |
| 6,905,459 B2 | 6/2005 | Humphries, Jr. |
| 6,918,858 B2 | 7/2005 | Watterson et al. |
| 7,063,678 B1 | 6/2006 | Cook |
| 7,141,007 B2 | 11/2006 | Egger |
| 7,166,064 B2 | 1/2007 | Watterson et al. |
| 7,494,450 B2 | 2/2009 | Solomon |
| 7,556,040 B2 | 7/2009 | Meyer et al. |
| 7,591,795 B2 | 9/2009 | Whalen |
| 7,594,281 B1 | 9/2009 | Stinson et al. |
| 7,762,930 B2 | 7/2010 | Egger |
| 7,780,587 B2 | 8/2010 | Thornton et al. |
| 7,785,242 B2 | 8/2010 | Solomon |
| 7,837,597 B2 | 11/2010 | Reyes et al. |
| 7,850,629 B2 | 12/2010 | Ravikumar |
| 7,857,731 B2 | 12/2010 | Hickman et al. |
| 7,862,478 B2 | 1/2011 | Watterson et al. |
| 7,914,420 B2 | 3/2011 | Daly et al. |
| 8,235,724 B2 | 8/2012 | Gilley et al. |
| 8,308,618 B2 | 11/2012 | Bayerlein et al. |
| 8,447,401 B2 | 5/2013 | Miesel et al. |
| 8,464,716 B2 | 6/2013 | Kuehne et al. |
| 8,480,602 B1 | 7/2013 | Cook |
| D695,856 S | 12/2013 | Jacobs et al. |
| 8,639,455 B2 | 1/2014 | Horst et al. |
| 8,679,040 B2 | 3/2014 | Horst |
| 8,840,572 B2 | 9/2014 | Whalen et al. |
| 8,900,074 B1 | 12/2014 | Johnson et al. |
| 8,900,098 B2 | 12/2014 | Egan |
| 8,968,163 B1 | 3/2015 | Vidmar |
| 9,272,175 B2 | 3/2016 | Egan |
| 9,554,964 B1 | 1/2017 | Johnson et al. |
| 9,561,149 B2 | 2/2017 | Johnson et al. |
| 9,642,764 B2 | 5/2017 | Kuehne et al. |
| 9,914,003 B2 | 3/2018 | Kuehne et al. |
| 10,004,656 B2 * | 6/2018 | Whalen .................. A63B 22/02 |
| 10,130,554 B2 | 11/2018 | Aronson |

(56) References Cited

U.S. PATENT DOCUMENTS

| | | |
|---|---|---|
| 10,132,011 B2 | 11/2018 | Malina et al. |
| 10,179,078 B2 | 1/2019 | Bhugra et al. |
| 10,265,565 B2 | 4/2019 | Jue et al. |
| 10,265,566 B2 | 4/2019 | Bayerlein et al. |
| 10,342,461 B2 | 7/2019 | Basta et al. |
| 10,398,619 B2 | 9/2019 | Crombie et al. |
| 10,427,293 B2 | 10/2019 | Asbeck et al. |
| 10,493,309 B2 | 12/2019 | Jue et al. |
| 10,533,913 B2 | 1/2020 | Lee et al. |
| 10,596,365 B2 | 3/2020 | Hyde et al. |
| 10,709,926 B2 | 7/2020 | Bayerlein et al. |
| 10,773,121 B2 | 9/2020 | Del Monaco et al. |
| 10,816,177 B1 | 10/2020 | Bayerlein et al. |
| 10,843,036 B2 | 11/2020 | Bayerlein et al. |
| 10,905,914 B2 | 2/2021 | Bayerlein et al. |
| 10,918,926 B2 | 2/2021 | Pennington |
| 2001/0018564 A1 | 8/2001 | Manor et al. |
| 2002/0010056 A1 | 1/2002 | Borsheim |
| 2002/0032103 A1 | 3/2002 | Cook |
| 2003/0032904 A1 | 2/2003 | Egger |
| 2003/0204148 A1 | 10/2003 | Lange et al. |
| 2004/0019304 A1 | 1/2004 | West |
| 2004/0171465 A1 | 9/2004 | Hald et al. |
| 2004/0238285 A1 | 12/2004 | Stokes |
| 2005/0075680 A1 | 4/2005 | Lowry et al. |
| 2005/0164839 A1 | 7/2005 | Watterson et al. |
| 2006/0009333 A1 | 1/2006 | Wang |
| 2006/0185065 A1 | 8/2006 | Allen |
| 2006/0190051 A1 | 8/2006 | Gerber et al. |
| 2006/0199712 A1 | 9/2006 | Barnard et al. |
| 2007/0016116 A1 | 1/2007 | Reinkensmeyer et al. |
| 2007/0054783 A1 | 3/2007 | Egger |
| 2007/0219059 A1 | 9/2007 | Schwartz et al. |
| 2007/0272484 A1 | 11/2007 | Helms |
| 2008/0246581 A1 | 10/2008 | Irie et al. |
| 2008/0281633 A1 | 11/2008 | Burdea et al. |
| 2008/0306412 A1 | 12/2008 | Nieminen et al. |
| 2009/0014004 A1 | 1/2009 | Whalen et al. |
| 2009/0036272 A1 | 2/2009 | Yoo |
| 2009/0047644 A1 | 2/2009 | Mensah et al. |
| 2009/0221404 A1 | 9/2009 | Dorogusker et al. |
| 2009/0236176 A1 | 9/2009 | Sheu |
| 2009/0255531 A1 | 10/2009 | Johnson et al. |
| 2009/0269728 A1 | 10/2009 | Verstegen et al. |
| 2011/0098157 A1 | 4/2011 | Whalen et al. |
| 2011/0120567 A1* | 5/2011 | Kuehne ............ A63B 21/00181 601/1 |
| 2011/0120587 A1 | 5/2011 | Kuehne |
| 2012/0238921 A1* | 9/2012 | Kuehne ............ A63B 71/0009 601/5 |
| 2013/0095459 A1 | 4/2013 | Tran |
| 2014/0194252 A1 | 7/2014 | Arimoto et al. |
| 2014/0296037 A1 | 10/2014 | Razzaq |
| 2015/0379239 A1* | 12/2015 | Basta ..................... A63B 22/02 434/247 |
| 2016/0000155 A1 | 1/2016 | Marecek et al. |
| 2016/0001118 A1 | 1/2016 | Kuehne et al. |
| 2016/0001119 A1 | 1/2016 | Jue et al. |
| 2016/0007885 A1* | 1/2016 | Basta ..................... A61B 5/112 600/595 |
| 2016/0008650 A1 | 1/2016 | Jue et al. |
| 2016/0073704 A1 | 3/2016 | Basta et al. |
| 2017/0128769 A1* | 5/2017 | Long ..................... H04L 67/10 |
| 2017/0367916 A1* | 12/2017 | Kuehne ............ A63B 21/00181 |
| 2019/0099320 A1* | 4/2019 | Whalen ................. A63B 22/02 |
| 2019/0150530 A1 | 5/2019 | Basta et al. |
| 2019/0392939 A1* | 12/2019 | Basta ..................... G16H 20/30 |
| 2020/0016025 A1 | 1/2020 | Devanaboyina |
| 2020/0108291 A1 | 4/2020 | Piazza et al. |
| 2020/0221975 A1 | 7/2020 | Basta et al. |
| 2020/0384309 A1* | 12/2020 | Long ..................... H04L 67/10 |
| 2021/0187347 A1* | 6/2021 | Remsberg ............ A61H 3/008 |
| 2021/0187348 A1* | 6/2021 | Phillips ................ A63B 22/025 |
| 2022/0054893 A1* | 2/2022 | Basta ................. A63B 24/0062 |

FOREIGN PATENT DOCUMENTS

| | | |
|---|---|---|
| CN | 2208414 Y | 9/1995 |
| CN | 2920312 Y | 7/2007 |
| CN | 103638633 B | 3/2014 |
| CN | 203647961 U | 6/2014 |
| CN | 203663349 U | 6/2014 |
| CN | 203915904 U | 11/2014 |
| CN | 104759060 B | 7/2015 |
| CN | 104800047 A | 7/2015 |
| CN | 105380657 B | 3/2016 |
| CN | 105380658 B | 3/2016 |
| CN | 105579014 B | 5/2016 |
| CN | 107158648 A | 9/2017 |
| CN | 207838129 U | 9/2018 |
| CN | 208115027 U | 11/2018 |
| CN | 208541744 U | 2/2019 |
| CN | 208893547 U | 5/2019 |
| CN | 209845965 U | 12/2019 |
| CN | 111135537 A | 5/2020 |
| DE | 20305670 U1 | 8/2003 |
| DE | 10362043 A1 | 5/2005 |
| DE | 102006010887 A1 | 9/2007 |
| GB | 2128488 A | 5/1984 |
| JP | 59002993 A | 1/1984 |
| JP | S63109878 A | 5/1988 |
| JP | H05500760 A | 2/1993 |
| JP | H0549596 A | 3/1993 |
| JP | H1022334 A | 1/1998 |
| JP | 11113988 A | 4/1999 |
| JP | 2000342713 A | 12/2000 |
| JP | 2001112686 A | 4/2001 |
| JP | 2001517187 A | 10/2001 |
| JP | 2002028202 A | 1/2002 |
| JP | 2002360644 A | 12/2002 |
| JP | 2004073445 A | 3/2004 |
| JP | 2005102798 A | 4/2005 |
| JP | 2007151676 A | 6/2007 |
| WO | 2004103176 A1 | 12/2004 |
| WO | 2006050787 A1 | 5/2006 |
| WO | 2006061834 A2 | 6/2006 |
| WO | 2007038888 A1 | 4/2007 |
| WO | 2007115565 A2 | 10/2007 |
| WO | 2008058567 A1 | 5/2008 |
| WO | 2014138228 A1 | 9/2014 |
| WO | 2019089850 A1 | 5/2019 |

OTHER PUBLICATIONS

Showa Denki Taiwan, "Showa For Medical", Oct. 16, 2014, Taiwan.

\* cited by examiner

UNWEIGHTING EXERCISE EQUIPMENT

CROSS-REFERENCE TO RELATED APPLICATIONS

This application is a continuation of U.S. patent application Ser. No. 17/980,782 filed Nov. 4, 2022 entitled "Unweighting Exercise Equipment," which is a continuation of U.S. patent application Ser. No. 17/351,226 filed Jun. 18, 2021 entitled "Unweighting Exercise Equipment" (now U.S. Pat. No. 11,517,781), which is a continuation of U.S. patent application Ser. No. 16/016,340 entitled "Unweighting Exercise Equipment" filed Jun. 22, 2018, which claims priority to provisional patent application No. 62/523,363 filed Jun. 22, 2017 entitled "Unweighting Exercise Equipment" by Whalen et al., and which is a continuation-in-part of design patent application No. 29/643,045 filed Apr. 4, 2018 entitled "Differential Air Pressure Unweighting System" by Whalen et al, all of which are hereby incorporated by reference in their entirety.

BACKGROUND

This invention relates to the field of unloading systems, and more specifically to the field of unloading systems using air pressure for the purpose of fitness training and rehabilitation.

Systems for unweighting individuals for rehabilitation and fitness training has always been a popular modality. Traditional methods have included aquatic training and using a hoist to lift a person or animal off a walking surface. Recently, systems creating a pressure differential across a portion of a user have been developed and are generally in commercial use in the rehabilitation and training centers around the world.

Whereas aquatic systems are very difficult to control in terms of degree of off-loading, a system creating a pressure differential can vary the pressure differential very precisely allowing for a wide range of unloading in very small steps. One benefit of this is in the case of rehabilitation it has been shown that increments as small as 1% of normal body weight are effective at determining a pain threshold below which a user can exercise pain free.

Harness, or hoist systems allow for precise and granular unweighting, however they become significantly uncomfortable at off-loading of greater than about 25% of normal body weight.

Both harness systems and aquatic training alter normal gait pattern more than a differential air pressure (DAP) system which applies a pressure difference at a portion of the user's body with a net force at the center of pressure. If the net pressure differential is oriented parallel with the force of gravity and located near the user's waist, this off-loading force acts approximately directly counter to the force of gravity and therefore minimally alters the users natural gait patterns.

DAP systems have been commercialized by companies like Showa Denki in Japan, Sasta Fitness of the UK, Vacuwell of Poland, and AlterG Inc. in the US. While these systems offer benefits, they are expensive, large, non-adjustable, require specialized power sources, or are generally limited in access to the market because of the high cost and space burden, or general discomfort in design for users of different body types or heights for example. Further, since many customers already have existing exercise equipment in their facility, sometimes brand new, it is inconvenient for a customer to have to choose between throwing away something they just bought, and putting in a DAP system. In this specification, the applicant may refer to an exercise machine and an existing exercise machine. The reader shall note that the distinction is that an existing exercise machine may be already designed prior to consideration for use as a DAP system and an existing exercise machine may be further already installed in the field, for example in a gym, training facility, etc. The reader shall interpret minor modifications of the exercise machine or existing exercise machine for use with a DAP system as still part of the exercise machine and still within the spirit of the scope of this invention. Prior art has substantially altered or discarded whole portions of what would be considered the exercise machine or existing exercise machine in creating prior art DAP systems, and one principle benefit of the applicant's invention is that the applicant does not require this modification or discarding of components in creating the applicant's DAP systems. Vacuwell. Showa Denki, and AlterG products all appear to only use a base portion of a treadmill but not the console, or handrails or other support members.

All current DAP systems to the applicant's knowledge build a shell, hard or soft, around an existing treadmill or bicycle as the exercise equipment inside. A completely separate chamber is formed and a base portion of the exercise equipment, for example the running belt/rollers/deck of a treadmill or the seat and pedals of a stationary bicycle, effectively dropped inside. While simple in construction, this structure duplicates the framing of the combined system and therefore increases the cost, size, shipping bulk, part count, and overall complexity of the system. No current DAP systems to the applicant's knowledge integrate an existing piece of exercise equipment's framing, console, or other parts aside from the base assembly supporting the user into DAP system and in particular don't use those elements to satisfy the structural requirements of the DAP system in order to economize on the number of pieces used in the design and reduce part count, cost, shipping and installation bulk and time, and overall complexity of the manufacturing, assembly, installation, and service operations. An "add-on" or "retrofit kit" concept, as the applicant has invented reduces the cost and complexity of a DAP system significantly and as the applicant will describe, breaks down the key components of a DAP system into few, compact components that efficiently constrain and transfer load such that existing exercise equipment framing may adequately carry newly introduced loads for which they were not necessarily originally designed. Utilizing the existing exercise equipment's structure vs building a brand new structure around the system not only enables the overall product to take advantage of mass volume production, but also allows existing product in the field to be "upgraded" and converted into a DAP system. Regarding mass production, if for example 1000 pc of a treadmill model are produced per year, and 100 of those are converted to be DAP capable, those 100 pieces will have the majority of their components built at volume scale cost of 1000 pc, not the limited build volume of 100 pc.

Additionally, as no existing DAP products are fully integrated into an existing equipment's framing, nowhere in the prior art could it be found that an integrated DAP system can adequately accommodate any incline of the existing exercise equipment and the resulting tilt of the area around the user that forms the pressure differential. AlterG's P200 and M320 products both comprise a flat solid base on top of which the exercise equipment elevates, however this has the effect of lifting the user out of the seal area and thereby changing the unweighting relationship for the current pressure in the chamber. Sasta Fitness products and Vacuwell products don't incline to the applicant's knowledge and Showa Denki's system appears to behave similar to AlterG's products. This oversight is significant as the user is effectively reduced to exercise at a fixed incline level and deviation for that setting causes an abrupt change in amount of unweighting the user is getting vs. what they are expecting because less or more of their body is inside the chamber as the tilt angle changes. As the applicant will disclose, the applicant's inventions allow for incline of the full chamber in conjunction with the incline of the exercise equipment so the height of the seal frame to the support surface stays constant, and the angle of the seal frame similarly is adjustable to remain parallel with the ground so the unweighting force is directly counter to the force of gravity thereby producing natural gait mechanics, meaning that certain existing equipment on the market can be retrofitted with the applicant's inventions, giving an option to upgrade existing equipment vs. having to throw good equipment away and replace with a fully integrated system, which still doesn't optimally accommodate incline. This option saves the client money, ease of logistics, and gives clients more flexibility as to how they want to integrate DAP technology into their business or lifestyle.

Substantial vertical and lateral forces in the thousands of pounds are developed in the DAP chamber because of the large surface area that is exposed to the pressure. As existing exercise equipment framing is not designed to accommodate this external loading, it is critical to the integrity of the combined system that the add-on portion be designed to avoid improper load points and forces that could damage existing equipment, or that reinforcements be applied where needed. These forces may be lateral from expansion of the sides of the system or vertical in the case of vertical expansion of the system. To date, no designs to the applicant's knowledge have attempted to adapt to or add on to an existing piece of exercise equipment so there are no considerations in the prior art as to how to accommodate new forces generated by the chamber and DAP system in general. In particular the products of Sasta Fitness, Vacuwell, and AlterG appear to use a third party treadmill base as the exercise machine but don't use hand railings or any other aspects of the existing equipment's structure in the structure of the system, but instead build customized structures in order to support electronics and user seal areas, etc. The applicant's invention will disclose various mechanisms for constraining these forces internally and utilizing the existing structure of the exercise device to carry the load effectively, particularly from a fabric chamber.

The accuracy of current DAP systems has also been questioned as to how well various calibration techniques or routines function. The lack of accuracy and even change of the pressure/weight relationship during a session enforces the idea that the exact level of unweighting is not actually the critical factor but rather a consistent pressure setting, as read on a generic scale readout for unweighting, is what is important from one session to the next. In other words, a consistent relative pressure setting capability (for example a scale of 1-100 where 100 is always 45 mmHg) is just as effective as an absolute pressure setting for a given individual. This is further evidenced by the practical implementation of the therapy for example where a therapist may simply take small increments of weight off until there is no more pain, and call it "good". U.S. Pat. No. 5,133,339 to Whalen, and U.S. Pat. No. 7,591,795 to Whalen et al. discuss the pressure to weight relationship. U.S. Pat. No. 5,133,339 provides experimental data where effective user weight was measured real time at various pressures and plotted to view the relationship between effective weight and pressure and discusses various formulae related to calculating this relationship. U.S. Pat. No. 7,591,795 extrapolates on that idea by adding load cells or a measurement system into the machine for automatically generating multiple pressure and weight pairs and then forming a pressure-weight relationship using that data as a prediction method of adjusting weight by varying pressure without having to stop and take an actual weight measurement again or display a real time weight reading.

U.S. Pat. No. 7,591,795 however introduces complications into the system by requiring a weighing system to be built into the exercise equipment and also has inherent inaccuracies as the relationship may be non-linear or affected by position of the seal frame or incline, or require excessive time during the setup process to get a sufficient amount of points to more accurately construct the relationship etc. The requirement of building in load cells immediately eliminates the concept of a retrofit kit or add-on kit and the requirement for this function illustrates a misunderstanding and anticipation of the market requirements and what is really needed for effective use. In the case in some prior art, the weighing system may be located under the treadmill, and therefore must taking the pounding associated with continual use. In all cases, load cells are not cheap and the added cost, servicing burden, and overall complexity of the system is significant. The applicant will provide an apparatus and method herein for achieving the benefits of creating a user-specific, consistent, off-loading-to-pressure relationship without taking actual weight measurements of the user and thereby eliminating the load cells or a weight measurement system from the design. The applicant will further illustrate how the system can be simplified and provide the critical benefits of prior art without the complication of hardware and software of the prior art.

All prior art systems to the applicant's knowledge consist of a rigid base plate under the exercise machine base for sealing the base in a substantially airtight environment. This base plate is necessarily large as it must accommodate the full area underneath the exercise device base. A large surface area means that when pressure is applied there is a large force applied to the rigid base which requires a substantially strong or reinforced rigid base piece. Generally, this is not desirable as it increases the weight and shipping bulk of the overall system which makes moving and installing difficult, and increases shipping costs as the size of the package must be at least as large as the rigid base piece. In the case of a retrofit kit, a rigid base plate not only increases shipping costs unnecessary as the equipment that is physically big is already installed, but also complicates assembly with an existing piece of exercise equipment that must incline. Generally, for a retrofit situation, a rigid base plate may require an incline assembly to be removed from the exercise device, the base plate installed, and then the incline assembly attached external and beneath the rigid base plate. Using a rigid base plate outside of the exercise device ends up creating the design of existing DAP systems that work in this way. One aspect of the applicant's invention by contrast may use a fabric bottom with lightweight reinforcement bars. The benefits being that a fabric bottom is easily packaged compactly and the overall weight, bulk, and size is dramatically reduced. The fabric carries the tensile force and efficiently carries the load from the pressure. Furthermore, the fabric base assembly may be more easily adapted for certain kinds of incline systems via ports and compartments as described herein, without significant costs in construction or assembly complications.

A fabric chamber surrounding the exercise devices has several other advantages over the prior art in terms of servicing, removal of the chamber for use as a normal exercise device, cleaning, and general access. Whereas rigid framing, bases, etc. require doors, latches, or other "rigid" entry and exist points, a fabric chamber can employ an airtight zipper in order to gain access to the internals of the chamber. For example, the applicant will illustrate certain locations where it may be advantageous to add such airtight zippers in order to make cleaning of the inside very simple, to gain access to internal electronics of the exercise device such as on/off buttons, and to remove entirely an upper fabric chamber in order to operate the exercise device normally, as if the DAP system had never been added in the first place.

Finally, the applicant will describe a mechanism for minimal and universal interfacing of the DAP system with existing exercise equipment in order to safely control and monitor how the integrated system functions. All prior art to the applicant's knowledge customizes consoles and console support members because these lie outside of the chamber. This is similarly less efficient than using existing components as described above and requires customized hardware and software controls to adapt the behavior of the exercise machine into the behavior of the unweighting system controller. This further illustrates the prior art's lack of anticipation of a retro-fit kit because such systems would not be reusing a majority of components of the existing machines. In terms of a universal theory for operation for example, it is undesirable that the exercise equipment operates before the exercise equipment is permitted to be used safely. AlterG's P200 product and M320 product for example appear to limit the ability to start the treadmill prior to inflation of the chamber. In both cases the systems appear to have customized control panel housing, etc. and are not readily adapted to other types of treadmills or to treadmills in the field. The applicant by contrast will present several concepts for how to safely and simply integrate into a wide range of exercise equipment without needing extensive customization between designs.

Accordingly, besides the objects and advantages of a DAP system for use in rehabilitation and training as described in this application, several objects and advantages of the present invention are:

a) to provide an unweighting system that may retro-fit to existing pieces of exercise equipment in the field
b) to create a simplified unweighting system that provides consistent unweighting levels without requiring a load sensing system
c) to provide a system that efficiently carries applied loads so that existing equipment is not adversely affected
d) to provide a DAP system that accommodates traditional incline mechanisms for certain exercise equipment
e) to provide a DAP system that takes advantage of existing exercise equipment framing to carry load efficiently in order to avoid duplication of these structural elements and allow field upgrades
f) to interface safely and simply with existing exercise equipment in order allow control of both systems in a manner that will not put the user at risk.
g) To provide a DAP system where an upper portion of the chamber is removable to allow use of the exercise equipment as "normal"
h) To provide a DAP system wherein access is provided in the fabric portion of the chamber in order to facilitate cleaning or access to internal electronics for servicing.
i) To provide a sealing assembly for sealing a separating fastener
j) To provide reinforcements where needed to ensure structural integrity of existing equipment frame members
k) To provide alternatives for height adjustment that simplify structure, part count, and cost, and improve easy of ingress and setup.

Still further objects and advantages will become apparent from a consideration of the ensuing description and drawings.

SUMMARY

In accordance with the present invention, an unweighting assembly is provided for integration with an exercise machine to create a DAP unweighting system with minimally designed structure sufficient to carry required loads, and allowing simplified unweighting of a user without compromising the utility or effectiveness of the DAP unweighting system for physical training or physical therapy.

DETAILED DESCRIPTION

Preferred Embodiment—Description

Figure 1A:
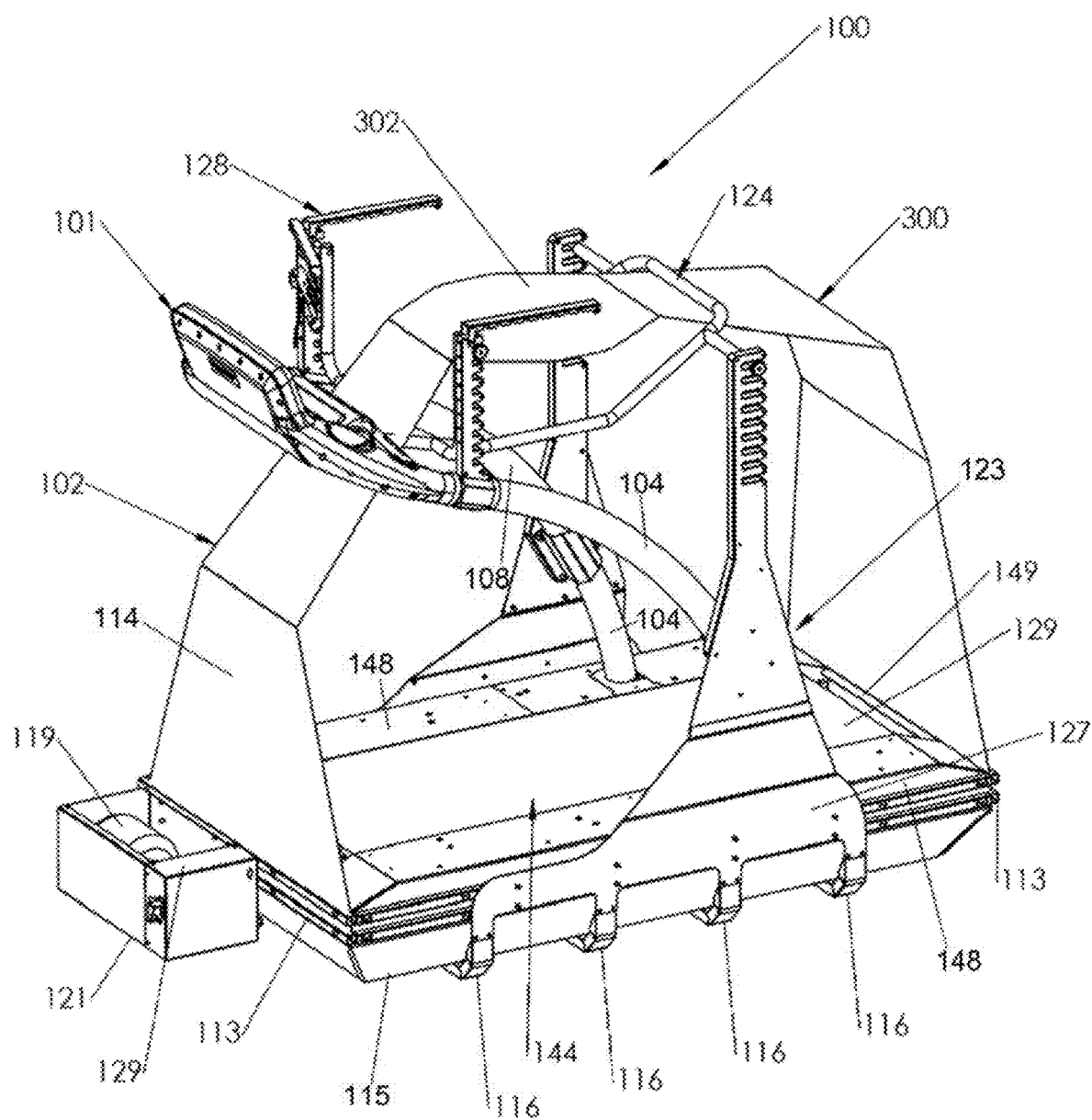
FIG. 1A—Shows a DAP unweighting system formed by integrating an unweighting assembly with an exercise machine FIG. 1B—Shows one example of an unweighting assembly which is adapted for integration with an exercise machine to form a DAP unweighting system.

FIG. 1A shows a DAP unweighting system 100 created by adapting an unweighting assembly 102 to an exercise machine 101. The unweighting assembly 102 and variations on the exercise machine 101 are described in later figures in greater detail. Previous air pressure based unweighting systems have used exercise machine bases 144 only, namely treadmills, and built entirely new structures around the base as described in the background section. In so doing, the prior art systems increase the footprint, number of custom components, cost, and overall complexity, bulk, and weight of the system. The applicant's invention seeks to minimize component count and take advantage of existing exercise equipment design by creating and adapting an unweighting assembly 102 to a piece of exercise equipment 101 such that as many components as possible, and in particularly structural components, are used for dual purpose in the exercise machine function and the unweighting assembly function vs. common practice in the prior art of throwing many components away and creating a totally separate system around the exercise machine base 144 portion of exercise equipment. Beyond the advantages of minimized cost, component count, and ease of manufacturing, this also allows users to upgrade an existing exercise machine 200 they already own, as in examples shown in FIGS. 2A-B, thereby reducing acquisition cost and making the product more available to the general market to increase adoption. Finally, an exercise machine 101 with an actuator that bears load from the weight of the exercise machine, such as an incline assembly 134 on a treadmill may only be able to bear limited additional weight capacity. To re-use components, particularly a structural member 110 is critical for making possible the concept of taking advantage of the design work already done plus installed base already in the field via combining an adaptable unweighting assembly 102 with an exercise machine 101 to convert the exercise machine into a DAP unweighting system 100.

Unweighting Assembly—Sealing Surface

A preferred embodiment of the unweighting assembly 102 is depicted in FIG. 1A as coupled to an exercise machine 101. The unweighting assembly 102 is described and illustrated in a basic form in this specification, but the reader shall note that additional features and components may be added in order to improve or alter the functionality and capabilities of the combined DAP unweighting system 100. Some of these features and functionality are noted below but the reader shall note that the applicant's invention is not limited in scope only to the features and functionality improvements mentioned in this application.

Figure 1B:
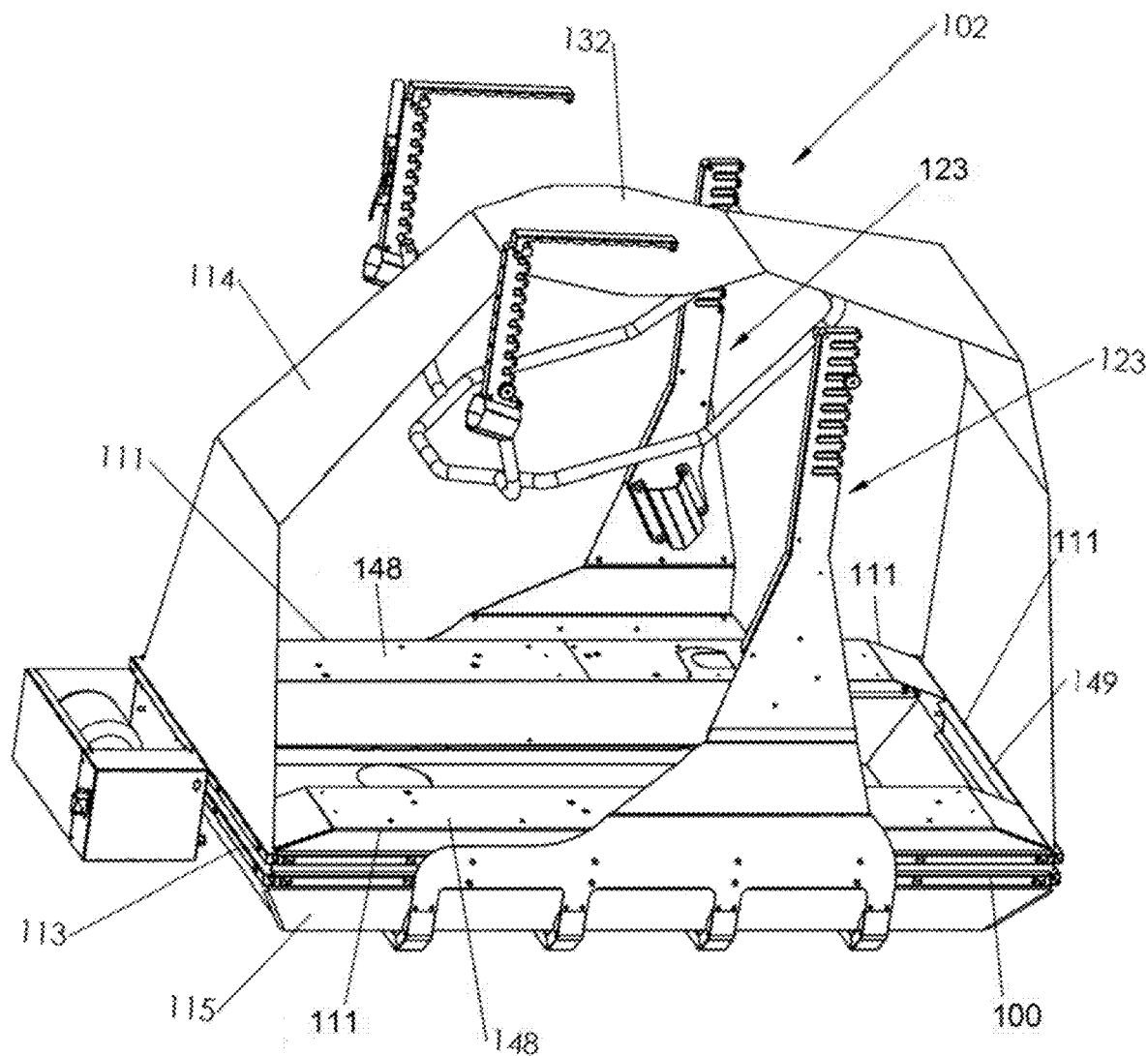
FIG. 1C—Shows an exploded view of the unweighting assembly of FIG. 1B.
Figure 1C:
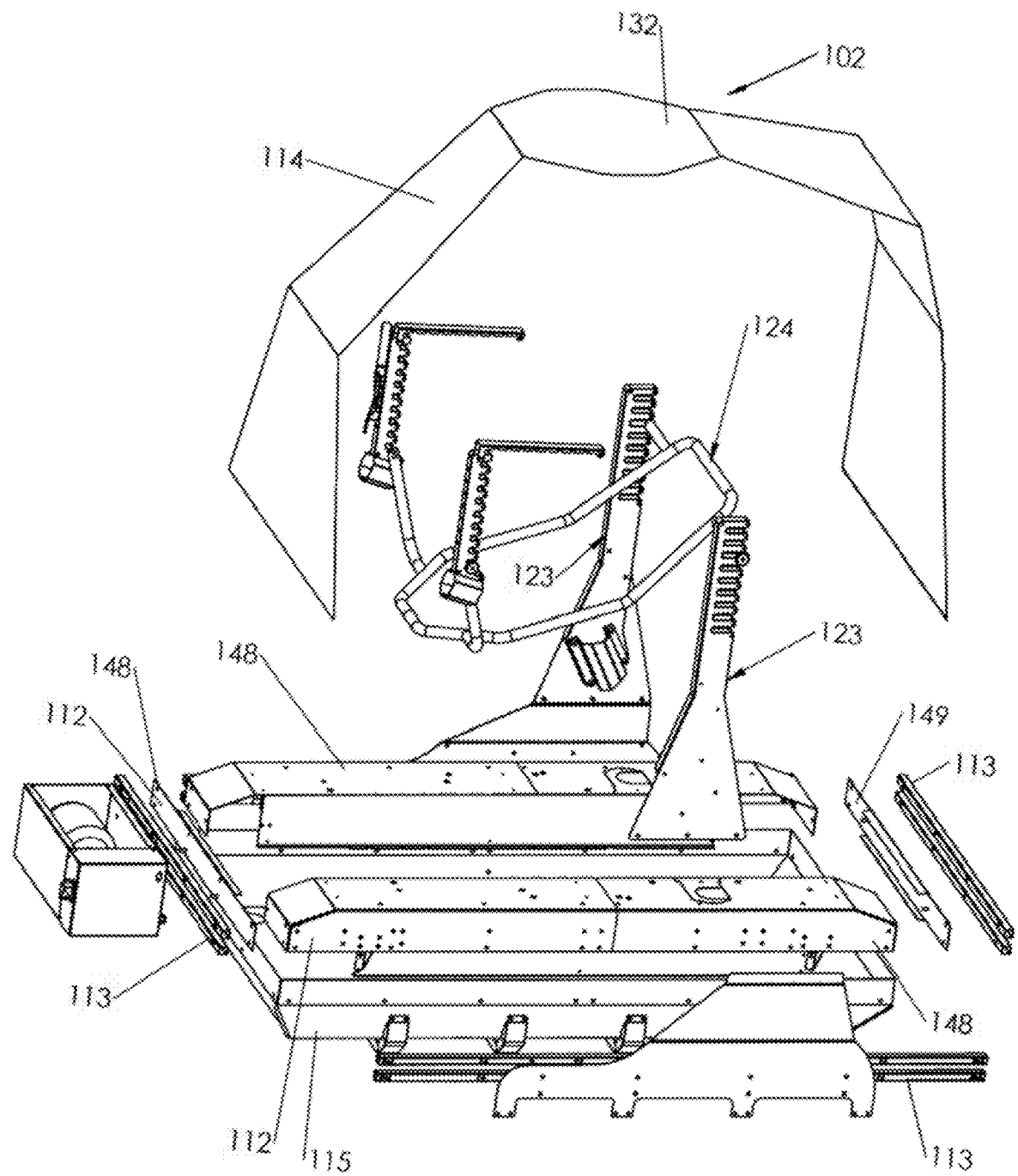
Figure 3A:
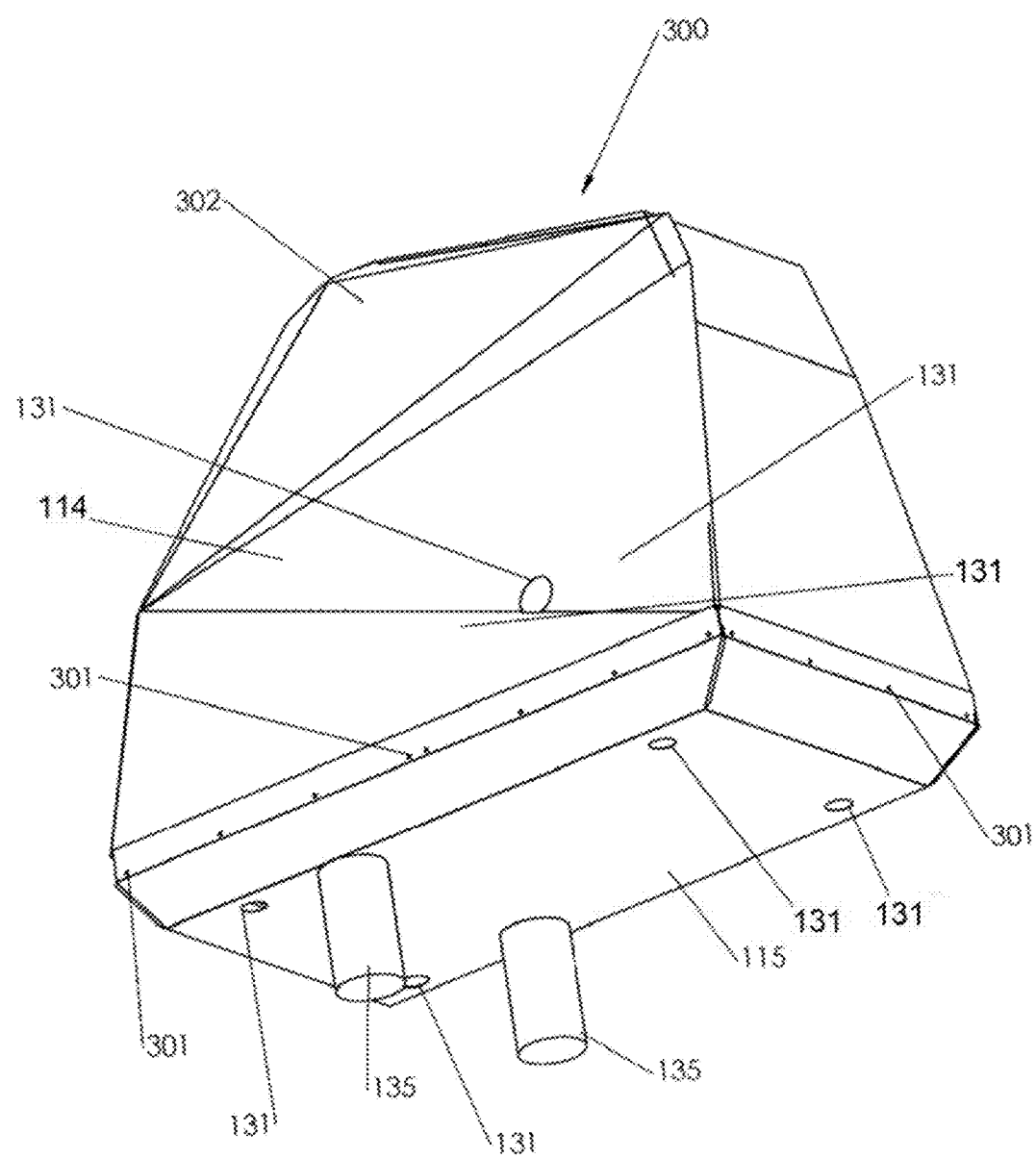
FIG. 3A—Shows one variation of a chamber for creating an airtight environment around an exercise machine, the chamber comprising an upper portion and a lower portion and a plurality of port assembly and chamber compartments for accommodating elements of an exercise machine.
Figure 3B:
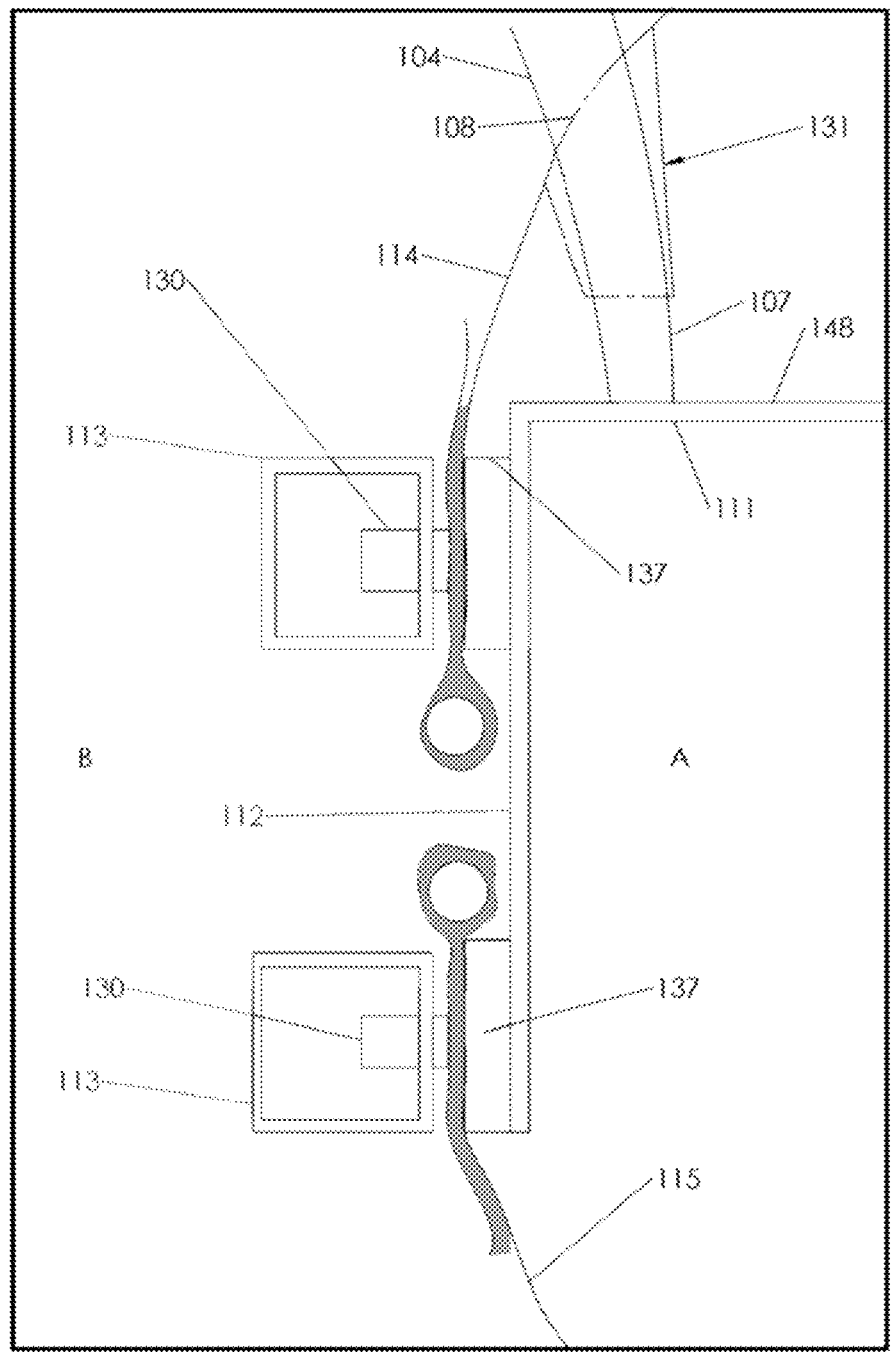
FIG. 3B—Shows one variation for securing an upper chamber portion and a lower chamber portion to an additional frame member for creating an airtight environment around an exercise machine. With an ambient side B and a pressurized side A.
Figure 5:
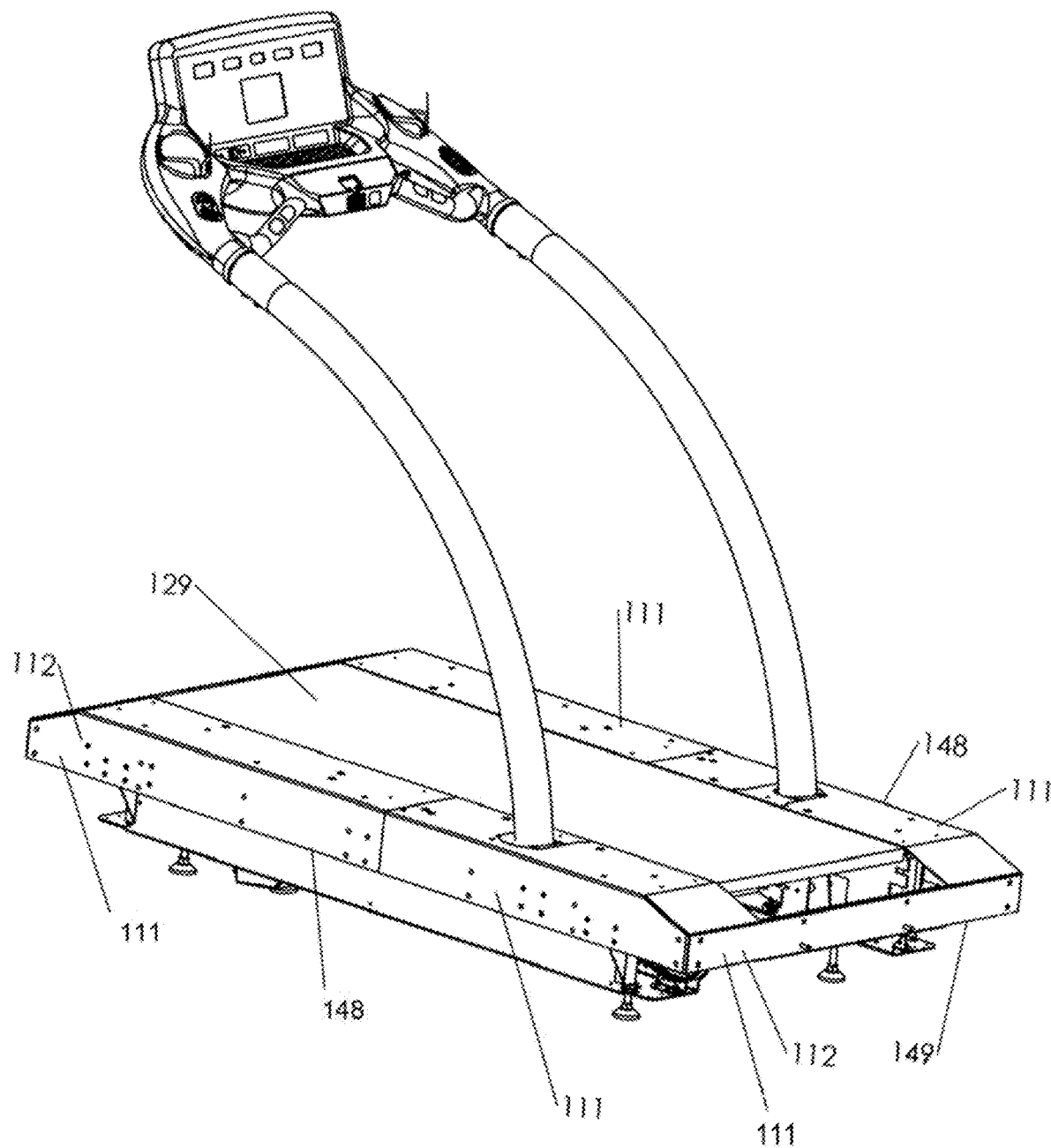
FIG. 5—Shows a variation for attaching a plurality of additional frame members to an exercise machine for creating a sealing surface around a perimeter of the exercise machine.

The unweighting assembly 102 may provide a sealing surface 112 for an upper chamber portion 114 and a lower chamber portion 115 as shown in FIGS. 1C, 3B, 5. The reader shall note that in FIG. 1A-C, FIG. 8, the sides of the upper chamber portion 114 have been hidden so as to allow the reader to see the internal elements and structural elements, but that the sides are shown in FIG. 3A. The sealing surface 112 may be, but is not limited to being, planar, polygonal, or curved. One important aspect of the sealing surface 112 is that it provides a location to continuously seal the chamber 300, either an upper chamber portion 114, lower chamber portion 115, or both in a sufficient airtight manner such that the exercise machine 101 rests inside a substantially airtight environment. The reader shall note that the applicant may refer to the chamber 300, and in so doing may mean either the upper chamber portion 114 or lower chamber portion 115 as well as the combination. The sealing surface 112 may be formed around a perimeter that is large enough to fully enclose the exercise machine 101 such that an airtight environment may be formed around the exercise machine. An example of such a sealing surface 112 is shown in FIGS. 3B,5 as a rectangular surface created by 2 side covers 148 and 2 end covers 149 with 2 sections parallel with two side faces and 2 sections parallel with two end faces of the exercise machine 101 (a treadmill as shown). The rectangular sealing surface 112 runs external to the exercise machine 101 such that the entire exercise machine is encompassed within the sealing surface.

The sealing surface may be augmented with various fasteners 130 such as threaded nuts as shown, threaded studs, clasps, clamps, ¼ turn screws, etc., as shown in FIG. 3B, and the fasteners may be configured to communicate with chamber retaining members 113, depicted as rectangular tubing sections in FIGS. 1A,B,3B. The chamber retaining members 113 may in turn secure the upper chamber portion 114 or lower chamber portion 115 to the sealing surface 112 in a substantially airtight manner as shown in FIG. 3B. A gasket 137, shown in FIG. 3B, may be sandwiched between the sealing surface 112 and a portion of chamber 300 but is not necessarily required depending on the properties of the chamber and sealing surface and the amount of leak that can be tolerated. For example if pressure source can provide sufficient flow into the chamber 300 some amount of leak may be allowed between the sealing surface 112 and the chamber 300 and a gasket not necessary, and this leak amount may be reduced by choosing a softer material for the chamber. The chamber 300 and materials are described later in more detail. FIG. 3B illustrates in more detail the sealing scheme of FIG. 1A where fasteners 130, depicted as bolts are threaded from the inside of the additional frame members 111, shown as side cover 148 in FIG. 3B, to form removable threaded studs poking to the outside (side B as shown) of the sealing surface 112.

Additional frame members 111 are elements that are added to the exercise machine 101 as part of the unweighting assembly 102 to create the necessary structures for attaching the chamber 300, or other required elements, or to reinforce existing frame elements 103, in order to create a functioning and reliable DAP unweighting system 100. Additional frame members 111 may be side covers as shown in FIG. 5, bars, hooks, plates, tubes, or any such element that is added to the exercise machine 101 during the upgrade or integration process.

Existing exercise machine frame elements 103 is the applicant's generic term for those elements that comprise the frame of an exercise machine such as hand rails, roller mounts, incline carriages, console mounts or stanchions, etc.

Structural elements 110 are those elements that are desired to carry high load during use from the DAP unweighting system 100, and may comprise handrails 104, (FIG. 2A-B) additional frame members 111, existing exercise machine frame elements 103 or any component that carries load.

Figure 2A:
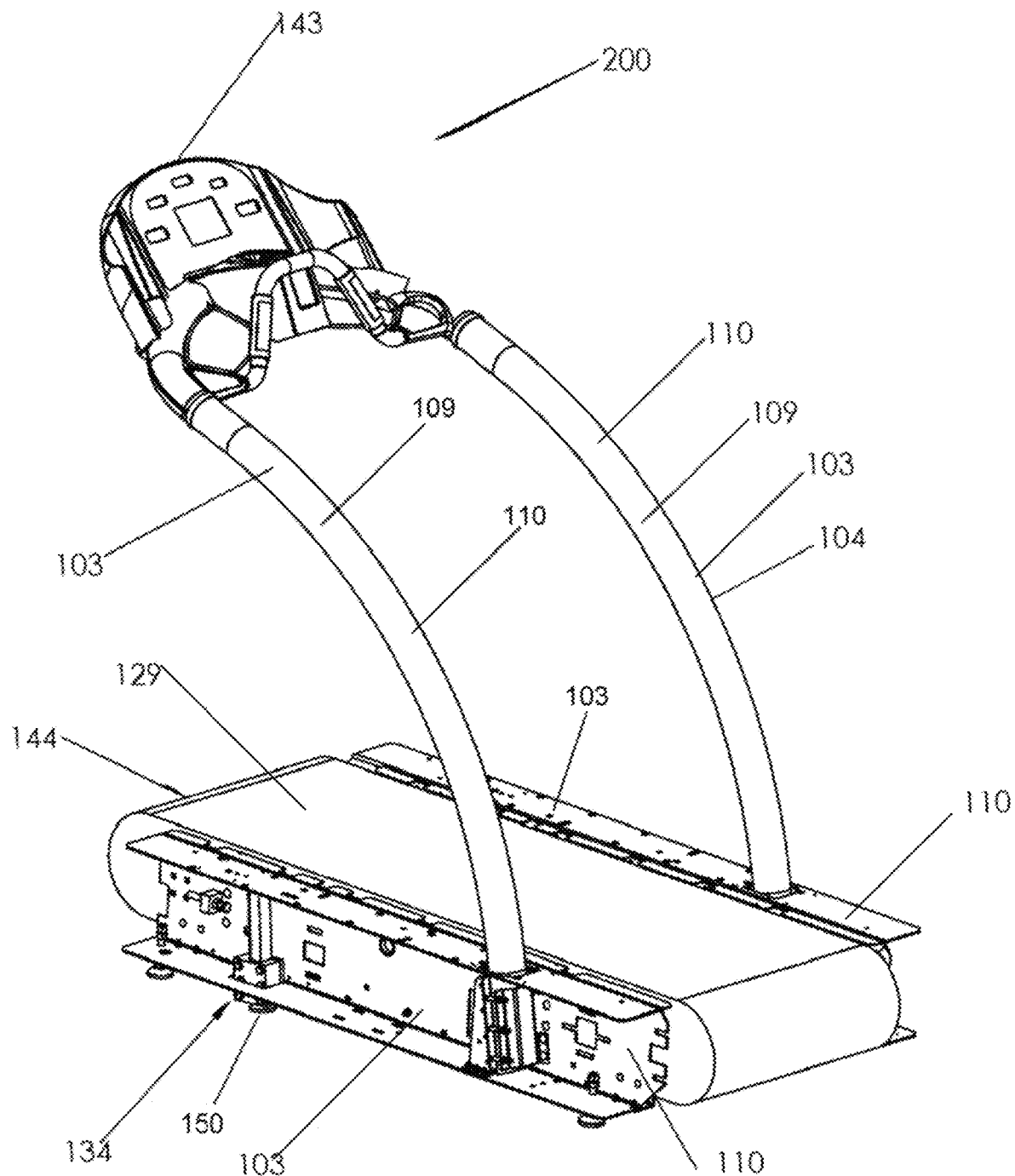
FIG. 2A—Shows one example of an existing exercise machine which is suitable for integration with an unweighting assembly for creating a DAP unweighting system using a rack and pinion incline assembly.

Console support members 109 are elements of the DAP unweighting system 100 that support the control console as shown in FIG. 2A.

Therefore, in the figures, where the reader sees multiple references to a single element the applicant is trying to illustrate that that element may serve several functions and purposes. For example the handrail 104 of FIG. 2A constitutes an existing exercise machine frame element 103 because it part of the existing exercise machine as originally designed. It also constitutes a console support member 109 because it supports the control console; it constitutes a handrail 104 because it is intended to be used as a handle bar for the user; and it constitutes a structural member 110 because it is designed to carry load when inflated and prevent the chamber from increasing in width or height. For the sake of clarity each component is not always labeled with each specification and the reader shall use common sense to understand the function of each element in the applicant's design.

For FIG. 3B, a nut (not shown) may then be provided on the end of the threaded stud to clamp the chamber retaining member 113 by moving the chamber retaining member from side B towards side A and in doing so, compressing the chamber 300 and gasket 137 together. An advantage to the fastener 130 being removable bolts is that if threads are damaged they may be replaced without replacing the entire additional frame member 111. The threaded nuts plus bolts may be replaced by permanently connected threaded studs such as PEMS fasteners, welding, or other component/ process combination known in the art. The chamber 300 and chamber retaining members 113 are therefore removable to allow for removal of the chamber from the studs and sealing surface 112. The chamber 300, or a portion thereof, as shown in FIG. 3A,B may have mating hole cutouts 301 to match the fastener 130 (stud) pattern and the width of the chamber retaining member 113 may be sufficient to seal the area of the chamber 300 immediately around the fasteners 130 to the sealing surface 112 so that no appreciable leak is allowed past the fasteners. The width of the chamber retaining member 113 may be for example the same width as the gasket 137. The chamber 300 is constructed with sufficient dimensions so as fit onto all the fasteners 130 around the perimeter. The fitting may be facilitated by a degree of elasticity, or stretch in the material itself of the chamber 300, or in addition of a portion of elastic or stretch fabric (not shown) for example in one or more corner of the chamber. These are but a few examples of how the chamber 300 can be compliant, but as long as the chamber is configurable to fit over the fastener 130 pattern without excessive slack, any variation providing this fitting aspect of the chamber construction shall be considered within the scope of this invention.

Unweighting Assembly—Additional Frame Members

Additional frame members 111 as mentioned above may serve to create a sealing surface 112 onto which the chamber 300 may be attached in a substantially airtight manner. The additional frame members 111 may be adapted in shape and size to connect via fasteners 130 (not shown in FIG. 5) to the exercise machine 101 as shown in FIG. 5. Attachment means may include screws, bolts, double stick tape, mechanical interference in the form of latches, clasps, clamps or otherwise any attachment means generally understood in the art to connect two rigid bodies together. The additional frame members 111 may optionally replace components of the exercise machine 101, but are not required to do so and may instead rest on top of existing side covers for example. It is desired, but not necessary, that additional frame members 111 do not replace structural members 110 of the exercise machine 101 in keeping with the spirit of the applicant's invention to reduce additional component count to convert an exercise machine into a DAP unweighting system 100. In this manner the size, weight and strength of the additional framing components 111 may be kept to a minimum in order to minimize the amount of added weight, material, cost, and bulk in shipping and ability of an incline assembly 134 to incline. Additional frame members 111 may be provided in sections, for example two pieces along the length of the exercise machine as shown in FIG. 5, or may be integrated into fewer sections, and even a single section that maybe placed over the exercise machine in as a single piece. Breaking up the sealing surface 112 into multiple additional frame members 111 may be advantageous for shipping retrofit "kits" out to customers by reducing the package size. The reader shall note that in such cases, design elements of the additional frame members 111, and any additional gaskets 137 may be further provided so as to create a substantially uniform sealing surface 112 around the exercise machine 101 when the additional frame members 111 are connected to the exercise machine as shown in FIG. 5.

Additional frame members 111 are depicted in FIG. 5 as four side covers 148, two on a left and two on a right side of the exercise machine 101 as well as a two end covers 149 in the front and back of the exercise machine respectively. The additional frame members 111 are shown as bent 2 mm thick sheet metal, preferably a steel or aluminum alloy but may be carbon fiber or other rigid material that sufficiently provides enough load bearing capacity to secure the chamber given the overall system design and pressures/loads expected. The additional frame members 111 are sized according the exercise machine 101 and desired to be as small as possible to reduce footprint while still fulfilling their required functionality. The additional frame members 111 may contain multiple sets of fasteners 130, or may themselves be expandable via addition of intermediate sections (not shown) that effectively lengthen, shorten, widen, or otherwise dimensionally or functionally alter the additional frame members. By being modifiable to adapt and connect to more than one model of exercise machine 101, for example if used in a universal "kit" concept as described in this application, the additional frame members 111 can reduce overall inventory part count and optimize production and logistics efficiency. Alternatively, additional frame members 111 may be optimized and designed for only one model of exercise equipment.

When assembled as shown in FIG. 5, a vertical sealing surface 112 in the form of a rectangular wall, is created around the perimeter of the exercise machine 101 as described above and illustrated in cross section in FIG. 3B. If an alternate orientation of the sealing surface 112 as described in alternate embodiments #2 or #3 were desired (see also FIG. 12), the end covers 149 could be connected to the top surface of the side covers 148 to create a substantially planar and flat horizontal sealing surface to which the chamber may be attached and sealed substantially airtight.

The additional frame members 111 therefore may serve as the intermediary foundation connecting the exercise machine 101 to the chamber 300, forming an optional sealing surface 112, and supporting any other structural components used to shape or constrain the chamber or hold other system components such as a blower 119 or electronics box 121 as described later.

Unweighting Assembly—Chamber

The chamber 300 may be comprised of several sections as shown in FIG. 1A-C, namely but not limited to, an upper chamber portion 114 and a lower chamber portion 115. Additional sections may be provided, and may be removable as long as such attachment, or section of the chamber 300, is done in a sufficiently airtight manner. The applicant discusses herein several possible methods for removably fastening parts of the chamber 300 together in a sufficiently airtight manner, but the reader shall note there are many ways known to those skilled in the art and the applicant's inventions shall not be limited only to the methods disclosed herein.

The chamber 300 may alternatively be a single construction (not shown) with a separating fastener 1000 (for example shown in FIG. 10A,B) as previously described that opens to allow insertion of the exercise machine 101 and then seals around and completely encloses the exercise machine to complete the substantially airtight environment. In this instance the chamber 300 may be fabricated as an integrated component, combining the upper chamber portion 114 and lower chamber portion 115 via suitable means such as sewing or seam taping and shall retain the critical elements and functions of the chamber as described in this application. As an integrated component, the reader shall note it may be advantageous to have a different pattern construction or design versus the "top and bottom" design described in this application, and any such pattern designs that form an integrated component with an opening for the exercise machine 101 shall be considered within the scope of this invention.

The reader therefore shall note that as long as the chamber 300 completes an airtight environment around the exercise machine 101, the other details of the chamber may be modified: size increased or decreased, walls hardened or softened, window viewing areas added or removed, support rods or plates to aid in folding or shaping added or removed, etc. without departing from the spirit of the applicant's invention.

The upper chamber portion 114 and the lower chamber portion 115 are preferably a flexible fabric material, for example a ballistic nylon with polyurethane or PVC coating, however the lower chamber portion may alternatively be a rigid construction such as fiberglass molding, sheet metal assembly, or other combination known to those skilled in the art or disclosed in prior art. A fabric lower chamber portion 115 is advantageous over prior art such as AlterG P200 and M320 or Sasta Fitness in that the weight, shipping size, and ease of assembly is significantly improved over the rigid bases of existing DAP systems, where the lower chamber portion forms a platform on top of which the exercise machine 101 rests. This is particularly true if the exercise machine 101 to be adapted to is an existing exercise machine 200 already installed in the field as flexible material may be more easily slid under the existing exercise machine versus having to lift the existing exercise machine to a substantial height off the ground to fit a rigid lower chamber portion 115 underneath. A flexible lower chamber portion 115 may also be more easily adapted to accommodating various types of exercise machines 101 by simply sewing and seam taping pockets, port assemblies 131 or other features in order to accommodate power cables, data cables, pressure ports, incline mechanisms, level feet, or other physical aspects of the enclosed exercise machine. Reduction in weight by using a fabric lower chamber portion 115 may also allow the exercise machine 101 to incline without overloading the existing incline motors whereas a rigid lower chamber portion may be too heavy and require upgrading of the incline assembly 134 on the exercise machine.

The chamber 300 may be provided with one or more ports and/or port assemblies 131, such as the conical sleeve in FIG. 3B, which allow for passing cabling, structural members 110, existing exercise machine frame elements 103, such as handrail 104 in FIG. 3B or other objects from inside the chamber to outside the chamber (or vice-versa). In the case of existing exercise machine frame elements 103 the chamber 300 therefore may intersect the existing exercise machine frame element so that a first frame element portion 107 is enclosed inside the substantially airtight volume annotated as section A in FIG. 3B, and a second frame element portion 108 is outside of the chamber and not in the pressurized volume annotated as section B in FIG. 3B and also shown in FIG. 1A. The chamber 300 may further include a plurality of optional ports or port assemblies 131 that are provided to make a chamber universal as to adapt to more than one model of exercise equipment. The size, shape, length, location, or other physical characteristic of the port assembly 131 may be modified to make adaptation easier to fit other models. For example, a port assembly 131 specific to accommodate one round shaped handrail 104 of a model of treadmill may be approximately 3 inches in diameter and formed via a fabric sleeve with clamping fastener such as a hose clamp disposed to clamp the sleeve to the handrail 104 104 such as the curved hand rail shown in FIG. 1A. This same port assembly 131 may also be in diameter to accommodate a hand rail of another model of treadmill where the handrails 104 are spaced narrower in width and therefore physically located in a different point in space relative to the first treadmill model's handrail 104. The shape and dimensions of the port assembly 131 may also be oblong, rectangular, etc and the reader shall not there are many such modifications that are suitable. An increased diameter of the port assembly 131 to 10 in, for example when configured as a fabric sleeve for attaching to a hand rail as shown in FIG. 1A, allows the base of the sleeve where it attaches to the handrail 104 to move in space relative to the inflated shape of the chamber 300, and still be securable to the handrail even though the handrail 104 connection is in a different point in space. Bellows 135, or conical bellows elements may be in communication with the port assembly 131, for example a sleeve, to facilitate movement (like a gear shift boot on an manual transmission car), while maintaining ability to seal a handrail in this example. While the applicant has provided one example of how the chamber ports or port assemblies 131 may be altered to be made more universal, by increasing a diameter dimension, the reader shall note there are other ways to modify dimensions, locations, material properties and elasticity etc, and the applicant's invention shall not be limited only to the examples provided herein.

Port assemblies 131 may be used to pass existing exercise machine frame elements 103 or console support members 109, such as bars, stanchions, or handrails 104 from inside the chamber to outside the chamber as previously described and shown in FIG. 3B. This allows for connection of chamber 300 to the exercise machine 101, for example via additional frame members 111, and allows the lower chamber portion 115 and upper chamber portion 114 to incline together with the exercise machine while maintaining direct contact between elements of the exercise machine and the ground surface 118. One advantage of allowing load bearing elements of the exercise machine 101 to maintain contact with the ground surface 118 vs standing on a platform as in prior art is that the lower chamber portion 115 need not be designed to carry the load of the user 90 and exercise machine as a support surface 129, thereby allowing the design of the lower chamber portion to focus only on carrying the added load from the pressure and minimizing the structural requirements, cost, and complexity of the lower chamber portion. The design of the lower chamber portion 115 similarly need not worry about leveling or other such "ground interfacing" requirements of an exercise machine 101, further reducing part count, cose, manufacturing and installation complexity, etc.

Whereas prior art sought exclusively to build framing OUTSIDE of the exercise machine 101 footprint, this may be wasteful in space, material, cost, and increases substantially the footprint and volume enclosed by the chamber 300 and therefore the loads on the DAP unweighting system 100 from the chamber. Force is proportional to area over which pressure is applied $F=P\times A$, so a larger chamber volume means higher loads on all structural members 110. The smaller the chamber 300 footprint, the lighter duty the overall DAP unweighting system 100 can be made. Further, it is advantageous to construct the chamber 300 by contouring the shape so as to carry as much load internally via fabric wall stress as possible and this means creating as small a volume as possible without encumbering a user's 90 movement like arm or leg swing. As the contouring around the user is desired to be as tight to the body as possible, and the user's body is internal to the handrails 104, this necessitates that the upper portion of the chamber 300 be positioned and retained inside of the handrails as shown in FIG. 1A.

However, in the case of handrails 104 and FIG. 1A, forming a sealing surface 112 interior to the handrails 104 or smaller than the external perimeter of the exercise machine 101, as described in an alternate embodiment (see e.g., FIG. 12 and description below for Alternate Embodiment #2), may encroach upon the area designed for placement of body parts, such as feet landing locations, when not operating the exercise equipment 101. Therefore it may be optimal to dispose the sealing surface 112 outside of a handrails 104 for example, while simultaneously having a port assembly 131 as shown in FIG. 3A,B to allow the chamber to cross the handrail in order to reach and form a user seal 302 on the other side of the handrail 104 as shown in FIG. 1.

For reference, a user seal 302 is the portion of the DAP unweighting system 100 that allows for interfacing to the waist area of the user 90 to create a substantially airtight seal. One example of a user seal 302 is the zipper assembly of the AlterG P200 disposed around a hole in the top of the chamber 300, wherein the zipper is configured to receive a mating zipper on a pair of neoprene shorts worn by the user 90. The mating shorts comprise an interfacing skirt with a perimeter matching the perimeter of the hole in the chamber 300 and the skirt covers any additional area not taken up by the user 90 such that when the shorts are connected to the chamber 300 via the zippers, the entire area of the hole is plugged shut to maintain a substantially airtight environment inside the chamber. Many such user seals 302 are disclosed in prior art DAP unweighting systems and patent applications and the reader shall understand that these concepts may be similarly adapted to the applicant's invention to comprise a user seal as employed by the applicant in this specification.

Further, consoles and displays in prior art were also custom designed and only the exercise machine base 144 assembly of treadmills in the case of AlterGs M320, P200, and Sasta Fitness of a previously designed exercise machine 101 was used. To minimize part count and redundancy, it may be ideal therefore to leave handrails 104 and console support members 109 intact and seal around these elements (ideally without disconnecting them). Port assemblies 131 therefore can play an important role in adapting an unweighting assembly 102 to an exercise machine 101 to convert it into a DAP unweighting system 100, by allowing the sealing surface 112 and the user seal 302 to be on opposite sides of existing exercise machine frame elements 103 and/or console support members 109 such as handrails 104 and console stanchions.

Additionally, the ports and/or port assemblies 131 may be increased in number such that some are used and some are unused depending on the model of exercise machine 101 the unweighting assembly 102 is adapting to. In case certain port assemblies 131 are unused, they may be sealed with hose clamps, plugs, tie wraps, or other suitable means of closing a hole in a substantially airtight manner. By including multiple port assemblies 131 on a chamber 300, a single chamber may be made adaptable to several different exercise machines 101. This would be done for example by multiplying the port assemblies 131 as shown in FIG. 3A, and creating a pattern designed to provide a wide range of options for different models of exercise machines 101 wherein appropriate port assemblies would be used for a given exercise machine 101 and the other remaining port assemblies would go unused and sealed substantially airtight. The reader shall generally understand the concept and additional figures omitted in the sake of brevity.

Port and port assemblies 131 may be located on the upper chamber portion 114, lower chamber portion 115, or both and may pass a myriad of elements between the inside and outside of the chamber 300. In the case power or data cables are passed through the chamber 300, a suitable port assembly 131 design may be a conical or cylindrical sleeve with a removable internal plug 132 (not shown). The plug 132 may comprise a rubber, foam, or other suitable sealing-friendly material formed in a suitable shape such as a cylindrical or truncated cone shape. The plug 132 may have a hole from one end face to the next for passing the cord through, and may be slit along the length from an outside surface through the wall and reaching the hole to form a clam shell configuration for insertion of a cable. In such a manner the plug 132 may be opened by opening the slit in order to insert the cable, and may then be closed and clamped inside the sleeve with a hose clamp or suitable fastener. Multiple holes may be provided in the plug 132 in the case of multiple cables needing to run through a single plug, and unused holes may be individually plugged. The reader shall note there are many ways to pass members in and out of a chamber 300 and the port or port assemblies 131 may be adapted in a variety of ways to achieve this function. The applicant's invention therefore shall not be limited only to the methods and constructions described herein when it comes to passing objects from inside to outside the chamber 300.

The chamber 300 is preferably connected to the sealing surface 112 as described previously and in the preferred embodiment the upper chamber portion 114 and lower chamber portion 115 are clamped independently via two sets of chamber retaining members 113 depicted as rectangular tubing in FIG. 3B. Further alternatives are discussed in the alternate embodiments.

The chamber 300 may be provided with one or more windows (not shown) for viewing of the internals of the system, and for example, watching a user's 90 legs moving to analyze movement form. The windows may be provided on the sides, front, rear, or top of the chamber 300 and many examples are evident in the prior art. The shape and material of the windows may augment visibility or folding of the chamber 300 as well, or additional members such as plates or rods may be removable or permanently attached in order to facilitate folding as described in the prior art.

Figure 8:
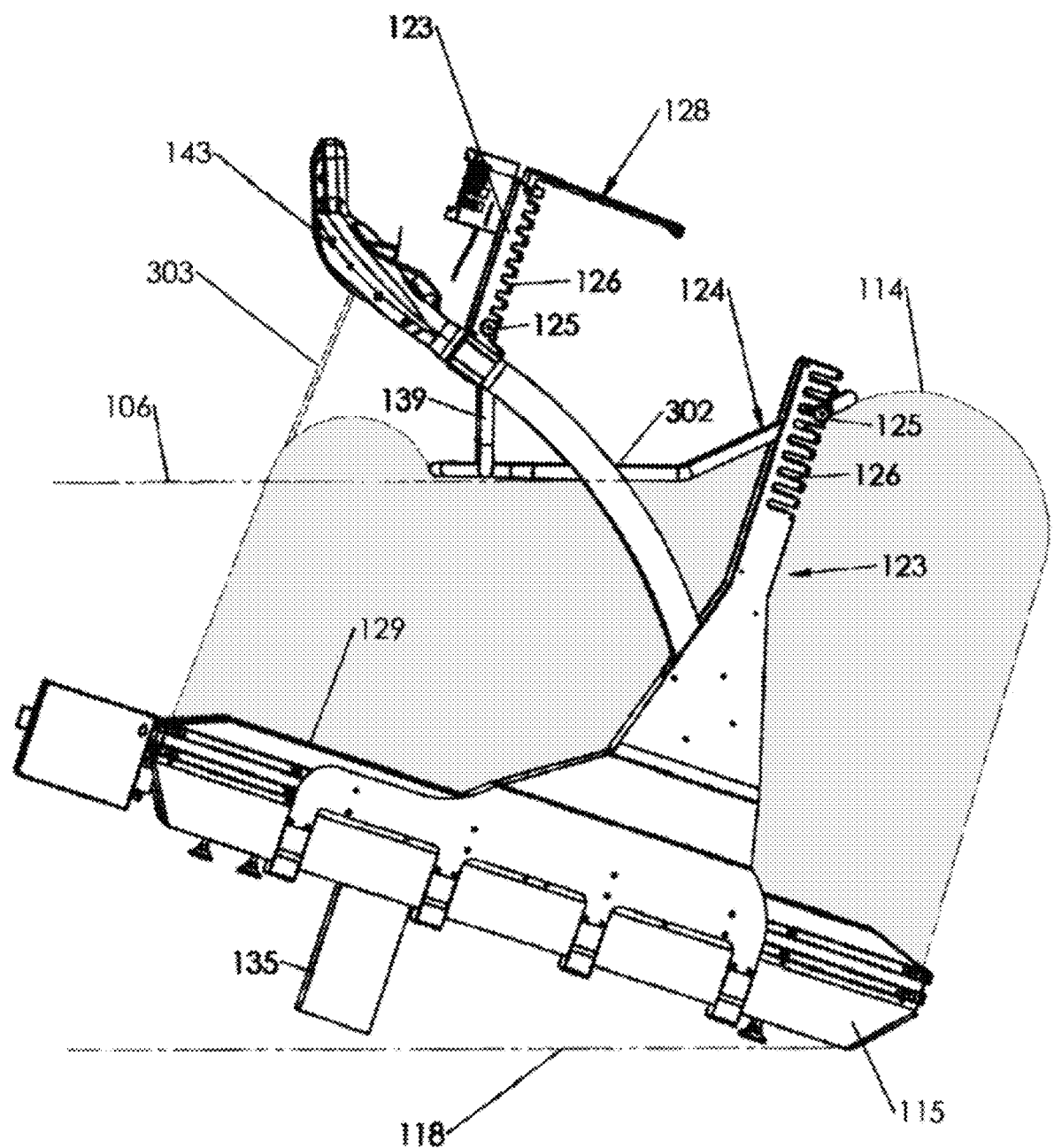
FIG. 8—Shows a side view of the DAP unweighting system adaptable to maintain seal orientation when the exercise machine is inclined by altering the slot alignment into which the seal frame is placed, and how the chamber conforms to the seal frame and bubbles up but does not interfere with user movement.

The chamber 300 may have sleeve provisions for attaching, either permanently or removably, to a seal frame 124, existing exercise machine frame element 103, such as a handrail 104, or other member of the DAP unweighting system 100. A sleeve element (not shown) may allow for securing of a portion of the chamber 300 in a specified position, orientation, or shape to facilitate ingress and egress, or user comfort during operation, protect windows from excessive folding, or otherwise improve the function, reliability, cost, or look of the DAP unweighting system 100. Sleeve options are known and described in the prior art such as the AlterG P200, and all such variations may be applicable to the applicant's invention. A sleeve element may grip tightly to a member of the DAP unweighting system 100 so as to reduce or prevent slippage, or may be designed to slide, for example along a handrail 104, to facilitate collapsing of the chamber 300 during ingress or egress. Gripping or sliding may be achieved via dimensions of the sleeve element or simply the material properties of the sleeve element and their coefficient of friction against the surface to which they are encompassing. Chamber support members 303 such as cabling, webbing, or other material are shown in FIG. 8 and may be attached to the chamber 300 as well as elements of the DAP unweighting system 100. For example a console or an external gantry as shown in FIG. 8 may comprise a section of webbing between a front area of the upper chamber portion 114 and the use of this webbing may be to maintain a minimum height from the support surface 129 of the front area of chamber 300 when uninflated for example to prevent the folding of front or side windows (not shown). The chamber support members 303 may be flexible and move with the chamber during inflation without adding stress and therefore serve as passive elements during inflation while helping to shape or position sections of the chamber 300 appropriately when pressure is removed. The chamber support members 303 may be permanently connected to the chamber 300 or may be removable and may be shortened or lengthened to move the chamber into an appropriate position when uninflated. The chamber support members 303 may similarly be removable or permanently connected some portion of the frame of the DAP unweighting system 100 such as the exercise machine console 143 in FIG. 8.

The chamber 300 has a user seal 302 for sealing to a portion of the body of a user 90 and many examples of user seals are known in the prior art and may be applied to the applicant's invention as described above. The user seal 302 may further be attached directly to a user's body, for example a permanent garment sewn into the chamber, or may allow for insertion of custom garments or attachments that create an intermediate interface between the user seal 302 and the user's 90 body. Such intermediate interfacing methods and designs are similarly known in the art and may be adaptable for use with the applicant's invention. A user seal 302 may be removable via suitable means such as a zipper or other fastener as previously described. The fastener may itself be substantially airtight or may be accompanied by suitable sealing assembly 136 such as described herein or described via prior art.

In regards to the sealing the chamber 300 to the sealing surface 112, the chamber 300 may incorporate rods, bungee cords, or other physical barriers that assist in preventing the chamber from moving past the chamber retaining members 113 when pressurized, and enforce a good seal without putting undue stress for example on hole cutouts 301 in the chamber as shown in FIG. 3A,B. Such mechanisms are similarly described in the prior art.

The lower chamber portion 115 may be flexible or rigid and advantages have been previously discussed regarding a flexible material. An additional advantage to a flexible lower chamber portion 115 is in accommodation of an incline assembly 134 of an exercise machine 101, for example a treadmill as shown in FIGS. 6, 7A-C, 8. An incline assembly 134 can either be sealed entirely within one or more chamber compartments 133 of a lower chamber portion 115 such as in FIG. 7A, or may partially protrude through the one or more chamber compartments of the lower chamber portion such as in FIG. 7B,C. Typically, the incline assembly 134 is either a rack and pinion style or leadscrew/linear actuator driven. If the lower chamber portion 115 is rigid, it is likely the incline assembly 134 needs to be removed from the exercise machine 101 in order to attach the lower chamber portion 115 to the exercise machine, and this adds unnecessary and cumbersome work, particularly in the case of a field upgrade. A flexible lower chamber portion 115 by contrast can be created in a much easier way by incorporating one or more chamber compartments 133 to encompass an incline assembly 134 as shown in FIGS. 6, 7A-C, 8.

Figure 7A:
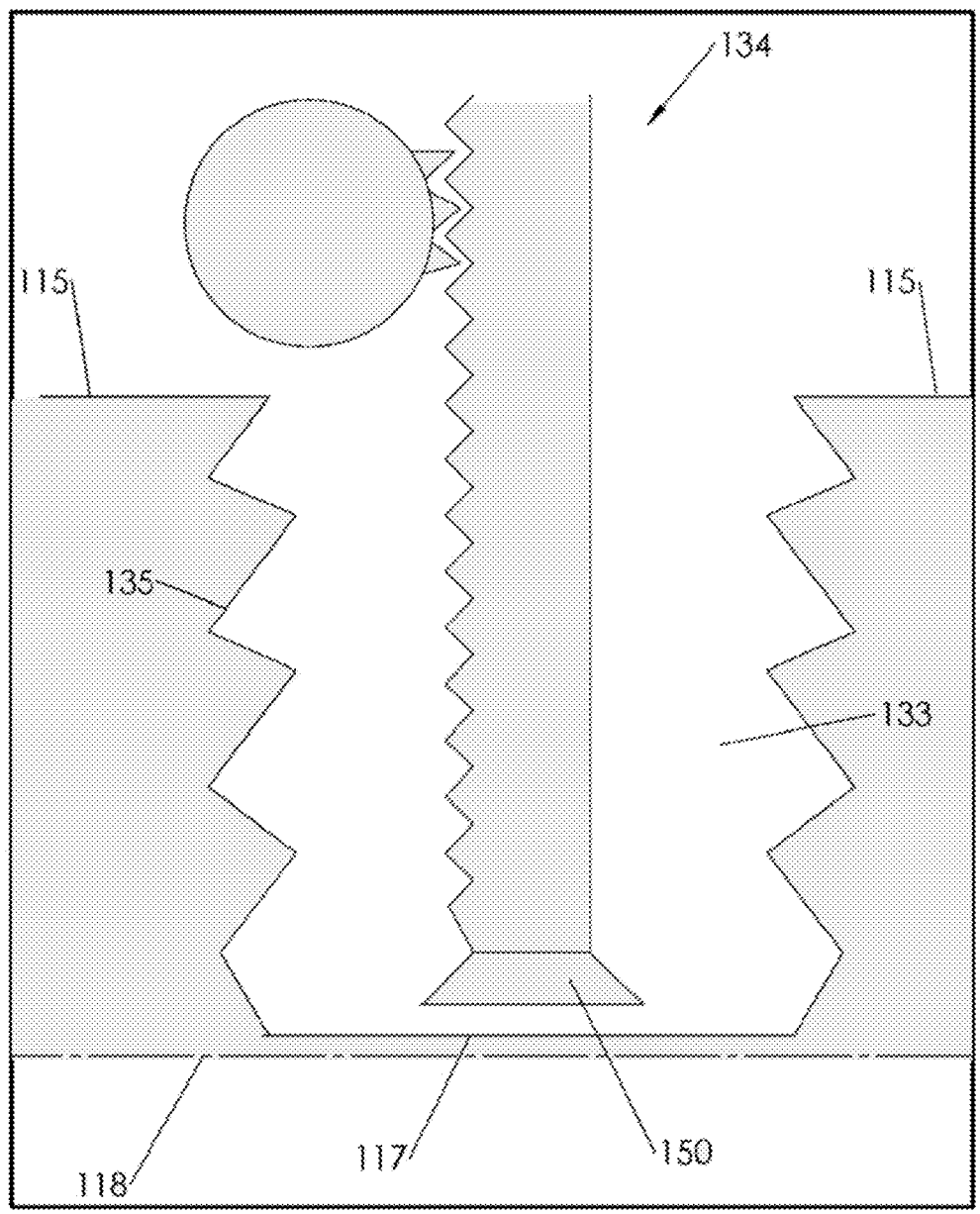
FIG. 7A—Shows a chamber compartment for accommodating a rack and pinion style incline assembly of the exercise machine.

FIG. 7A shows a cut view of a flexible lower chamber portion 115 with a chamber compartment formed as a bellows 135 segment that allows extension and retraction of a rack and pinion style incline foot 150. The bellows 135 may be integrated into the lower chamber portion 115 or may be positioned for example inside a cylindrical chamber compartment 133 which is part of the lower chamber portion 115. In either case, the bellows 135 element assists in the collapse of this section of the lower chamber portion 115 and keeps the fabric of the lower chamber portion away from the rack and pinion mechanism which could damage the fabric and did so in fact during prototyping of this concept. The reader shall note that a rigid lower chamber portion 115 could also be used in this situation with a bellows 135, or chamber compartment 133 housing a bellows, connected to the bottom of the rigid lower chamber portion, and this configuration may function similarly to the flexible option. However other disadvantages with a rigid lower chamber portion 115 as previously described such as shipping bulk and assembly difficulty remain. It is much easier for example to place a fabric lower chamber portion 114 around an exercise machine 101 than to drop the exercise machine into a rigid lower chamber "basin" and attach the basin to the exercise machine to accommode incline, etc. The reader shall also note that the incline foot 150 may stay within the bellows 135 or chamber compartment 133 housing the bellows, and sandwich the lower chamber portion 115 between the incline foot and a ground surface 118 as shown in FIG. 7A, or the incline foot may protrude through the bottom surface 117 of the bellows 135 element and rest directly on the ground surface 118. This second option may provide an advantage that the weight of the exercise machine 101 and user 90 is not crushing the fabric against the ground surface 118, which may reduce life expectancy. Other methods of accommodating incline assemblies 134, and in particular pivoting leadscrew style assemblies are described in alternate embodiment.

Unweighting Assembly—Chamber Retaining Struts & Intermediate connecting member

Figure 6:
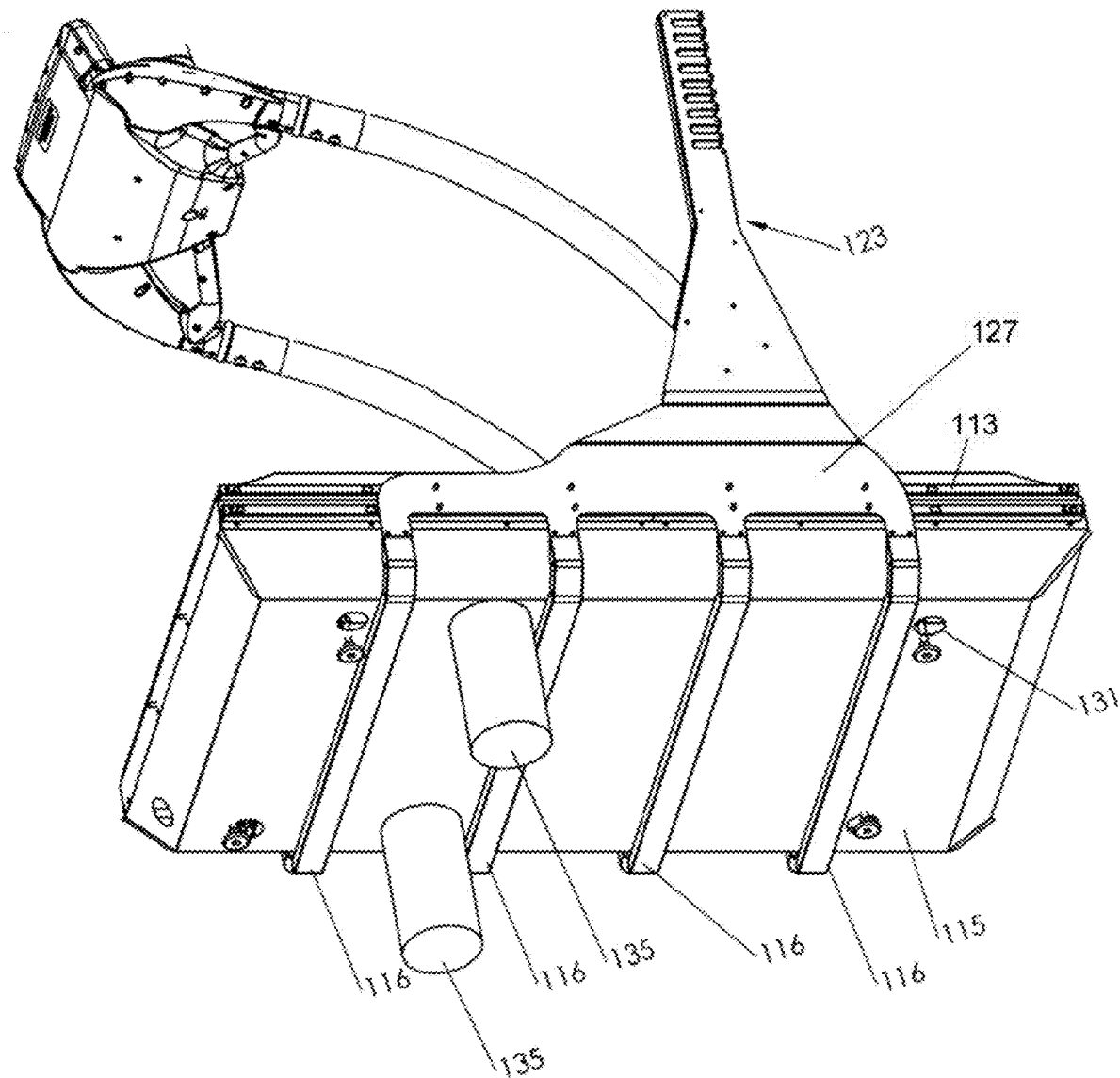
FIG. 6—Shows a plurality of chamber retaining struts for limiting expansion of a lower chamber portion towards the ground surface.

The lower portion of the chamber 300 may be further restrained by one or more chamber retaining struts 116 as called out in FIGS. 1A, 6. The chamber retaining struts 116 may be placed relative to the exercise machine 101 in a transverse and/or longitudinal direction or a combination of the two. The chamber retaining struts 116 are shown in FIG. 6 as rectangular sections of tubing, but may be any size, shape, wall thickness, material etc that satisfactorily support the lower chamber portion 115, and may be made of steel, aluminum, carbon fiber or any suitable material. The lower chamber portion 115 may be kept off the ground surface 118 by the chamber retaining struts 116 entirely or may be allowed to touch the ground surface 118 to some extent without detracting from the purpose of the chamber retaining struts 116. The reader shall not that if the lower chamber portion is rigid the chamber retaining struts 116 may not be required and therefore shall be considered optional.

The chamber retaining struts 116 may similarly be straight in shape or may be curved, mounted on an angle, or otherwise modified to adapt to the shape of the underside of the exercise machine 101 and in particular avoid contacting leveling or mounting feet, and electronics, and incline assemblies, or the running surface as it goes around the bottom of the exercise machine in the case of a treadmill. The chamber retaining struts 116 may also be interconnected to provide additional support and prevent the lower chamber portion 115 from going lower, close to the ground surface 118. The chamber retaining struts 116 may be coplanar or staggered to conform better to the expected inflated shape of the lower chamber portion 115.

The chamber retaining struts 116 may connect to an intermediate connecting member 127 as shown in FIG. 6, and the intermediate connecting member may connect to a structural member 110 (any element in the DAP unweighting assembly that supports load of any kind shall be considered a structural member in the context of this application). Connection to the intermediate connecting member 127 may be via bolt, clasp, hook, or other mechanical interference or otherwise known by those skilled in the art. The intermediate connecting member 127 may connect to the chamber retaining members 113 as shown with nuts, bolts, etc. or may connect directly to a height adjustment post 123 (the height adjustment post shown in FIG. 1 for example) without connecting to the chamber retaining members as shown in FIG. 1. Connection to a height adjustment post 123 has the benefit of taking advantage of the rigidity of structural members 110 such as handrails 104 carrying the load internally in tension/compression instead of, or in addition to, the chamber retaining members carrying load in shear and bending. Tension/compression is a more efficient way for structural members to carry load vs. bending or shear.

As the chamber 300 is inflated, the lower chamber portion 115 bulges and tries to move vertically downwards relative to the exercise machine 101. The chamber retaining struts 116 limit this expansion and therefore keep the lower chamber portion from contacting the ground surface 118 sufficiently to lift the exercise machine 101 off the ground surface, which happened during prototyping. The surface area can be quite large so it doesn't take very much pressure to produce several hundred pounds of force and lift the exercise machine 101 off the ground surface 118. The chamber retaining struts 116 transfer this load efficiently in tension to the intermediate connecting member 127, which in turn transfers this load in shear to either the chamber retaining members 113, in tension/compression to the height adjustment post 123, or both. In so doing, the forces are carried efficiently internally and no net vertical force is applied to the exercise machine 101.

The reader shall note that the intermediate connecting member 127 may be eliminated and integrated into the height adjustment post 123. It may be more convenient to keep this as a separate piece however to facility assembly and size of shipping package. The intermediate connecting member 127 may be configured to mount electronics or other components used in the DAP unweighting system 100 as well, or may be configured to form the shape of a support surface 129 for sitting or standing either by the user 90 or a bystander. The intermediate connecting member 127 may be sheet metal or other structural material suitable for carrying the applied load and may be shaped in any form that is for carrying the load. A support surface 129 in the context of this invention is any surface that a supports the weight of a user 90 or bystander, for example a treadmill running surface, a chair, a bicycle seat, etc.

Unweighting Assembly—Height adjustment posts & Seal Frame

It is an important function for the usability of the DAP unweighting assembly 100 that it be capable of adapting to users of different body types, in particular height. If a height is not set in a reasonable vicinity of the user's 90 waist, the user seal 302 can bubble up and be uncomfortable. If the height of the chamber 300 is too low relative to the user's 90 body, then the user may contact the chamber or a seal frame 124 for example with their knees or heels.

Figure 4A:
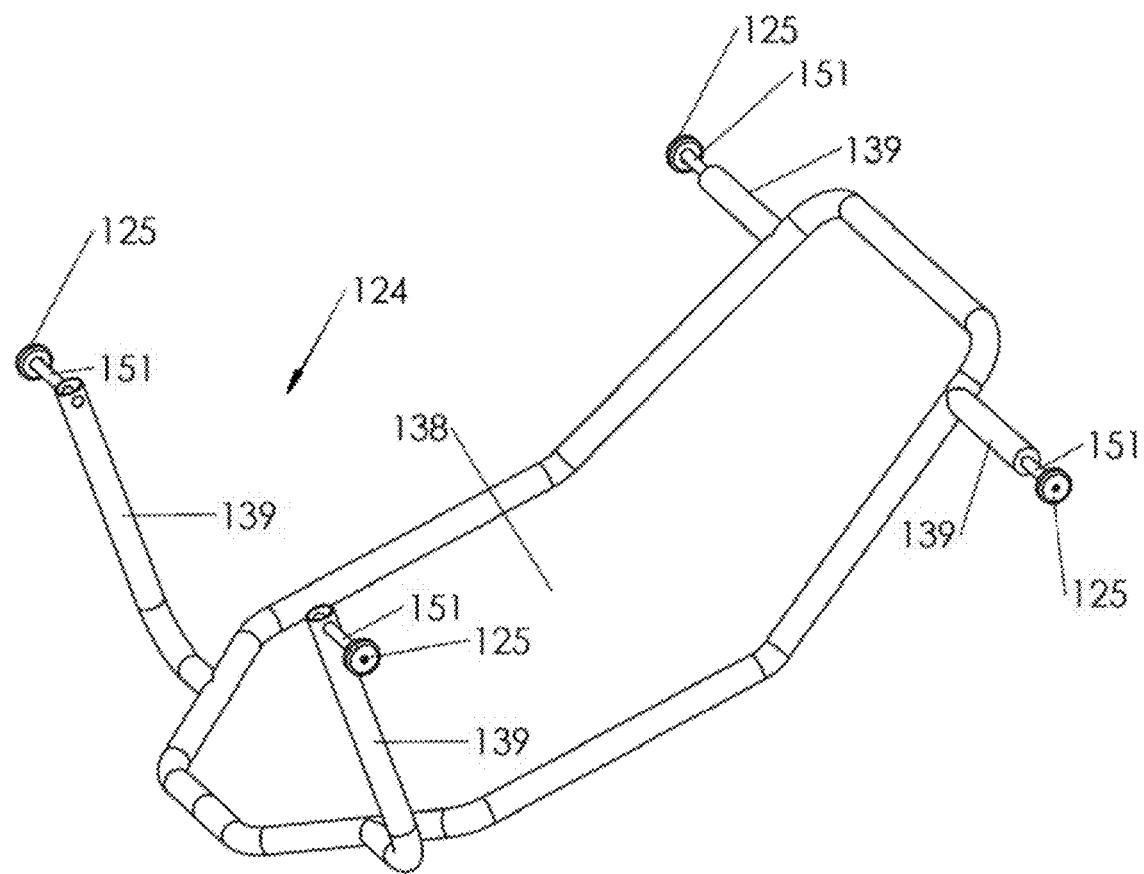
FIG. 4A—Shows one variation of a seal frame adapted for limiting an upper height of a chamber, the seal frame comprising seal frame struts and locking pegs for positioning in height adjustment slots on matching height adjustment posts (not shown), and retaining elements for containing load efficiently.
Figure 4B:
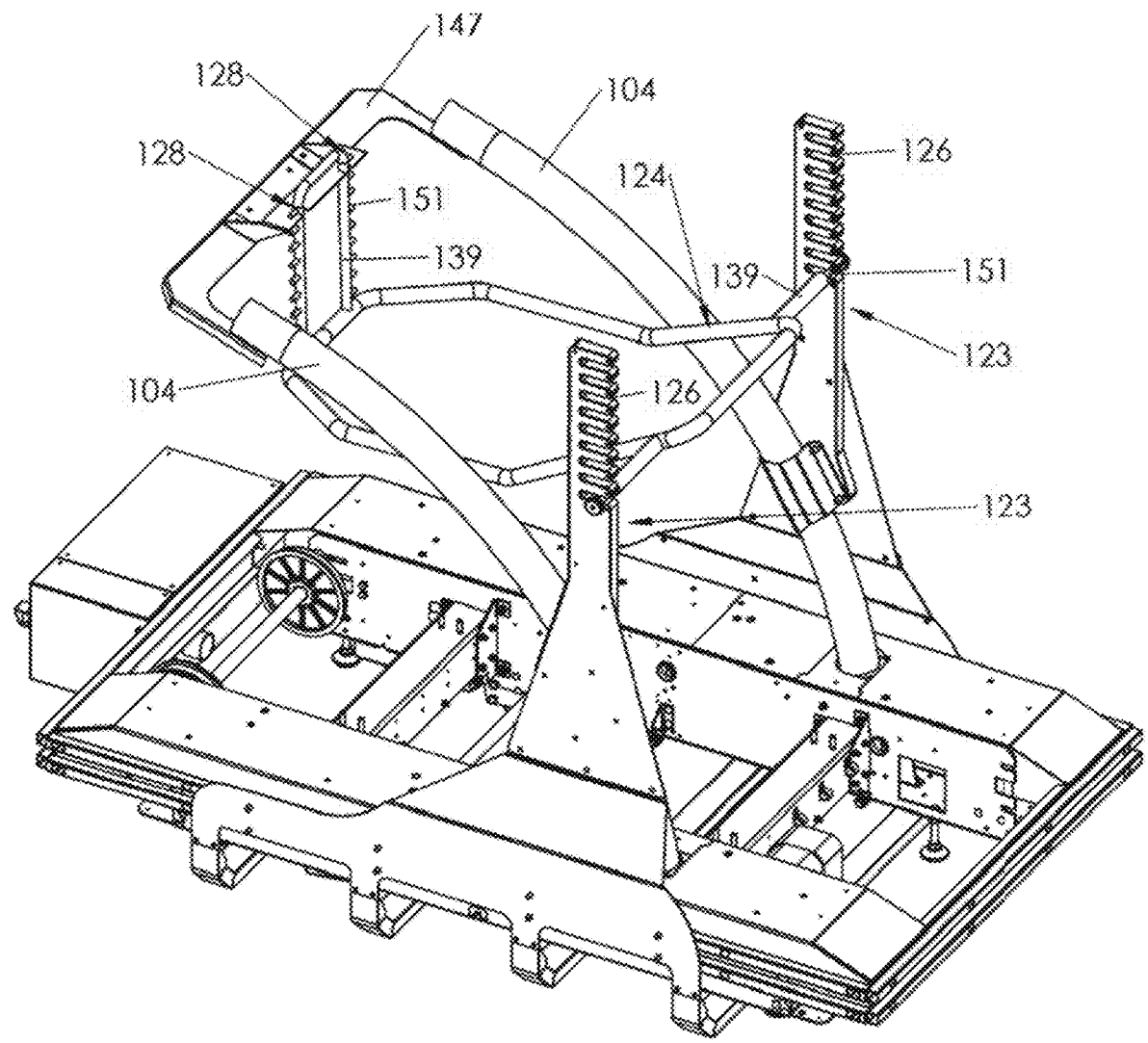
FIG. 4B—Shows an alternate variation of a seal frame adapted for limiting an upper height of the chamber including a lateral reinforcement member spanning two curved handrails of the exercise equipment, and height adjustment posts in the rear, wherein the seal frame is in communication with the rear height adjustment posts and the lateral reinforcement member to maintain its position relative to the exercise machine. The console of the exercise machine is not shown for sake of clarity.

Prior art has described an efficient height adjustment mechanism incorporating four height adjustment posts 123 with each post having height adjustment slots 126, and a free floating seal frame 124 with pegs 151 that fit in those slots as a mechanism for setting an upper limit on chamber height 106 as shown in FIGS. 4A-B,8. FIG. 4A shows a seal frame 124 comprising four seal frame struts 139, which extend away from a loop 138 formed around the user 90 and the four seal frame struts have pegs 151 with external retaining members 125 in the form of plastic "ears" which limit the height adjustment posts 123, particularly in the rear, from splaying further outward under pressure from the chamber 300.

Figure 9A:
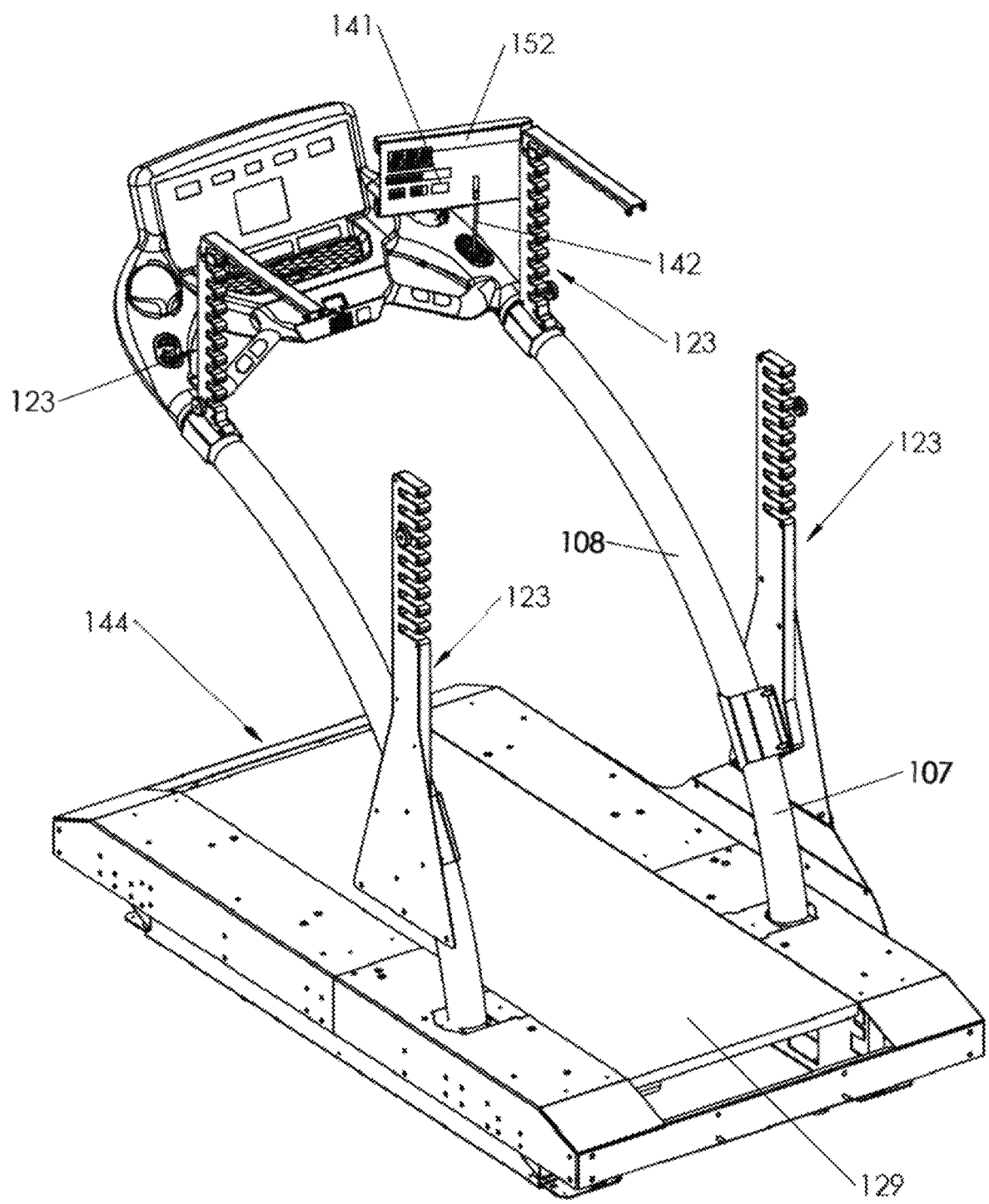
FIG. 9A—Shows front and rear height adjustment posts adapted to an exercise machine for securing a seal frame.

The applicant's height adjustment scheme as shown in a majority of the figures is similar to that of the AlterG's P200. A plurality of height adjustment posts 123 are disposed around the exercise machine 101. The height adjustment posts 123 may be located on top of (as shown in regards to the front height adjustment posts), exterior to (as shown in the rear height adjustment posts), or interior to (not shown) an existing exercise machine frame element 103, such as handrails 104 as shown in FIG. 1A,9A. The location of the height adjustment slots 126 and height of the height adjustment posts 123 may be customized to the expected users 90 height and the reader shall note that height adjustment slots are also but one height adjustment scheme proposed in the prior art and that many such schemes may be adapted to the applicant's invention.

The height adjustment slots 126 in the height adjustment post 123 of FIG. 1A may be long enough such that the seal frame 124 may be placed in a height adjustment slot that corresponds to a tilt angle of the seal frame relative to the support surface 129 for the user. By allowing for the seal frame 124 to be angled relative to the support surface 129, when the DAP unweighting system 100 is inclined, the seal frame may be moved and angled relative to the support surface such that the user seal remains substantially parallel with the ground surface 118, as shown in FIG. 8, while at the same time maintaining its nominal distance from the support surface so that the degree of unweighting remains substantially consistent. As described elsewhere in this application, if on incline of the exercise machine 101, the seal frame 124 is also inclined relative to the ground surface 118, then the unweighting force becomes non-parallel with the force of gravity and may lead to alteration of gait. If, as in prior art, the seal frame 124 remains parallel with the ground surface 118 while the support surface 129 is inclined, then the user 90 is pushed up or down relative to the seal frame and the degree of unweighting is also altered. This is one disadvantage of prior art designs for chambers 300 and height adjustment posts 123 that are not connected integrally with the exercise machine 101, is that the geometry changes as the exercise machine is inclined and this impacts the utility of the system. Again, this is because the seal frame 124 is fixed in space, but the location where the user 90 is standing is moving up and down relative to the seal frame and the unweighting dynamics of the user seal 302 are altered. In the applicant's invention, the length of the height adjustment slots 126 therefore may be long enough such that the fixed length of the seal frame 124 may be placed into different combinations of height adjustment slots so as to allow the seal frame to angle relative to the support surface 129. Either both sets of height adjustment slots 126 may be lengthened or only one set may be lengthened. FIG. 1A shows that the front set of height adjustment slots is just long enough to accommodate the pegs 151 of the seal frame 124, whereas the rear height adjustment slots 126 are lengthened to allow the rear pegs to be placed higher or lower than "horizontal". The reader shall note that the larger the relative angle between the support surface 129 and the seal frame 124 desired, the longer the minimum length of the adjusting set of the height adjustment slots 126 should be.

The seal frame 124 is created such that a portion of the seal frame adjacent to the user may be substantially horizontal whereas another portion of the seal frame may be inclined in the front and/or back, FIG. 8 shows a back portion of the seal frame inclined, to in the form of a saddle-like shape. The reader shall note this is preferable, but is not a requirement and alternatively the seal frame 124 may be biased a downward sloping angle from back to front, or may be designed without an inclined portion at all. If a portion of the seal frame 124 is inclined, the inclined section may allow for an efficient running envelope where the arms may swing freely along the sides and the knees and feet can move freely in the front and rear. The seal frame 124 may also be in communication with the chamber 300 through sleeve elements as discussed earlier and in prior art, which may act to limit a maximum chamber height 106 of a top surface of the chamber, in the vicinity of the user seal 302, where the maximum chamber height is determined by the specific height adjustment slots 126 the seal frame is placed in as shown in FIG. 8. The reader may refer to prior art examples and discussions of seal frame 124 connection methods to the chamber 300 and how this adjusts the chamber height 106.

Figure 4C:
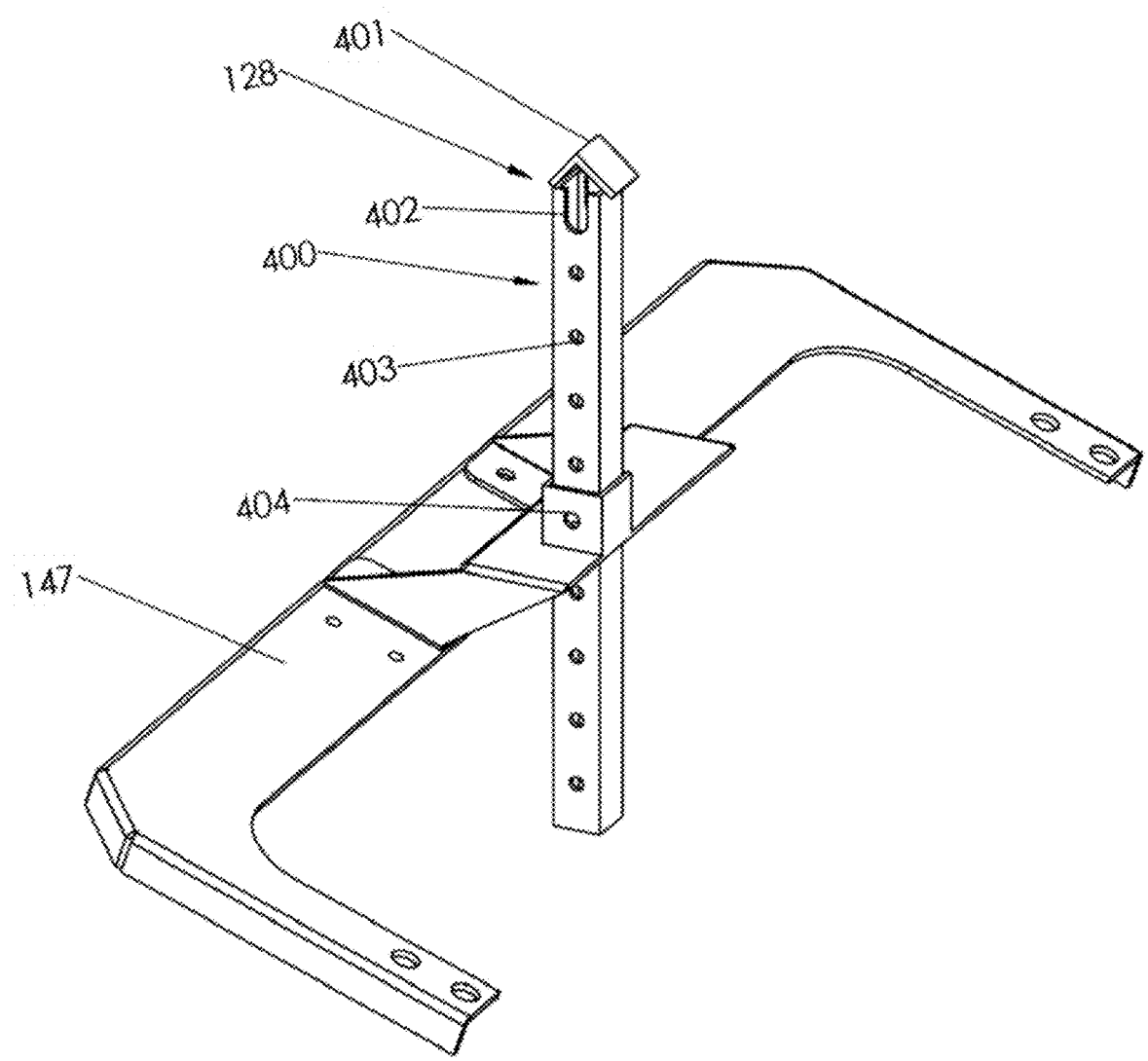
FIG. 4C shows an alternate height adjustment scheme for simplifying the setup process and ingress with a height adjustable latching mechanism.

The height adjustment posts 123 may be in communication via attachment means with, but not limited to, one or more existing exercise machine frame elements 103, console support members 109, structural members 110, or additional frame members 111 for example a handrail 104 of the exercise machine 101 as shown in FIG. 1A, or the handrail 104 and console support members 109 of the existing exercise machine 200 in FIG. 2A,B. Suitable attachment means may or may not use existing hardware of the exercise machine 101, and may be clamped, screwed, glued, welded, or otherwise attached via methods known to those skilled in the art. Important aspects are that the height adjustment posts 123 are rigidly fixed and can carry the load applied by the chamber 300 in the vertical and lateral directions when the chamber is inflated. A seal frame 124 is disposed and in communication with an upper chamber portion 114 so as to limit a chamber height 106 of the chamber when the seal frame is placed in communication with height adjustment slots 126 on the height adjustment posts 123. A latching mechanism 128, as shown in FIG. 4B-C,8 may be disposed in order to lock the seal frame 124 into a specific height adjustment slot 126 as determined by the user 90. The latching mechanism 128 may be removable such that the position of the seal frame 124 may be easily changed by the user 90. The height adjustment posts 123 may be disposed in the front, rear, or side of the user 90 by example. A latching mechanism 128 may be disposed in the front, rear, or side of the user 90, or only in front of the user as shown in FIG. 1A,8. Latching mechanisms 128 are depicted in prior art and generally known by those skilled in the art, and depicted in FIG. 8 as the gate-latching mechanism with locking pin similar to AlterG's P200.

Figure 9B:
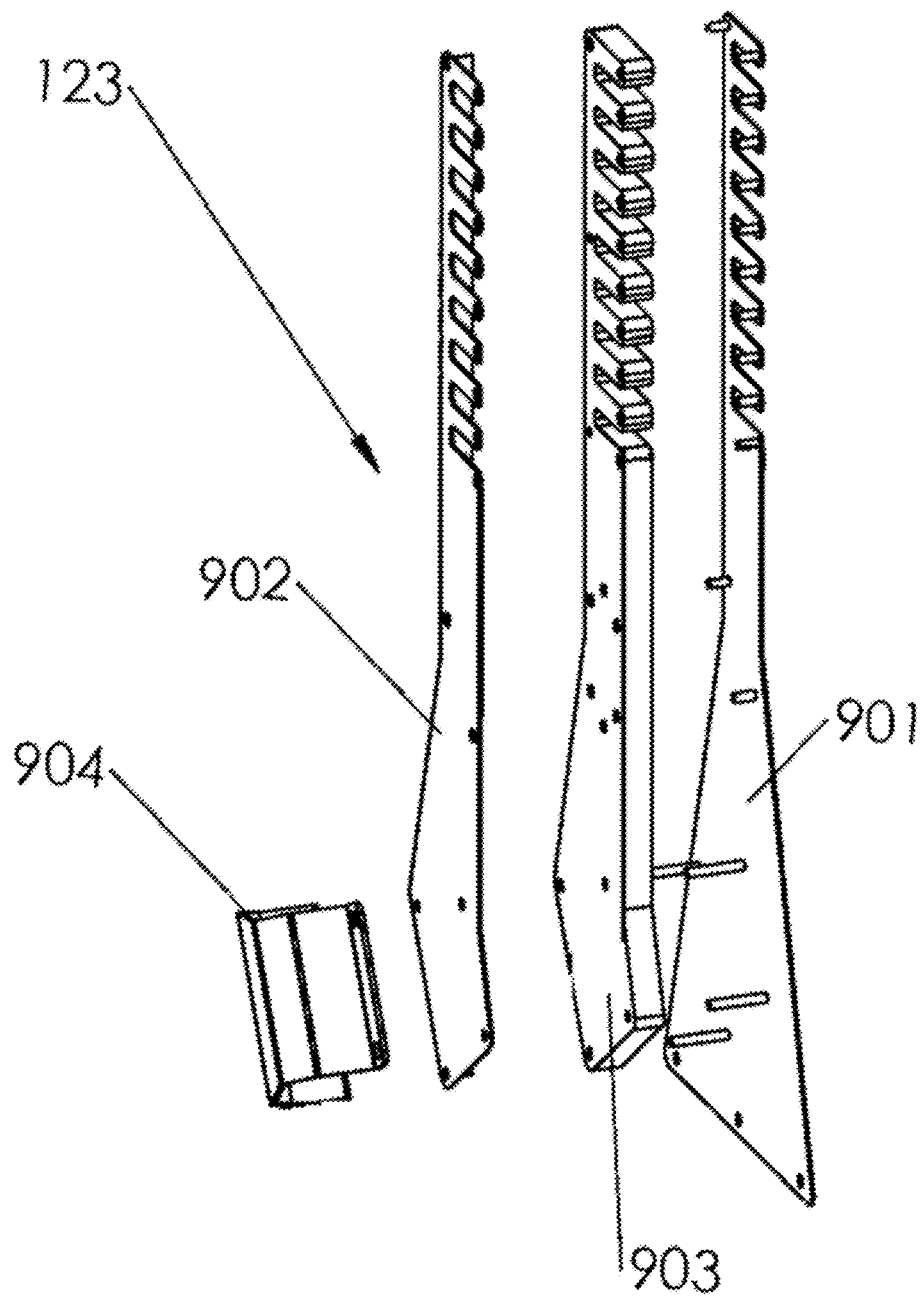
FIG. 9B—Shows an exploded view of the height adjustment posts of FIG. 9A.

The height adjustment post 123 may be made from an integrally formed component or may be a combination of components as shown in FIG. 9A-B. FIG. 9B shows an exploded view of one example of a rear height adjustment post 123 wherein an external height adjustment plate 901 and an internal height adjustment plate 902 sandwich a height adjustment latch 903, and this assembly is clamped to the handrail 104 of the exercise machine 101 with an internal clamp 904. The position of the rear height adjustment post 123 may be dictated by another element of the DAP unweighting assembly 100, such as additional frame members 111, or intermediate connecting member 127 as shown in FIG. 1A, or may be measured and clamped in place during assembly. As mentioned above, the height adjustment post 123, particularly in the rear, may be in communication directly with the chamber retaining struts 116, and via an intermediate connecting member 127 as shown in FIG. 6. Height adjustment posts 123 in the front may be of similar construction to the rear. The reader shall note that what is important is positioning the height adjustment slots 126 in space in the appropriate vertical and horizontal location to fit the seal frame 124 and desired height adjustment ranges, and any construction, material selection, combination of materials, etc. that can accomplishes this and can sufficient carry the applied loads is within the scope of this invention.

Whereas prior art sees the exercise machine base 144 (for example a treadmill) elevate relative to the seal frame 124, the applicant's seal frame maintains its separation distance relative to the running support surface 129 under incline. This goes back to the idea that the applicant's invention is building onto an exercise machine 101 instead of building around a portion of an exercise machine. One benefit of the applicant's invention is that the height of the seal frame 126 is maintained during incline. If the incline is sufficient to cause a noticeable change in direction of the unloading force due to tilt of the user seal 302, the user 90 may remove the seal frame from the applicant's design and replace it at an angle declined relative to the running support surface 129 such as shown in FIG. 8. This maintains the orientation of the user seal 302 parallel with the ground surface 118 and the unloading force parallel with the force of gravity so the unloading is as natural as possible. The applicant's invention therefore is able to maintain the most consistent level of unloading and maintain overall user height and elevation ranges, by maintaining the distance between the exercise machine 101 and the user seal 124, and simultaneously the most natural unloading force by keeping the unloading force parallel with the force of gravity versus the prior art.

Unweighting Assembly—Electronics

An electronics box 121, pressure, and regulation source (i.e. blower 119) may be supported by an element of the DAP unweighting system 100 as shown in FIG. 1A, for example by attaching to the chamber retaining members 113 in the front of the system. The applicant's invention shall not limit the electronics or pressure source to this location as shown, and it shall be well understood that such assemblies and components may be connected elsewhere by suitable means known to those skilled in the art.

A pressure source, for example a commercial blower 119, may be in communication with the chamber 300 directly or via an intermediate piping system (not shown). The pressure source may be regulated, for example via the speed of the motor, or may incorporate a regulating valve to regulate an intake or an outtake from the chamber. Many such systems have been covered extensively in prior art and shall not be repeated here. An electronics box 121 may serve as a support surface 129 for a user 90 or a bystander to sit or stand. In such a case the electronics box 121 may be designed with reinforcements or other means to carry such applied load. The blower 119 may be user-serviceable and separated from dangerous voltage areas, or serviceable only by a technician.

A display 152 may be provided at a location on the DAP unweighting system 100 that is convenient for a user 90 to reach. This may be for example, but not limited to, on one of the front height adjustment posts 123 as shown in FIG. 9A. The display 152 may be fixed or may be movable and may be switched from the right side as shown to the left side. The display 152 may include one or more input mechanisms 141, for example buttons, which allow a user 90 to communicate with the system to enter data, change display settings, or otherwise operate the DAP unweighting system 100 in some manner. Display 152 means may include LCD displays, segmented LED displays, touchscreens, or other display means know to those in the art.

Figure 11:
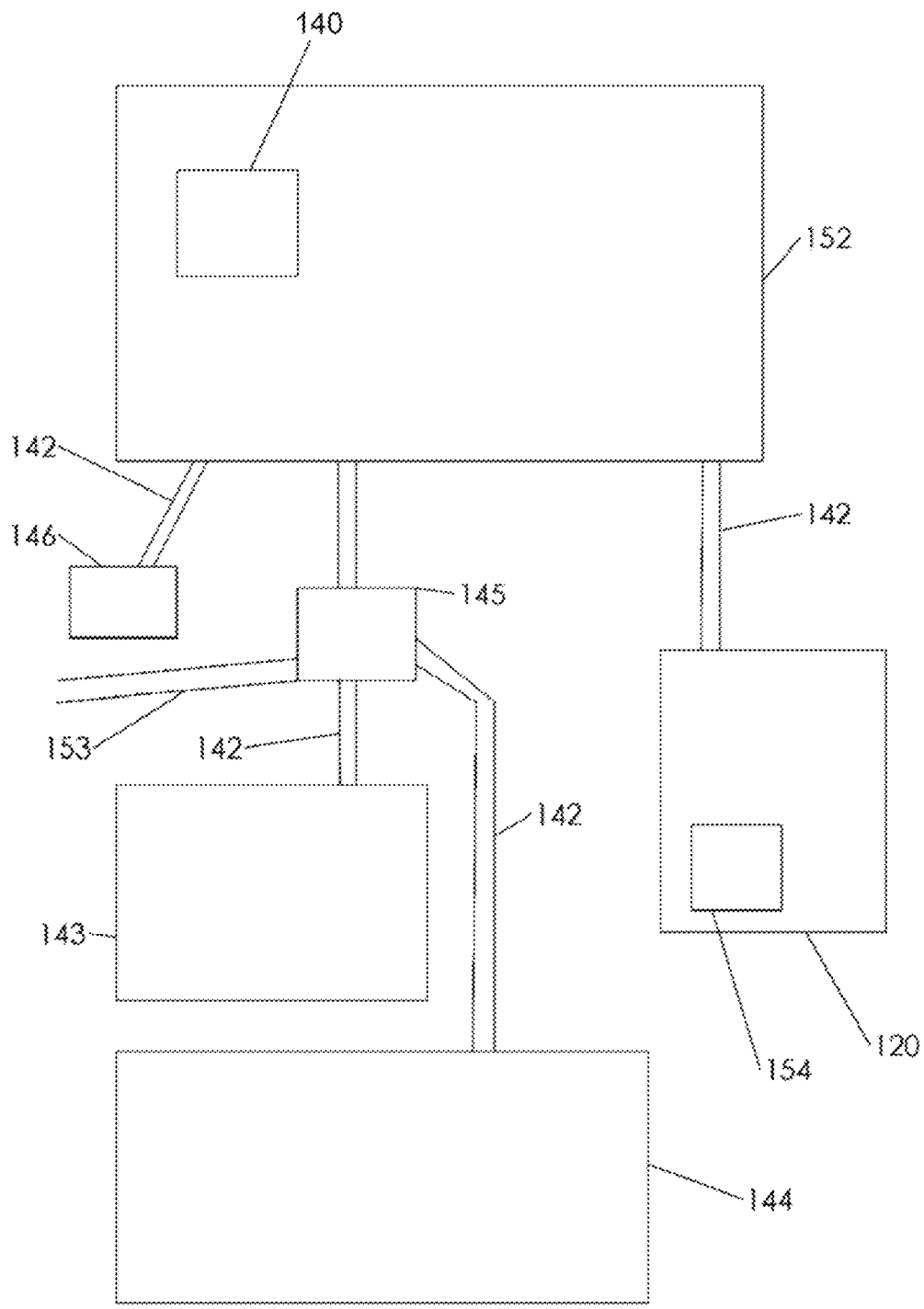
FIG. 11—shows a wiring diagram of a combined unweighting assembly and exercise machine electronics wherein an intercept assembly controls at least one of power or signal for the exercise machine to operate until the unweighting system determines it is safe to do so.

An electrical signal cable 142 carrying power or communications may run from the display 152 to blower controller 120, which serves as a pressure controller for the pressure source. The reader may reference the wiring diagram in FIG. 11 for electrical connection options. This electrical signal cable 142 may run down through an existing exercise machine frame element such as a hand rail as shown in FIG. 9A, pass through the chamber 300 via a port assembly 131, or run external to the chamber, or otherwise connect the display 152 with blower controller 120 as shown in the wiring diagram of FIG. 11. A pressure sensor 154 may be disposed inside or outside of the chamber 300 and the pressure sensor may be in communication with a blower controller 120 as shown in FIG. 11, or a processor 140 controlling the display and communicating with the blower controller. Alternatively the DAP unweighting system 100 may not incorporate a pressure sensor 154 and may simply control the pressure source, eg the blower 119, and regulate based of preset values for the pressure source and/or regulating valve if provided. Additional wireless functionality and data communications functionality may be built in to allow for remote diagnostics of the system or over the air updating of the firmware, or other programming or data communication between the DAP unweighting system and the outside world. Such communication means are generally known in the field of the internet of things (IoT) and shall be incorporated herein by reference.

An exercise machine 101 generally has an electrical signal cable 142 from an exercise machine console 143 to an exercise machine base 144 as shown in FIG. 2A,B. The electrical signal cable 142 may carry AC power, data signals, low voltage power, etc. It is important for safety that the unweighting assembly 100 be capable of determining when the exercise machine is allowed to function. For example if the chamber 300 is not inflated, it may be unsafe to allow a treadmill belt to move as it could cause a tripping hazard. As the applicant's invention is meant to work in tandem with a variety of exercise machines, it is beneficial to have a universal means to do this for all systems. To this end, the applicant has invented an intercept assembly 145. The intercept assembly 145 is a combination of connectors and electronics that is adapted to intercept one or more of the electrical signal cables 142 from the exercise machine base 144 before it goes into the exercise machine console 143. The intercept assembly 145 may also be configured to intercept the power cable going into the exercise machine 101 as one option and the intercepting of the power cable and electrical signal cable 142 may be done together or in part. Therein the reader shall understand the purpose of the intercept assembly 145 is to intercept any electrical signal cable 142 that serves the function of allowing the unweighting assembly 102 to prevent the exercise machine 101 from operating until it is safe to do so and this cable need not necessarily be directly between an exercise machine base 144 and exercise machine console 143.

The intercept assembly 145 is in communication with the processor 140 on the unweighting assembly 102 through the display 152, and the processor may decide to prevent signals on the electrical signal cable 142 to pass from the exercise machine console 143 to the exercise machine base 144 and vice-versa until the processor determines it is safe to do so. Similarly as shown in FIG. 11, the processor 140 may control the intercept assembly 145 through the display 152 to determine when power is enabled to the exercise machine 101 such that the exercise machine is powered off until the unweighting assembly 102 is in a safe state to operate the exercise machine 101. The intercept assembly 145 may be integrated into a PCB as part of the display 152 on the unweighting assembly 102, or may be a separate PCB as shown in FIG. 11, or even cable wiring harness that is comprised of connectors and appropriate relay or switching circuitry or to perform the controls described. The intercept assembly 145 may intercept all conductors/signal wires, or only enough so as to prevent operation of the exercise machine without permission from the processor 140 of the unweighting assembly 102. The intercept assembly 145 may optionally also intercept a signal from an emergency stop sensor 146 for communication of an emergency stop event from the exercise machine to the processor 140 of the unweighting assembly 120. Additionally, the intercept assembly 145 may have provisions for driving signals to the exercise machine console 143 such as the signal from the emergency stop sensor 146. In so doing the unweighting assembly 120 may communicate emergency events to the exercise machine 101 and vice versa. The intercept assembly 145 therefore allows simple universal safety controls between the unweighting assembly 102 and the exercise machine 101, which means that existing exercise machines 200 can be used along with their exercise machine consoles 143. This allows existing exercise machine frame elements 103 such as handrails 104 in FIG. 2A which support the exercise machine console 143, as well as console support members 109 like the stanchions of FIG. 2B to be used as intended and reduces the overall bulk and complexity of the combined DAP unweighting system 100.

Alternatively the electronics and wiring of the exercise machine 101 may be removed and replaced, or programming code instructions updated so that the system acts and behaves as an integrated design and appropriate signals and sensors are passed between these new electrical components and processors to maintain a safe operation for the user 90. Therefore the readers shall note, that the interface assembly is not a required feature of the applicant's invention, but may offer advantages in terms of simplified development cost, reduction of software updates and upgrading and overall complexity in putting an exercise machine 101 together with an unweighting assembly 102 to form a DAP unweighting system 100.

Preferred Embodiment—Operation

The DAP unweighting system 100 may function substantially similar to the prior art in a overall sense. A user 90 ingresses into the DAP unweighting system 100. Then the user 90 lifts the seal frame 124 in free space and places it in the appropriate height adjustment slots 126. The chamber 300, which is in communication with the seal frame 126 also preferably rises at this time. The user 90 activates the latching mechanism 128 to secure the height of the seal frame 124 relative to the support surface 129, and connects themselves to the user seal 302.

From this point the operation may differ from the prior art. The processor 140 on the unweighting system 102 may be configured to prompt a user for input of at least one user parameter via the input mechanism 141, such as a button shown in FIG. 9A. The user parameter may be one of a garment size, waist size, height, weight, body mass index, sex, age, body shape, height adjustment slot value or other personally related characteristic. Certain user parameters have not been considered in the prior art. In particular, the garment size, and height adjustment slot 126 selection are indicia that require no measurement device and are easily known or observed by the user 90, whereas height and weight may not be known, or may not be as accurate in predicting details about the user as garment size is. Additionally, whereas some people may be shy about inputting information about themselves, such as weight, a garment size and height adjustment selection are more generic and less offensive.

The processor 140 may be pre-configured with a set relationship between desired chamber pressure and unweighting amount, for example on a scale of 0-100 units where 100 units of unweighting corresponds to at least 20 mmHg and at most 100 mmHg. The pre-defined relationship may be linear or may be non-linear. Based on the user parameter(s) entered, the processor 140 may adjust the pre-defined relationship. For example if a pre-defined relationship is a line where 0 corresponds to 0 mmHg and 100 corresponds to 50 mmhg, the user parameter is a shorts size and height adjustment slot selection, and the value entered is 160 cm, the processor may change the slope of the predefined relationship such that 100 corresponds to 35 mmhg instead of 50 mmHg. The reader shall understand that in the case where the user parameter is a shorts size, a larger size shall cause the DAP unweighting system 100 to generate higher pressures for a given scale setting (0-100) than a smaller shorts size.

Similarly, the reader shall understand that in the case where the user parameter is a height adjustment slot, the higher the slot selected the more pressure the DAP unweighting 100 system will generate. Maximum pressures generated may range from about 20 mmHg to There are a myriad of combinations possible and listing all possible manifestations is outside of the scope of this specification, but the reader shall note the applicant's invention of using prior known data and tweaking in combination with a piece of data generally known by the user, but not needing to be measured, in order to arrive at a safe and accurate level of unweighting. Whereas prior art required sensors and measurement systems and processes to generate calibration curves, the applicant's invention does not.

Following determination of any adjustment to a pre-defined pressure adjustment curve, the user may operate the exercise machine 101 and unweighting assembly 102 to adjust speed, incline, degree of unweighting, or any relevant performance parameter of either system as generally done with prior art designs, and subject to the safety restrictions posed by an optional intercept assembly 145 as described below.

Inclining of the DAP unweighting assembly 100 shown in FIG. 1 causes the incline foot 150 of FIG. 7A to contact the ground surface 118 and push the exercise machine 101 to tilt at an incline as in its standard operation as an existing exercise machine 200. As in the exercise machine of FIG. 1A,7A, while the lower chamber portion 115 moves together with the exercise machine 101, the bellows 135 expands as the rack extends and therefore avoids causing tension and stretching on any part of the lower chamber portion to avoid ripping. The bellows 135 keeps the lower chamber portion 115 spread away from the rack and pinion gear so that the fabric material can't get sucked into the gear and ripped. As the DAP unweighting assembly 100 is declined, the bellows 135 contracts and again stays clear of the rack and pinion gear so as to avoid getting torn or ripped.

When the chamber 300 inflates, the chamber will try and expand and bulge out against all structural members 110 that are restraining it. A side view of this can be seen in FIG. 8 how the chamber 300 bulges up above the height of the seal frame 124 in the front and back. The chamber 300 will similarly transmit force laterally to structural members 110 such as handrails 104 in FIG. 1A and height adjustment posts 123. The height adjustment posts 123 will splay outward until they hit external retaining members 125. In this position the chamber 300 is fully restrained and added pressure will continue to transmit load to the framing and increase unweighting force on the user 90. The lower chamber portion 115 will be restrained from touching the ground surface 118 by chamber retaining struts 116 and will similarly reach steady state shape.

When the user 90 is finished they will command the DAP unweighting system 100 to turn off, disconnect from the user seal 302 and remove the seal frame 124 from the height adjustment slots 126 and egress from the system.

Safety

As described above, the DAP unweighting system 100 of the applicant's invention is meant to be universal for adaptation to many different types of exercise machines 101, and even as a field upgrade for an existing exercise machine 200 in the field. As an exercise machine 101 is generally not designed to be a component of a DAP unweighting system 100, the applicant has invented and disclosed ways to make combination of the two systems safe and applicable across a broad range of equipment. As stated earlier, these safety provisions are optional and may be replaced with integrated electrical system and programming instructions that replace equivalent components in the exercise machine 101 and unweight assembly 102. An electrical shutoff function may be created by the intercept assembly 145 whereby the signals between the exercise machine console 143 and the exercise machine base 144 are disconnected in the event of a safety error detected by the unweighting assembly 102. This disconnection may trigger a safety response in the exercise machine base 144, which no longer has communication and shuts down. The unweighting system processor 140 similarly may drive the system to detect an emergency stop sensor 146 signal if the unweighting system emergency stop is activated. An intercept assembly 145 may also be adapted to intercept power to the exercise machine base 144 and or exercise machine console 143, and cut the supply power to the exercise machine 101 while maintaining power to the unweighting assembly 102.

If external communication means such as WIFI, Ethernet, etc are provided, the DAP unweighting system 100 may communicate with external databases, export or import programming, reports, etc. Such functionality and operation has been extensively covered as previously stated and shall not be repeated here.

Servicing of the DAP unweighting system 100 is facilitated in the applicant's design with optional port assemblies 131 in the chamber as previously described. Access to internal components for replacement and cleaning may be achieved by opening zippers for example vs removing structural members 110 as required. This reduces service time, cost, and customer down time.

Alternate Embodiment—#1—Top/Bottom Chamber Connection

Alternatively, the unweighting assembly 102 may not provide a sealing surface 112 and the upper chamber portion 114 and the lower chamber portion 115 may seal directly to each other via a removable fastener as shown in FIG. 3A,10. In this case a portion of the additional frame member 111 may be used to secure either or both of the upper chamber portion 114 and lower chamber portion 115 to the exercise machine 101, but may not serve as an intermediate sealing surface 112 in and of itself. Any fastening means (i.e. fastener 130), such as a threaded stud, may still desirably be substantially airtight in the vicinity around the fastening means such that no air leaks past the fastening means, but the surface need not form a complete perimeter around the exercise machine as described above in relation to a sealing surface 112.

Advantages of not requiring a continual sealing surface 112 around the exercise machine 101 for sealing the chamber 200 may be a more reliable seal, easier removal of the chamber components, reduced structural complexity etc. Sealing in corners of a sealing surface 112, or joints where the sealing surface bends or curves to go around a perimeter of the exercise machine 101 can be challenging locations to seal and may susceptible to leak. In this alternate configuration where a sealing surface 112 is not provided and at least two portions of the chamber 300 connect together, a continuous separating sealing fastener can be used, such as a zip lock, airtight zipper, or other fastening means known to those skilled in the art of connection to members in an airtight fashion. Alternatively a standard separating fastener as just described may be used in conjunction with a sealing assembly 136 that covers the fastener in a sufficiently airtight manner. Such an example of a sealing assembly 136 is providing a pair of standard zippers in FIG. 10A with a gasket 137 disposed between them as described later.

Figure 10A:
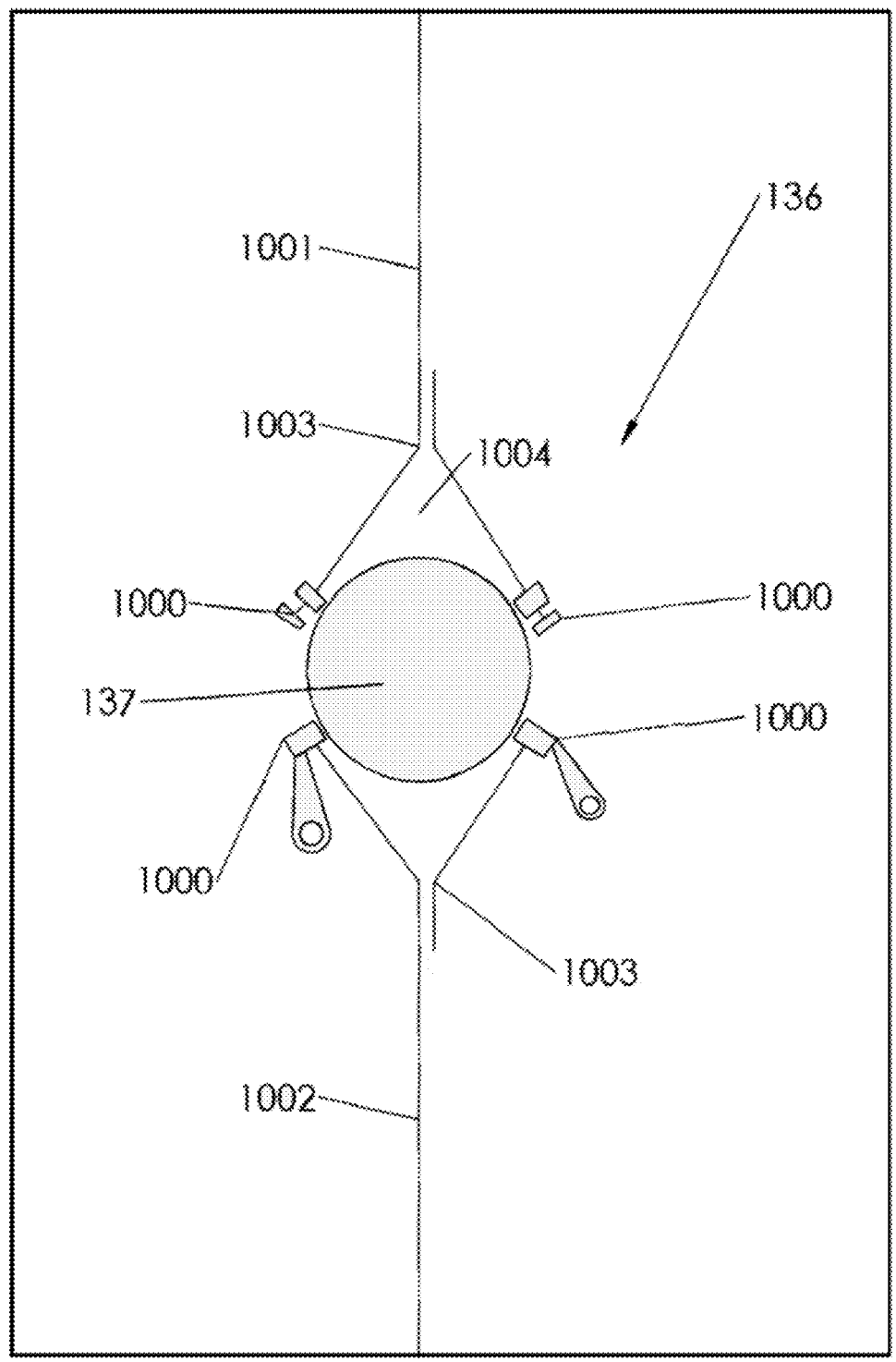
FIG. 10A—Shows a sealing assembly system for a separating fastener, a zipper as shown, that increases in sealing force when the two ends are pulled in opposite directions.

A sealing assembly 136 is not shown in FIG. 3A, but shall be generally known to those skilled in the art and an example may be referred to in FIG. 10A. Examples of a sealing assembly 136 in the case of the separating fastener being a zipper may be a gasket 137 pressed against the zipper for example with a strip of Velcro that covers that gasket on the inside of the chamber 300. As the chamber 300 is pressurized the higher pressure inside the chamber forces that Velcro strip against the gasket 137 and pushes it against the zipper, thereby increasing the sealing force. Other sealing assemblies are described elsewhere in this specification and may be applicable in this instance as well.

Alternate Embodiment—#2—Alternate Sealing Surface

Figure 12:
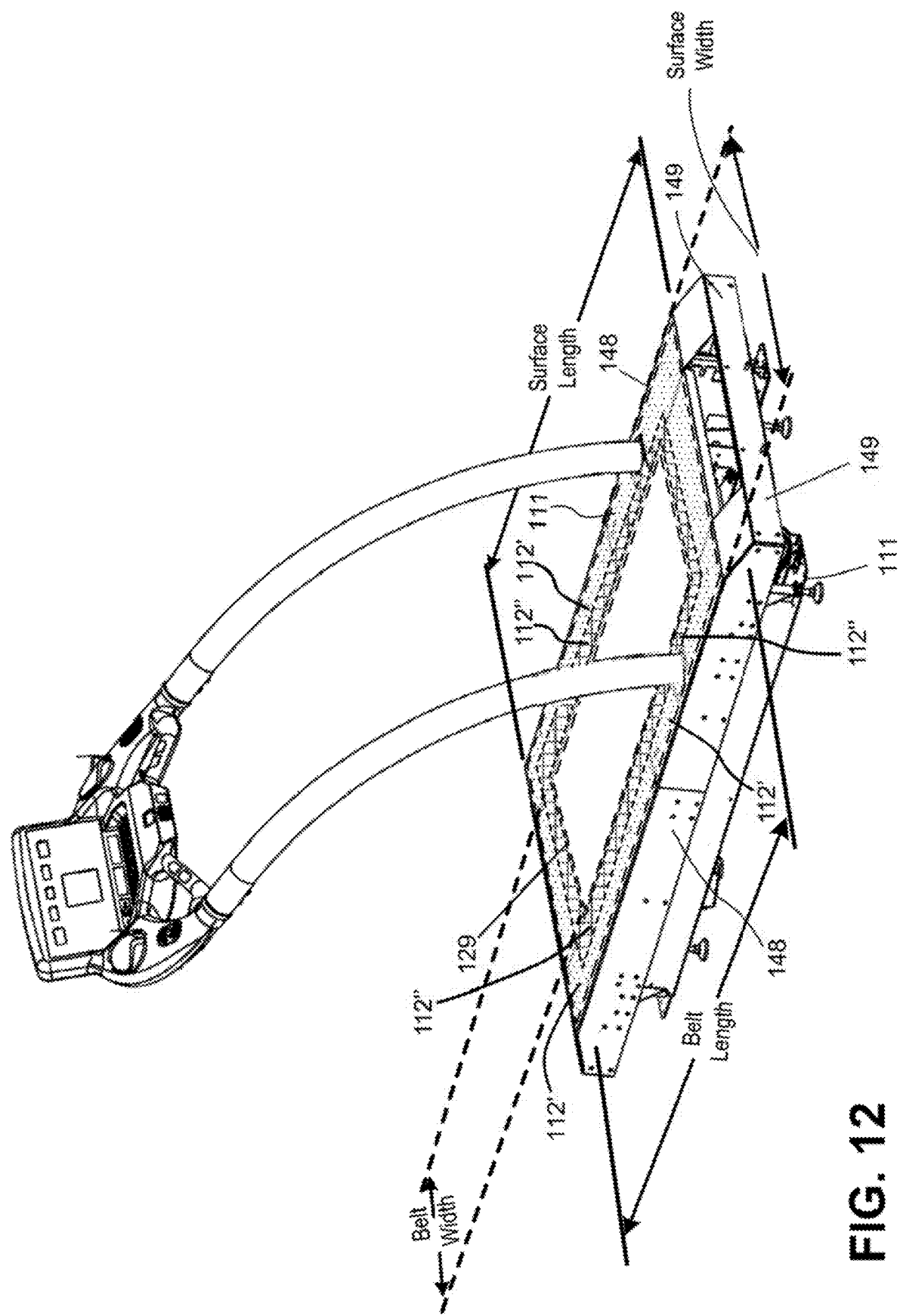
FIG. 12—Shows an additional variation generally corresponding with Alternate Embodiment #2—alternate sealing surface described below for attaching one or more additional frame members to an exercise machine to create a sealing surface at a top region of a treadmill that is smaller than an outer perimeter of the exercise machine. MISSING TEXT MISSING TEXT MISSING TEXT

While FIG. 5 shows a sealing surface 112 parallel to the exercise machine 101 side face and a perimeter larger than the external perimeter of the exercise machine, the perimeter of the sealing surface may alternatively be smaller than the external perimeter of the exercise machine if for example the sealing surface is formed on the top surface of additional frame members 111 (see FIG. 12), which are depicted as side covers 148 and end covers 149 in FIG. 5. In this case the sealing surface 112 may be substantially perpendicular to a side face of the exercise machine, or otherwise substantially parallel with a user support surface 129 of the exercise machine 101 shown as a running surface of a treadmill in FIG. 5 and identified as 112' in FIG. 12, and may therefore be formed within the outer dimensions of the basic exercise machine, on top of the side covers 148 and end covers 149. In this alternative of the preferred embodiment, the side covers 148 and end covers 149 would be adapted from what is shown in FIG. 5 to create a sealing surface 112' shown in FIG. 12 at a top surface region of the treadmill and substantially parallel to the running surface. The reader shall understand the concept of changing an orientation of the sealing surface 112, 112' is a modification generally understood by those skilled in the art, and the applicant has not illustrated this variation for the sake of brevity. One advantage of a sealing surface 112 that is substantially parallel with the running surface and smaller than an outer perimeter of the exercise machine may be that the size of an upper chamber portion 114 may be reduced, thereby reducing the forces exerted by the upper chamber portion on the rest of the system due to decreased area over which pressure is applied. For example treadmills are generally longer than necessary because users move forward and backward while running, but in a DAP system the user 90 is held in place longitudinally. Therefore a sealing surface 112' shown in FIG. 12 may be formed at a top surface region of the treadmill, and further a more limited sealing surface 112" may be formed interior to the front and back sections, over the running belt, without interfering with the user's running and allowing the chamber 300 to be smaller in length. This in turn may reduce the structure requirements of the exercise machine 101 or eliminate the need for any reinforcement of the exercise machine's structural members 110 that are used to secure and restrain the chamber 300 under pressure. Sealing in this manner may also eliminate the need for port assemblies 131 to accommodate handrails 104 if the lateral sealing surface is created interior to the handrails as also shown in FIG. 12, further simplifying the upper chamber portion 114 construction and assembly.

Alternate Embodiment—#3—Reduced Chamber Retaining Members

The chamber 300 may be clamped to the additional framing members 111 in several different configurations. Rather than two sets of chamber retaining members 113 as shown in FIG. 1,3B, only one set with matching fasteners 130 could be used, or in other words one of the sets of fasteners in FIG. 3B could be removed. In this case either the upper chamber portion 114 or lower chamber portion 115 is connected first, preferably with a gasket 137 as shown in FIG. 3B. Then, a secondary gasket (not shown) is placed on the outside surface of the upper chamber portion 114 or lower chamber portion 115, whichever was applied first. The secondary gasket may be optional depending on the properties of the chamber material, or it may be permanently attached to one of the chamber portions via, but not limited to, sewing, RF welding, etc.

Then, the other chamber portion is applied on top of the secondary gasket (if provided). Finally the chamber retaining member 113 is applied and clamped down via suitable means as previously described. During the clamping process the chamber retaining member 113 compresses together and seals substantially airtight the layered assembly in order from top to bottom of: lower chamber portion 115, secondary gasket, upper chamber portion 114, gasket 137, against the sealing surface 112. Note the lower chamber portion 115 and upper chamber portion 114 may be reversed without detracting from the applicant's invention.

Such a sealing scheme reduces one set of chamber retaining members 113 and speeds up assembly and service while reducing part count, cost, and weight.

Alternate Embodiment—#4—Sealing Assembly

Figure 10B:
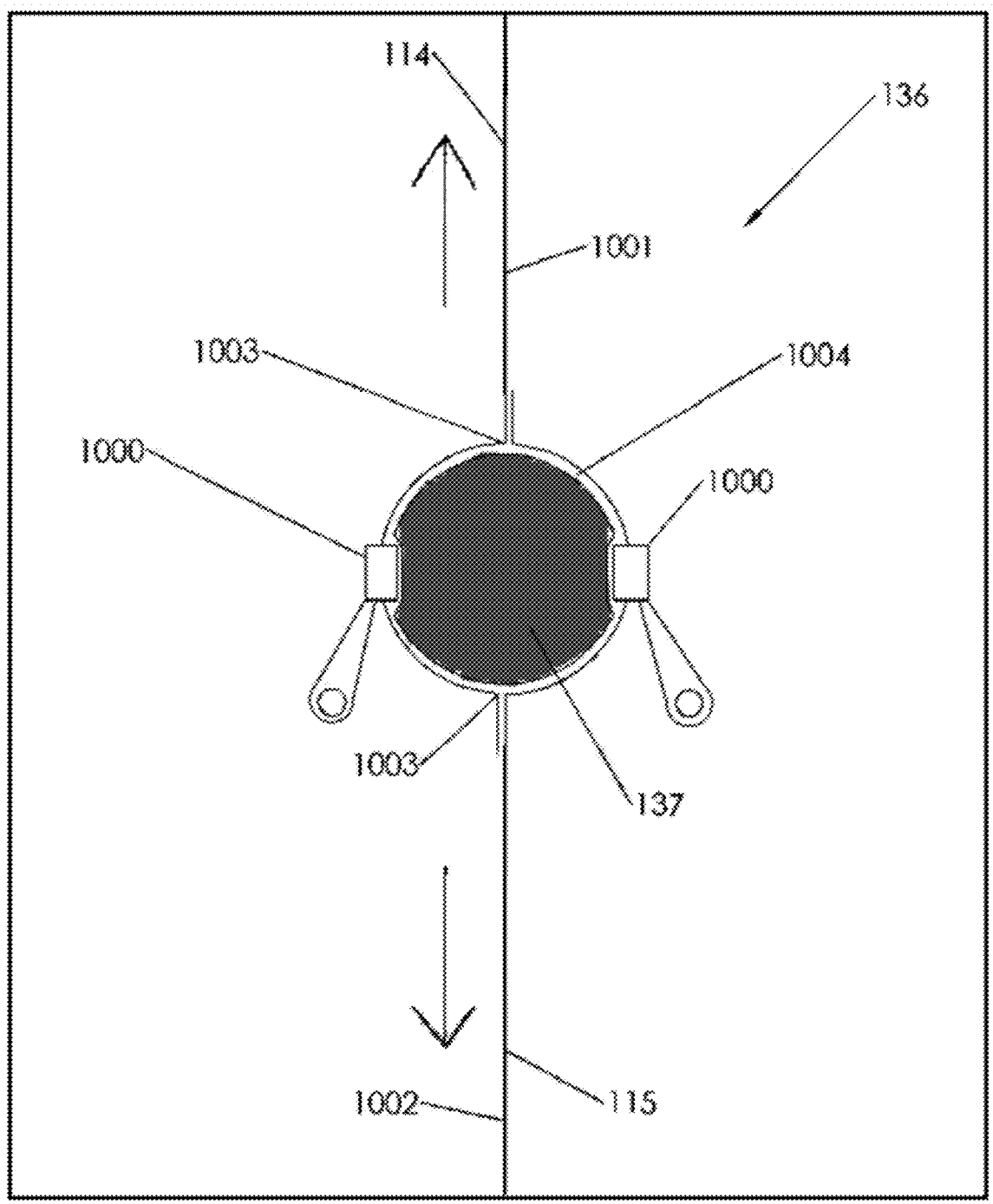
FIG. 10B—shows the sealing assembly of FIG. 10A connected together to seal the separating fastener.

FIG. 10A shows another method for securing an upper chamber portion 114 and lower chamber portion 115 together and to the additional frame elements 111 by using a sealing assembly 136 for a separating fastener 1000 as previously described in Alternate Embodiment #1. FIG. 10A shows the separating fastener 1000 and sealing assembly 136 in the open state and FIG. 10B shows the sealing assembly and separating fastener when closed together and sealed. The separating fastener 1000 may be airtight by design or may be accompanied as well by a sealing assembly 136 as previously described. A cross section of a scheme for sealing a separating fastener 1000 such as a zipper is shown in FIG. 10A. While airtight zippers do exist, they are limited in number of uses, are very tough to pull closed, are very expensive, and may not be fully separating. The applicant is unaware at this time of a good system for sealing a zipper in the prior art that fixes these fundamental barriers to adoption and herein provides a solution shown in FIG. 10A,B.

The sealing assembly 136 of FIG. 10A is comprised of a first fabric 1001 and second fabric 1002, wherein the goal is to allow the first fabric and the second fabric to be separable, for example insertion of an object like an arm, leg, hip, existing exercise frame element 103, or simply for removal of the upper chamber portion 114 for example.

A fabric joint 1003 is formed at one end of the first fabric 1001 and second fabric 1002 to create a "Y" shape at one end of the first fabric and second fabric. On each of the split ends of the "Y" shape a separating fastener 1000 such as a zipper, zip-lock, etc is attached for example via sewing/seam taping, RF welding, or other suitable process that produces a substantially airtight junction. Therefore the first fabric 1001 and second fabric 1002 each have a "Y" shape on one end with two separating fasteners 1000 on each exposed arm of the "Y". The first fabric 1001 may comprise the male side of the separating fastener 1000 and the second fabric 1002 the female side of the separating fastener 1000 or vice-versa.

A gasket 137, for example with a cross section of a circle, oval, doughnut, or other gasket shape known in the art is disposed between the first fabric 1001 and second fabric 1002 such that combining the two halves of the separating fasteners 1000 of the first fabric and second fabric together encapsulates the gasket inside a pocket 1004 as shown in FIG. 10B. The gasket 137 may be separable as just described or may be permanently attached to either the first fabric 1001 or the second fabric 1002 such that it is sandwiched for example between the two respective separating fasteners 1000 on that piece of fabric. In this case where the gasket 137 is permanently connected to a fabric piece, the gasket may be formed in a tear drop shape and stitched into the fabric piece at the point when the "arms" of the fabric joint 1003 and the "Y" shape is created. Permanently connecting the gasket 137 to one side may ease assembly when connecting the two halves of the separating fastener 1000 and if one side, the upper chamber portion 114 for example, is deemed to have a lower life expectancy, the gasket may be sewn permanently to the lower chamber portion 115.

To assemble, the separating fastener 1000 corresponding the inner side of the area to be sealed, i.e. side A in FIG. 3B or otherwise the inside of the chamber for example, is connected first, joining the first fabric 1001 and second fabric 1002. Then the separating fastener 1000 corresponding to the outer side of the area to be sealed is fastened together thereby trapping the gasket 137 in the pocket 1004 between the two separating fasteners as shown in FIG. 10B. This process may be reversed if for example the inside of the area to be sealed is more accessible.

It is preferable that the gasket 137 is sized so that the deflated state of the chamber 300 already biases the gasket against each separating fastener 1000 from inside the pocket 1004. In this fashion air is prevented from moving past each separating fastener 1000 from the inside or outside and the seal is bi-directional. As the inside of the area to be inflated, for example the chamber 300, the end of the first fabric 1001 and second fabric 1002 that do NOT have the "Y" junction are pulled in opposite directions with a tensile force in the direction of the arrows in FIG. 10B. This tensile force wants to move the fabric in opposite directions and tries to elongate the pocket 1004 to form a straight line versus the rounded shape the pocket formed prior to inflation and shown in FIG. 10B. This movement will compress the gasket 137 further against the separating fasteners 1000 and may deform the gasket slightly or greatly depending on the properties of the gasket, but in all cases will improve the seal and prevent air, or other gas, from passing from one side to the other.

Removal simply requires undoing an outer separating fastener 1000 or inner separating fastener 1000, whichever is easiest, and then removing the other separating fastener which is now accessible. Herein lies therefore, a very simple design and method of creating a simple, flexible, and inexpensive sealing assembly 136 for an inexpensive separating fastener 1000.

Alternate Embodiment—#5

Figure 2B:
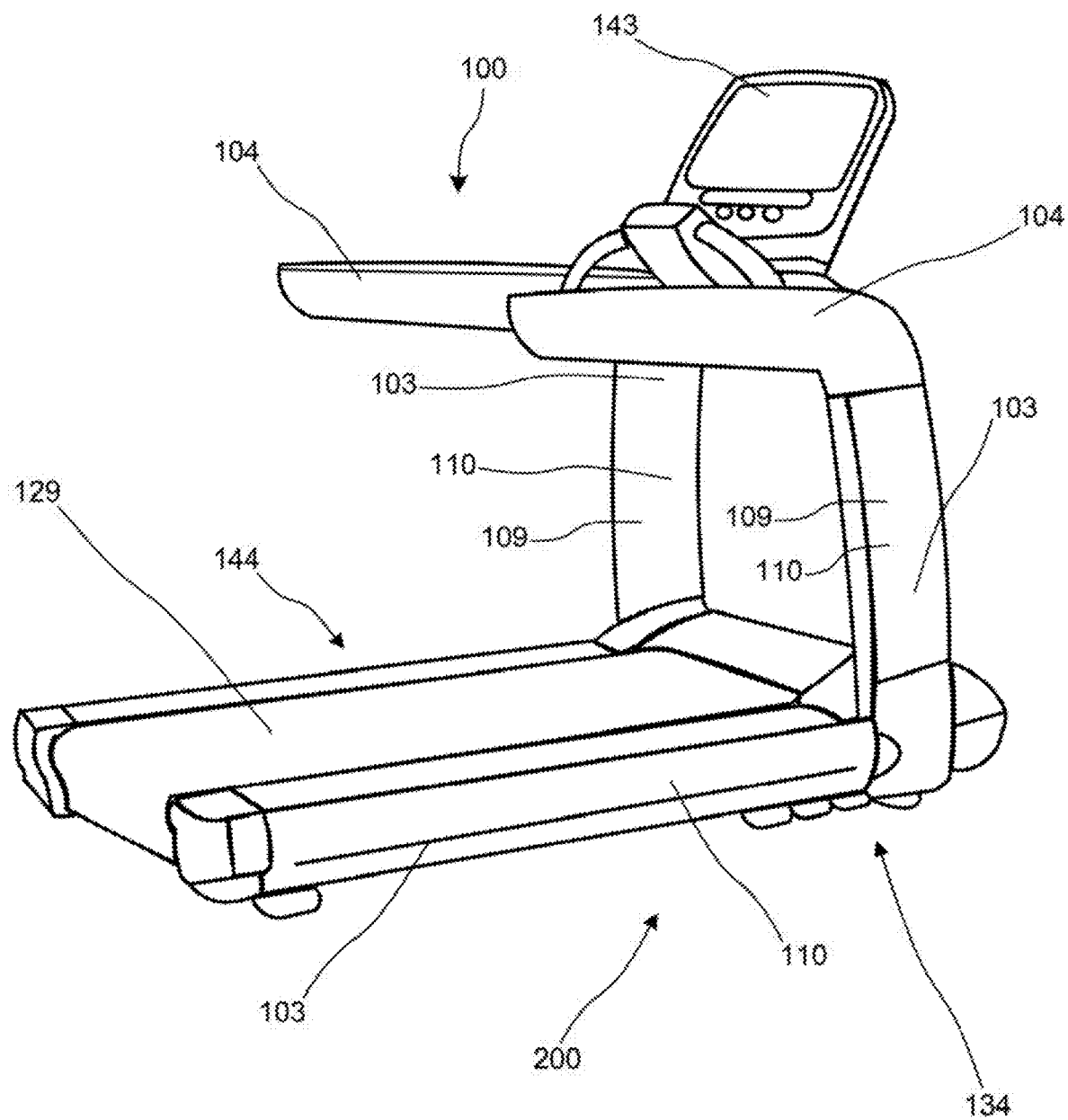
FIG. 2B—Shows another example of an existing exercise machine which is suitable for integration with an unweighting assembly for creating a DAP unweighting system using a linear actuator lead screw, incline weldment, and wheels to incline the running surface.
Figure 7B:
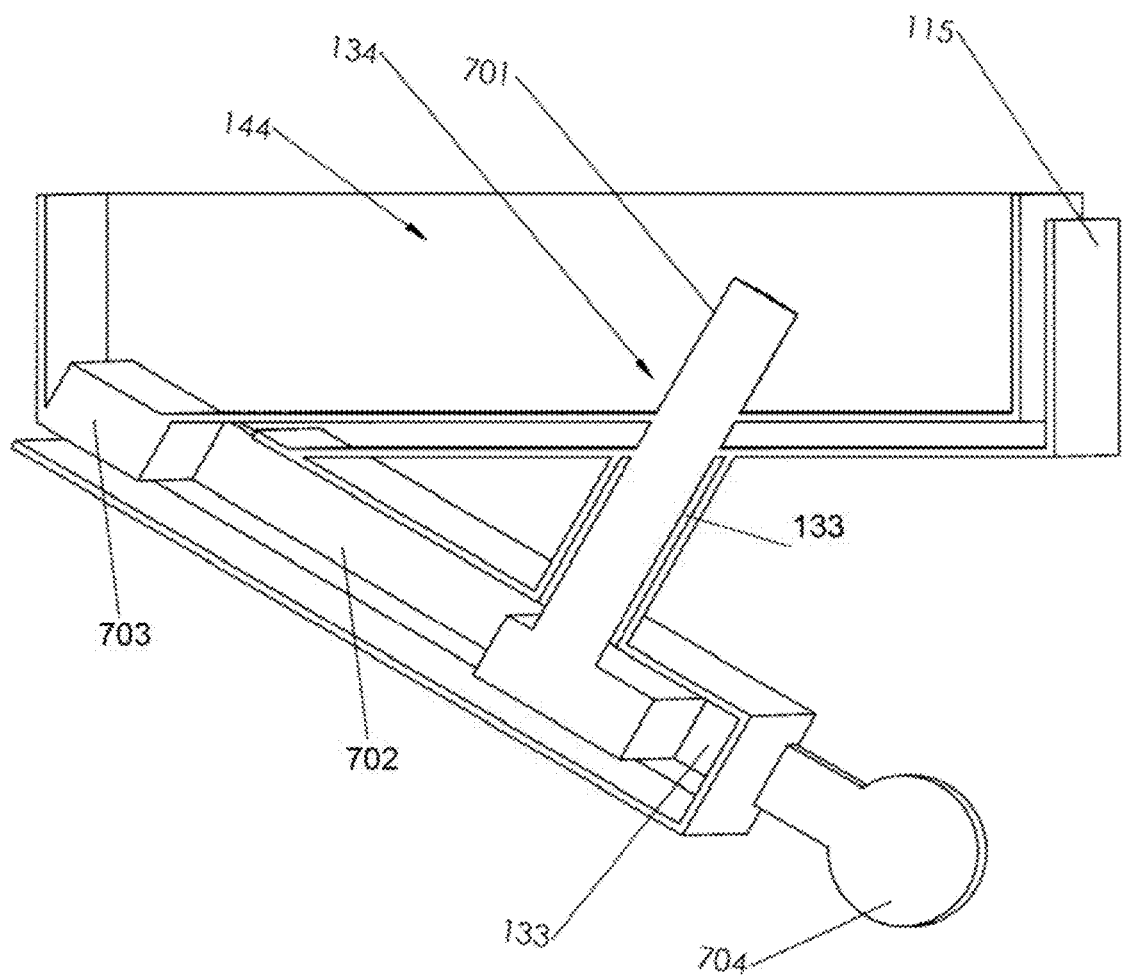
FIG. 7B—Shows a chamber compartment for accommodating a leadscrew style incline assembly of the exercise machine.
Figure 7C:
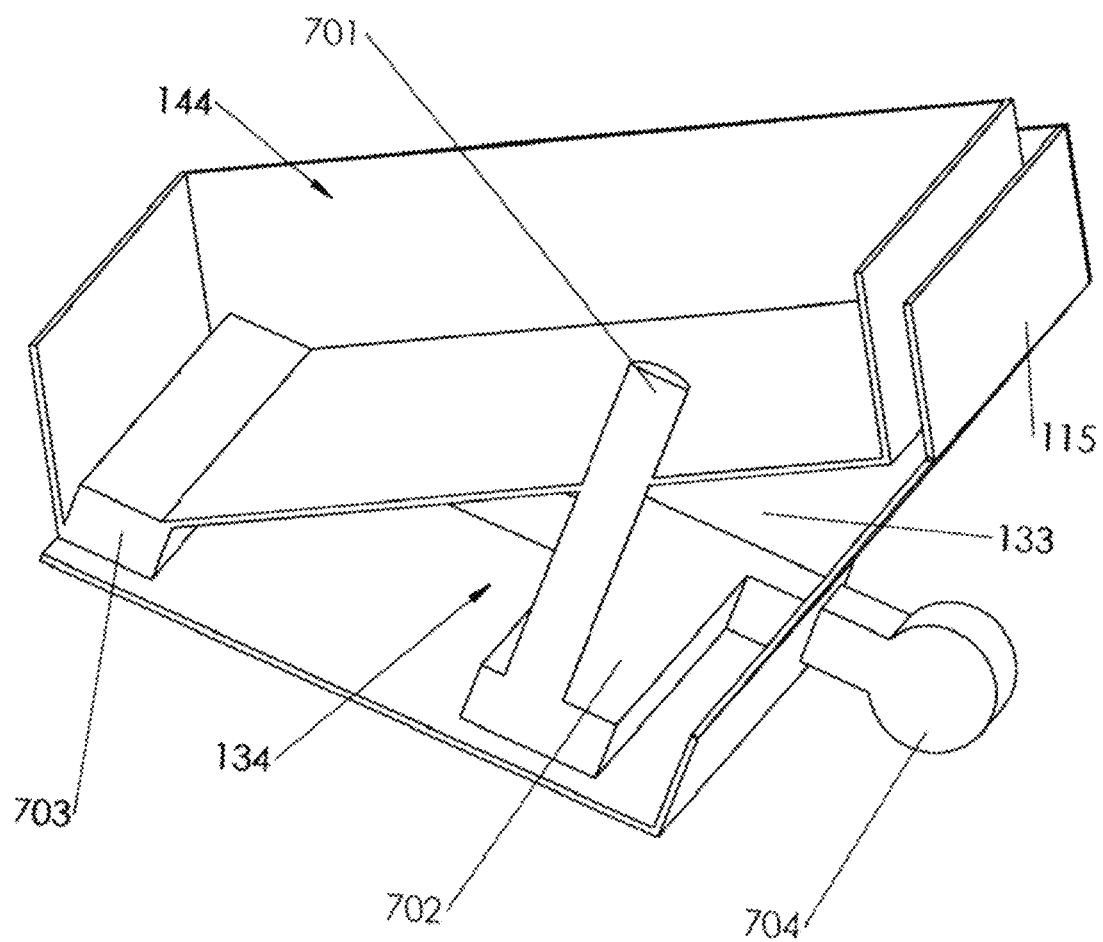
FIG. 7C—Shows another variation on a chamber compartment for accommodating a leadscrew style incline assembly of the exercise machine.

In the preferred embodiment, a flexible lower chamber portion 115 with one or more chamber compartments 133 was disclosed as it relates to accommodating a rack and pinion style incline assembly 134. In the case of a linear actuator 701 style pivoting incline assembly 134, a rigid lower chamber portion 115 is also not very practical because the movement of the incline assembly 134 is not linear, and typically bars rotate when pushed on by the linear actuator 701 as shown in FIG. 2B,7B-C. A rigid lower chamber portion (not shown), for example a plate would require removal of the incline assembly 134 and then re-applying on the outside of the rigid base, but then this could throw off the accuracy as now the geometry of the incline assembly is different with the added thickness of the base in between what was the attachment surface to the exercise machine base 144 and the new incline assembly 134 connection point exterior to the base plate. A flexible lower chamber portion 115 with appropriately designed chamber compartments 133 on the other hand can be constructed to accommodate the pivoting movement as shown in FIGS. 7B,C.

FIG. 7B shows an anterior section view of a flexible lower chamber portion 115 with a chamber compartment 133 that encompasses bars of a lead screw style incline assembly 134. Two chamber compartments 133 are created: one surrounding the lead screw and one surrounding the incline bar weldment 702 and these chamber compartments are joined to allow the lead screw to connect with the incline bar weldment. FIG. 7B depicts a exercise machine base 144 shown as a treadmill base pan with a lead screw as the linear actuator 701 protruding through the bottom and connected to an incline bar weldment 702 that pivots around an anchor point 703 on the base pan and has wheels 704 on the front of the incline bar weldment. The other contents typically found on the base pan, treadmill drive motor, incline motor, etc. are not shown for the sake of clarity. As the lead screw extends and retracts, the angle between the bottom of the base pan and the incline bar weldment 702 increases and decreases respectively. The wheel 704 rolls along a ground surface 118 as the incline bar weldment 702 moves and thus the angle of the base pan, which is substantially parallel with the running support surface 129, increases and decreases according to the position of the lead screw. In the applicant's invention the lower chamber portion 115 may be constructed to surround the base pan, the lead screw, and the incline bar weldment 702 up to the point of the wheel 704, but not including the wheel. Attachment to the base pan and the rest of the exercise machine base 144 may be done via additional frame members 111, which are not shown for clarity, but have been described extensively throughout this application as to how they function and their purpose for interfacing the chamber 300 to the exercise machine 101.

The lower chamber portion 115 comprises a chamber compartment 133 that forms an airtight seal around the incline bar weldment 702 just above where the wheels 704 are attached. Such sealing may be done via a port assembly 131 as described herein, or otherwise known in the art. The section of the chamber compartment 133 around the lead screw may be separable using an airtight fastener, or fastener plus sealing assembly 136 as to allow insertion of the chamber compartment without removing the incline assembly 134. Alternatively, the end of the lead screw may be detached from the incline bar weldment 702 in order to slip through the chamber compartment 133 surrounding the lead screw, and then the lead screw reconnected to the weldment. In this way the chamber compartment 133 need not incorporate any fastening means to open it up and seal again around the lead screw.

FIG. 7C shows another option for sealing around an incline assembly 134 that uses a linear actuator 701 in the incline assembly 134 that does not require fasteners or removal and reconnection of the lead screw component. The construction of the exercise machine base 144, shown as a base pan in FIG. 7C, and incline assembly 134 are similar to FIG. 7B however in this case, the chamber compartment 133 does not extend past the lead screw and instead stays at the front of the system as a single chamber compartment 133. This simplifies the design of the chamber compartment 133 in that no sealing assemblies on the lower chamber portion 115 are needed, only a port assembly 131 for sealing just above where the wheel 704 is attached as in FIG. 7B. Excess fabric of the chamber compartment 133 may be controlled via a bellows-like design that accordions up and down from a flat to a triangle shape, or may simply be free to be squished between the base pan and the incline bar weldment 702 as the exercise machine 101 moves up and down, or may be guided by bars or other elements found in bellows. The bottom surface of the incline bar weldment 702 may serve as a frame on to which the lower chamber portion 115 is connected in order to prevent the chamber compartment 133 from bulging excessively against the ground surface 118.

This connection (not shown) may be done via tabs and Velcro or tie wraps, other suitable means known in the art. Connection of the lower chamber portion 115 to the base pan and rest of the exercise machine 101 may be similar to that as described above in relation to FIG. 7B. By constructing in this way, the lower chamber portion 115 can be laid on the ground surface 118, the treadmill inclined on top and the wheels 134 stuck through the chamber compartment 133 and ports assemblie 131 sealed just above the wheels so that wheels are rolling on the ground surface and not on the fabric to reduce wear, and the lower chamber portion is allowed to incline up and down along with the exercise machine. Then the rest of the lower chamber portion 115 may be connected to the additional frame members 111 and the bottom surface of the exercise machine 101 is sealed substantially airtight, and chamber retaining struts 116 added as necessary for reasons described earlier.

The reader shall note that while the applicant prefers a fabric lower chamber portion 115 for reasons already discussed, a rigid lower chamber portion could also be used and hole cutouts or mounting provisions provided as necessary for accommodating different styles of incline assemblies 134.

For example in the case of a rack and pinion style incline assembly 134 as shown in FIG. 1 and FIG. 7A, a flat base plate could be used and bolted to the underside of the exercise machine base 144. The base plate would have holes for allowing the rack to move in and out and could have a port assembly 131 for sealing around the holder for the rack so that a portion of the rack was in the sealed area and portion was outside of the sealed area. Or alternatively the base plate could incorporate a bellows 135 as shown in FIG. 7A, and the bottom of the bellows may have a hole or provision for allowing the incline foot 150 to protrude through the bottom so the incline foot rests directly on the ground surface 118 as was described earlier, or alternatively sandwiches the bellows between the incline foot and ground surface as shown in FIG. 7A. In the case where leveling feet are used in the rear, a similar bellows mechanism or other style of chamber compartment 133 may be used with similar provisions for allowing the leveling foot to protrude through directly to the ground as with the incline foot 150.

In the case the incline assembly 134 uses a linear actuator 701 and incline bar weldment 702 as shown in FIG. 7B,C, the incline assembly may be removed and a rigid base plate, comprising at least a portion of the lower chamber portion 115, may be installed and connected to the bottom surface of the exercise machine base 144. While more complicated in assembly because of required removal of the incline assembly, it is still feasible. Because the incline assembly 134 rests on the outside surface now, the only provision needed is a hole in the base plate with port assembly 131 allowing the linear actuator 701 to extend and retract in and out of the hole in the base plate without breaking a seal. A bellows 135 seal be used to encapsulate the lead screw portion of the linear actuator 701 as it moves in and out, or a lip seal style gasket that doesn't itself move, but allows for moving of the linear actuator past the lip seal will maintain a sufficiently airtight seal.

The reader shall note that many combinations of exercise machines 101 and incline assemblies 134 are available in the field and may require small modifications to the specific examples given herein. What is important is the applicant's invention of providing a system that is adaptable to existing exercise machine 200 designs and may either encapsulate the full exercise machine base 144 or allow a portion thereof to protrude through directly to the ground surface 118, but in all cases may be fit to existing exercise equipment, may take advantage of structural components of existing exercise equipment, and may incline or decline together with existing exercise equipment instead of the prior art's strategy of building a secondary chamber and framing system around the existing equipment. The applicant's invention of adapting to existing exercise equipment further provides advantages of prior art comprise integrated exercise equipment with DAP provisions in that this prior art requires an entirely new machine vs the ability to upgrade an existing exercise machine and all the negative aspects that come with that in terms of lack of volume scale leading to cost and higher barrier to adoption as described earlier.

Alternate Embodiment—#6

In FIG. 4B, another variation of a seal frame 124 is provided in combination with a lateral reinforcement member 147 that spans the existing exercise machine frame elements 103 depicted in FIG. 4B as curved handrails 104. An exercise machine console 143 is not shown in FIG. 4B but the reader shall recognize the console may be substantially similar to that shown in other figures in this application.

The rear height adjustment posts 123 may be as shown and similar to that of FIG. 1 or as otherwise described in this application, or alternatively may be optional as described in other height adjustment schemes of prior art.

The seal frame 124 may comprise a rear portion that is similar to a rear portion of the seal frame of FIG. 1 and the preferred embodiment and may use similar external retaining members 125 to contain the rear height adjustment posts 123 from splaying laterally outward under pressure. Otherwise the construction of the seal frame 124 may be substantially similar to the preferred embodiment other than a front portion of the seal frame.

A front portion of the seal frame 124 may be configured to have a plurality of pegs 151 at or around a central portion of a front portion of the seal frame as shown in FIG. 4B. Whereas prior art and the preferred embodiment describe and illustrate a series of height adjustment slots 126 on height adjustment posts 123 on either side of the exercise machine 101, the embodiment of FIG. 4B puts the height adjustment capability on the seal frame 124 with a fixed latching mechanism 128 (not shown in detail but generally known in the art) positioned on the lateral reinforcement member 147. Each pair of a plurality of pegs 151 is configured to connect to the latching mechanism 128 as shown in FIG. 4B, and the reader shall note that while pairs of pegs are shown in FIG. 4B, and two latching mechanisms are therefore provided, the applicant's invention may function with only one vertical row of pegs or even three or more rows of pegs.

Therefore the applicant's invention shall not be limited to the specific illustration of FIG. 4B but rather encompass the concept that the height adjustment capability may be integrated with the seal frame 124 as opposed to the height adjustment posts 123, which is completely different from prior art. Similarly, but not shown, the rear height adjustment scheme may be designed such that the rear height adjustment posts 123 have a single location into which one or more of a plurality of pegs 151 configured in a vertical row on a rear portion of the seal frame 124 are inserted and locked in order to fix a height of the seal frame relative to the support surface 129.

The pegs 151 may be in the form or cylinders, hooks, squares, or any other suitable shape or form that successfully mates and creates a mechanical connection in order to prevent the front or rear portion of the seal frame 124 from moving substantially vertically relative to the exercise machine 101. The latching mechanism 128 may be a clasp, hole, latch, gate lock, handle, peg, screw, hook, or other known means for locking or connecting the peg to a surface, shown in FIG. 4B as the lateral reinforcement member 147. The latching mechanism 128 may further be connected directly to the console (not shown) or other structural member 110, and need not be connected only to the lateral reinforcement member 147. The reader shall note that many such permutations are possible and the spirit of the applicants invention shall encompass all such shapes, forms, methods of locking, methods of connection, mechanisms for locking or restricting movement, and that all of these may be located in any suitable location and connected to any suitable member such that the ultimate goal of substantially restricting vertical movement of that portion of the seal frame is achieved, wherein the adjustment is incorporated into the seal frame 124, not the height adjustment post 123 as in prior art and the preferred embodiment.

One benefit of this embodiment of FIG. 4B is that overall bulk, height, and simplicity of the unweighting assembly 102 is achieved. A single latching mechanism 128 may be used, reducing part count vs. the preferred embodiment where two latching mechanisms are shown, and a single seal frame strut 139 may be used to hold the pegs 151 vs the U-shape seal frame struts of FIG. 4B. The seal frame strut 139 may also serve as a handle for picking up the seal frame 124 from the lowered position during an ingress process to make ingress easier for the user 90 or a therapist working with the user. The seal frame strut 139 may also be adapted for additional handlebars (not shown) to give additional stability and support surfaces to the user during exercise. In the case of disabled or elderly patients this may be beneficial. In removing the front height adjustment posts 123 and using a single vertical row of pegs 151, not only is the look of the machine made less intimidating but an additional latching action, and potential for failure, is similarly removed. If the front height adjustment posts 123 were moved central, it would block the view of the user 90 and their access to the exercise machine console 143, which would be detrimental to the use of the system. The embodiment of FIG. 4B therefore provides a unique construction that provides efficiency in design and operation while maintaining a clear view to the console by the user with minimal interference. Additional benefits of the embodiment of FIG. 4B may be that the seal frame 124 is allowed to drop lower for improved ingress vs the embodiment of FIG. 1 where the seal frame pegs 151 may interfere with the handrails 104.

One or more lateral reinforcement members 147 may serve to reinforce the existing exercise machine frame elements 103, such as handrail 104s of FIG. 4B, against the lateral load applied by the chamber 300 (not shown in FIG. 4B). Where the exercise machine console 143 may be adapted to connect handrails 104 (as shown in FIG. 1), the console may not have been designed to be suitable to carry lateral side loading exerted by the chamber because the exercise machine was not originally intended to be used in combination with the unweighting assembly 102. While a lower connection point of existing exercise machine framing elements 103 is generally robust, for example where handrails 104 drop into the exercise machine base 144 as shown in FIG. 4B, an upper connection may not be, for example the connection to an exercise machine console 143. The reason is that exercise machines 101 require a strong exercise machine base 144 to which existing exercise machine frame elements 103 attach to necessarily support a user's weight. Conversely the upper connection point of handrails 104, for example to the exercise machine console 143 may not be robust, and so a lateral reinforcement member 147 may take the load versus the console. In this way, the existing exercise machine frame elements 103 are supported firmly on both ends and lateral load from the chamber 300 is carried efficiently. One or more lateral reinforcement members 147 may be connected to the existing exercise machine frame elements 103 in a suitable manner such as clamps, bolts, screws, clasps, latches, or other means known to those skilled in the art. The shape and material of the lateral reinforcement member 147 may be designed relative to the expected loads applied and the strength of the exercise machine 101. The lateral reinforcement member 147 may be bent sheet metal made of a steel or aluminum alloy, or may be molded from carbon fiber as but two examples. The location of the lateral reinforcement member(s) 147 is similarly not critical as long as it provides sufficient support and does not interfere with operation of the exercise machine 101.

A variation in FIG. 4C that the reader shall note is that the embodiment of FIG. 4B may be modified by maintaining a single peg 151, or other attachment means on the front portion of the seal frame 124, and disposing a movable height adjustment assembly 400 on the lateral reinforcement member 147, or alternatively elsewhere on exercise machine 101. The movable height adjustment assembly 400 may be disposed for example on a lateral reinforcement member 147 with a latching mechanism 128 that mates with the single peg 151, otherwise a portion of the seal frame 124 (not shown in FIG. 4C) to lock the seal frame to the movable height adjustment assembly. In FIG. 4C the latching mechanism 128 is depicted as a slot 402 into which a peg 151 (not shown in FIG. 4C) may drop down and a cover 401 that may be closed and locked to secure the peg inside the latching mechanism. The details of such a latch may be similar to the mechanism for closing a gate, or otherwise known to those skilled in the art. In this alternative construction, the movable height adjustment assembly 400 may be movable and lockable in its own right relative the exercise machine 101 to fix a height of the latching mechanism 128 into which the single peg 151 on the seal frame 124 connects. The moving and locking of the movable height adjustment assembly 400 may be done as shown in FIG. 4C with a series of holes 403 in the movable height adjustment assembly that may mate up with a locking hole 404 into which a peg (not shown) may be inserted to lock in the position of the movable height adjustment assembly. The reader shall note this is but one variation and many ways of locking two sliding members together are known in the art. This movable height adjustment assembly 400 may be located along a midline of the DAP unweighting system 100 proximal to the xercise machine console 143, or off to one side without departing from the scope of this alternate embodiment.

The single peg 151 on the seal frame 124 may be connected to the movable height adjustment assembly 400 as described, and combination moved together to the correct height and the movable height adjustment assembly subsequently locked, wherein the rear height adjustment mechanism (whichever it may be) is further then locked in. Alternatively the movable height adjustment assembly 400 may be set first and locked in height relative to the support surface 129, and then the single peg 151 of the seal frame 124 connected with the movable height adjustment assembly while also engaging the rear height adjustment mechanism (whichever it may be), thereby fixing the height of the seal frame 124 relative to the support surface 129. The order of operations therefore is not critical to the overall goal of the invention of fixing the seal frame 124 in place relative to the support surface 129

The movable height adjustment assembly 400 may comprise sliding elements, such as a telescoping tube concept, or a non-sliding bar, such as a pin plus hole concept as shown in FIG. 4C similar to a squat rack for lifting weights where the pin is on a suitable portion of the exercise machine 101 and the bar with mating holes is free floating with a series of holes that lock the bar at a specific height relative to the pin.

The bar is but one concept and the reader shall note that the specific embodiment is but one example and shall not limit the scope of this invention. The concept is that there is an independent movable member as part of the movable height adjustment assembly 400 that fixes a location into which the seal frame 124 may connect, the seal frame having a single connecting member vs. a vertical row of pegs 151 as shown in FIG. 4B, thereby reducing further the complexity and bulk from the seal frame and height adjustment scheme of FIG. 4B.

Description—Conclusion, Ramifications, Scope

Thus the reader will see that the various inventions described herein provide an economical way to easily create an efficient DAP unweighting system 100 that may be adapted to a multitude of exercise machines 101 in order to reduce complexity, footprint, shipping and installation burden, and overall cost of the system, thereby making it more accessible to users and customers. Additionally the reader will see that inventions described herein may take advantage of current mass production processes to keep the additional cost minimal, minimal tooling costs, and that by reducing component count, the applicant has not only reduced the manufacturing costs but reduced the level of complexity of operating the system, and reduced the bulk of the system. The reader shall further note that the applicant has invented a way to solve one of the biggest complaints with prior art devices, which is that users must replace existing exercise equipment 200 they already have in favor a brand new expensive system.

While the above description contains specificities, these should not be construed as limitations on the scope of the invention, but rather as an exemplification of preferred embodiments thereof. Many other variations are possible and some of them further described below.

Increased Functionality

The functionality of the DAP unweighing system 100 as described herein may be augmented by many different sensors, actuators, hardware accessories, etc. Many of these are used by prior art and may be combined with the applicant's invention to enhance performance or utility.

Load cells may be added for example inside the lower chamber portion 115 and underneath the exercise machine 101 in order to gather weight data for use in calibration, real time weight display or gait analysis data gathering. Load cells may similarly be incorporated within the exercise machine 101 as in various prior art designs and provide the same purpose. A cable and accompanying circuitry may be provided from the load cells to the processor 140 to take into account this information for improvement of accuracy in calibration, or providing gait feedback to the user as but one example.

IR sensors, accelerometers, IMUS, and/or cameras may be similarly added to the DAP unweighting system 101 to capture information about users gait and provide feedback thereof. Sensors may be mounted to existing exercise machine frame members 103, structural members 110, additional frame members 111, or other components of the DAP unweighting system 100 and may similarly be in communication with the processor 140, or alternatively may be processed and displayed by a separate electronics system. Some examples of gait functionality are evident in prior art descriptions and devices.

Connectivity and external database management of data may be added to the DAP unweighting system 100 in order to relay data back and forth remotely. The data may consist of, but not limited to, gait metrics, session metrics like speed and incline over time, pain scales, patient data and history reports, programs and executed protocols, etc. The data may be used for example, but not limited to, remote system diagnostics, patient care, client fitness training program management, etc. Connectivity may run directly from the DAP unweighting system 100 to the Internet via a cellular modem or wife module, or may connect to an auxiliary communication device such as a smartphone or tablet via WIFI, Bluetooth, or similar wireless protocol known to those skilled in the art.

The readers shall note that many such sensors are available and may provide enhanced functionality and what is described above are but a few examples and shall not limit the scope of the applicant's invention.

Multiple Models and Types of Exercise Equipment

The reader shall note that the applicant's invention and figures as shown are largely described in the context of the exercise machine 101 being a treadmill. Many of the figures depict a slat belt treadmill model that is commercially available. The reader shall note however that the applicant's inventions extend beyond the specific implementations depicted in the figures and described above, and may be adapted and modified to accommodate many different models of treadmill and many different exercise machines 101.

Treadmill models for example that incorporate minimalistic handrails 104 may utilize a bag that is substantially conical in shape with port openings in appropriate locations such that the handrails 104 do not carry any side load, and the load is carried in the stresses of the fabric alone. Alternatively, more substantial handrails 104 could also be provided or contouring of the bag via internal structural members that do not connect to or rely on the handrail 104 of the exercise machine 101 for structural support. Incline assemblies 134 other than those of FIG. 7A-C may similarly be adapted to sit within a basin the machine sits in or via a lower chamber portion 115 that allows a portion of the incline mechanism 134 to protrude through with a custom sealing assembly 136 for that model of equipment. Chambers 300 may incorporate a multitude of port assemblies 131, or more flexible ports in order to allow for adaptation to different console support members 109 designs and existing exercise machine frame elements 103 and based on the chamber design may or may not transfer load from the chamber to the console support members or other elements, and may carry the load internally via fabric stress in the chamber 300, or lateral reinforcement members 147. The port assemblies 131 may be altered in location on the chamber 300, size, material property, or as otherwise advantageous for accommodating various elements (handrails, cabling, etc) of different models of existing exercise machines 200. Access points for adjustment of the running service may be added or removed as well based on the specific model of treadmill for example. In all these examples, a majority of the system, or the full system entirely may remain the same with only one or a few components (such as the chamber 300) needing to adapt to a specific model. In this way, great economies of scale may be achieved and costs reduced to manufacture and install integrated new units or field retro-fits.

Other exercise machines 101 such as stationary bikes, elliptical machines, steppers, etc. may similarly be adapted to be housed within the DAP unweighting system described herein. A common element of all exercise machines 101 is some framing components to hold motors, moving parts, and support a user and these framing elements may be used as described in the preferred embodiments to reduce the necessary components required to create a DAP unweighting system 100 with that specific exercise machine. In the end the applicant's invention provides guidelines and methods for how to adapt the applicant's invention by changing for example, but not limited to, the chamber height 106, the chamber width 105 and or shape of the chamber 300, the footprint of the additional frame elements 111, the presence or absence of a sealing surface 112 and the location and orientation of such sealing surface, the ability to accommodate incline of the exercise machine 101, mechanisms for adapting to framing elements of the exercise machine which may need to be both internal and external to the chamber via port assemblies 131 and require sealing, ability for fixing a maximum height of a user seal and providing a support structure for the user, and ability to combine functionality in safe and monitored manner via communication intercepts assemblies 145 to ensure a user cannot get themselves in an unsafe situation. A generic example of such adaptation is a lower chamber portion 115 that encompasses the bottom surface of an exercise machine 101 and in footprint that is larger than the exercise machine. The lower chamber portion 115 is supported by necessary additional frame members 111 and connected to the exercise machine 101 or may alternatively sit on the ground surface 118 independent of the exercise machine. An upper chamber portion 114 is connectable to the lower chamber portion 115 via a sealing fastener or fastener plus sealing assembly 136 as described above and in FIG. 10A and the chamber is created in whole or in parts to allow for passing of console support members 109 and associated cabling as well as any handrails 104 from inside of the chamber 300 to outside of the chamber. The upper chamber portion 114 may be a single piece with multiple port assemblies 131, port assemblies that are movable, or may alternatively be fabricated from sections that are removable and connectable to allow for adaptation to a specific family or designs. In the case of FIG. 2, a portion of the chamber 300 designed to accommodate passing of the console support members 109 may include a replaceable section of the chamber in the vicinity of where the console support members are expected. This replacement section may be rigid plate with mating surface around the perimeter that is removably fastened to the chamber 300, or may be a flexible portion removed by a removable sealing fastener. Replacement sections may have different spacing, quantity orientation or other aspect of the port assemblies through which the console support members 109 are expected to pass in a substantially airtight manner. A user seal 302 may be fixed in height via a seal frame 124 as shown in FIG. 1 connected to various height adjustment posts 123, or may simply be fixed in height by webbing or strapping connected to the lower portion of the chamber. Sections of webbing connecting the lower chamber portion 114 or the chamber retaining members 113 and the rear of the seal frame 124 me be used in tandem with Alternate embodiment #6 such that the rear height adjustment posts 123 are eliminated. The strapping or webbing may be adjustable for example via a cam-lock buckle or tri-glide fastener to allow height adjustment of a rear portion of the user seal 302 while the front of the user seal is secured via the variations on Alternate embodiment #6. In so doing, the unweighting assembly 102 is further simplified and reduced in cost, bulk, and overall complexity and the adjustment of the rear of the seal frame during incline may be made even easier.

Where the term flexible and rigid, or equivalent synonyms are used in this specification, the reader shall note that the applicant may be referring to a property of the construction, and not necessarily that the materials themselves, as individuals or when combined, have flexible or rigid properties, i.e. form a material or combinations of materials that themselves be flexible or rigid in nature. The applicant acknowledges that the materials may have flexible or rigid properties themselves, but this may only be an option, not a requirement.

Similarly, the reader shall note that the applicant, when defining materials as non-stretch, or inelastic, or rigid understands that all materials stretch to some degree when a force is applied. The applicant's description of the term 'inelastic' or 'non-stretch' or 'rigid' within the context of this application shall therefore be construed to comply with the applicant's intent and purpose for each such element within each embodiment as described. For example, a 200 denier ballistic nylon fabric, coated with polyurethane may stretch less than 1% when subject to a stretching force, but such material may be considered inelastic, or otherwise known as 'non-stretch' in the industry, and considered non-stretch in the context of this invention when compared to prior art, which may stretch by a substantially greater amount, for example perhaps 100% for the same given applied force and material dimensions. The reader shall therefore refer to the intended use, desired traits, and function in the herein described invention when taking into context a material property being considered non-stretch vs. high spring rate vs. elastic.

Materials described similarly may be understood to encompass combinations of materials, varying material properties such as durometer or elastic modulus, lengths and widths, and profiles, which affect properties such as elasticity and coefficient of friction, may be considered within the scope of this invention. Further the reader shall note that where a material may be discussed as flexible, rigid, elastic, or non-elastic a material without that property may be combined with a material with that property to form what would be considered the original member (or visa-versa), but which is now two components and may not specifically match the description herein. However, in such cases, the reader shall note that the applicant has in fact considered that materials may be combined to perform the function of the elements of the inventions described herein, but has not made all such descriptions because of the endless possible combinations possible. All such combinations yield the same result as originally disclosed.

Height Adjustment Schemes

The reader shall note that while the height adjustment scheme of four posts and slots for insertion of a seal frame 124 has been primarily used for illustrative purposes, the broad concept of the applicant's invention may also incorporate other height adjustment schemes. Such schemes may include, but are not limited to, cantilevered sliding bars, strapping, collapsible bellows, hard and soft shell combinations, etc. Many such height adjustment schemes have been disclosed in the prior art and all such schemes shall be considered adaptable and suitable for use in the applicant's invention.

Shapes/Sizes

For example, in the case of chamber 300 shape, the inflatable portion of the chamber may be of any suitable geometry, size and shape to provide sufficient clearance for movement of the user 90 which also encompasses the exercise machine 101. Exercise machines 101 may come in multiple lengths and widths to accommodate a range of individuals, and not necessarily minimized in the number of variations, but rather targeted toward a specific size range or running speed of a user 90. It may be noted that chamber 300 size and shape may be reduced such that stresses are carried by the chamber walls and not by framing members in the case of a system designed for elderly users for example. All such configurations of profiles, shapes and sizes shall be considered within the scope of this application.

Combinations of Materials and Design Elements

The reader shall note that many design elements and material property combinations have been discussed and that these factors, such as handrails 104, additional framing height adjustment posts 123, seal frames 124, chambers 300, additional frame elements 111 to name a few, may all be combined in full or in part, altered in some way, shape, quantity or form, or otherwise modified so as to improve or alter the function and usability of the DAP unweighting system 100. For example, there may be as few as 1 height adjustment post 123 and this post may be cantilevered and placed at the rear or side of the chamber 300. Similarly, there may be 6 height adjustment posts 123, two on the sides, one in the front, and one in the rear, and still achieve the chamber 300 and user support and shaping around the user seal described in the applicant's invention.

Materials and components may be combined to reduce the number of parts and operations needed to fabricate unweighting assembly 102 and the applicant has discussed previously for components such as the intermediate connecting member 127 for example may be combined with a height adjustment post 123 and thereby eliminated. The reader shall understand that such combinations and advancements in material selections are known to those skilled in the art and shall be considered within the scope herein.

The applicant has covered in this application, the physics, mechanical properties, and tradeoffs of these various important properties and design elements, and the reader shall understand that all such combinations and modifications of these features that affect or improve the properties and function of DAP unweighting system 100 shall be considered within the scope of this invention, and the applicant's invention shall not be limited solely to the combinations depicted in the figures or described in this specification.

Materials

Various prior art and current designs have been described herein and in the referenced applications, and various material constructions and configurations have likewise been disclosed. Various components being flexible, rigid, elastic or non-elastic, and relative degrees of these properties been noted. The reader may note that for the sake of brevity, not all such combinations and material types have been discussed, but all such combinations, material properties or configurations may be considered within the scope of this invention. For example, in the case of the fastening means: cam-locks, ratchets, zippers, sealed zippers, and hook and loop fasteners have been described or referenced, however many other such means of fastening two objects together may be used such as a high friction joint tri-glide style mechanism, glues or adhesives, ropes or knots, mechanical hooks, buttons, racks and pinions, high friction surfaces, etc may be consider encompassed within the term fastening means and this term interpreted as broadly as possible. Further, in the case of elastic members or fabrics, polyurethane coated fabrics may be substituted for PVC coated fabrics or a similar material, and urethane molds, but may be of latex rubber, or similar material. In all such cases where specific materials are called out, the readers may understand that, this specification is but one example, and as long as the general concept described is achieved, the specific material, or specific property thereof, is not a requirement of the invention.

User

The user in the context of this application may be deemed to mean the person using the inventions described. This may be a client, patient, instructor, personal user, doctor, athletic trainer, coach, etc.

General

One skilled in the art will recognize any modifications that would be needed for such an intermingling and such modifications may be considered within the scope of this specification and claims. Further, it may be recognized that many of the components described may be combined into a single object via different manufacturing processes such as welding, injection molding, casting, etc. While the applicant discusses some of these options briefly in the application, it may be recognized any and all combinations of the components discussed herein may be considered within the scope of this application and covered by the claims written. Similarly, it may be recognized that many components in the system and their connection points, or connection means, may also be interchanged or rearranged to achieve the same effect as the disclosed configurations.

In general, blowers, valves, and valve types, fastening means, such as cam locks, hook and loop fasteners, ratchet mechanisms, spring elements, wiring intercept combinations, port assemblies, data cables etc. may be interchanged, used in quantities of more than one, altered in width, length, or profile and the inventions disclosed herein may be considered to have encompassed all such permutations and combinations of such components. Yet another example is the chamber 300 may have two input ports, one to allow air in and another to allow air out via a pressure relief valve. While such design is not shown in the figures above, the reader may note this concept is another example of how multiple items may be employed, and components shifted within the system to connect with different components, while the same overall system and effectiveness is maintained. Further still, the location and placement of various elements may be moved and altered such that they appear to differ from the figures shown, and description attached, however, all such configurations and combinations may be considered within the scope of the inventions disclosed herein. For example, in the case of the port of FIG. 5, the port assembly 131 may be on the lower chamber portion 115 instead of the upper chamber portion 114, and the function still maintained. In addition, the location of the port assembly 131 may be in the front of the chamber 300, or an additional port assembly may be added to the chamber for another handrail 104 as in the exercise machine of FIG. 2. As illustrated, there are many constructional permutations and combinations, and options for various material properties that yield satisfactory results in a DAP unweighting system, and all such combinations and permutations and material property choices may be considered within the scope of this invention.

The reader shall therefore understand that the applicant's invention allows for efficient construction, adaptation, and production of a DAP unweighting system 100 by taking advantage of existing exercise machine 101 design and minimally providing additional components around it. The reader shall also understand that the applicant has provided theory and designs through which one skilled in the art may simply and reasonably adapt or modify a construction to fit one or more different styles, models or types of exercise machines 101 in the industry and the inventions shall not be limited only to those described in this specification. The reader shall further note that the applicant's invention carries loads and forces, which may reach in the thousands of pounds, internally and with efficient transfer to the structural members 110 of the existing exercise machine 101 with only minimal optional reinforcement, thereby allowing re-use of maximum number of existing exercise machine frame elements 102 and reducing the overall bulk, cost and assembly difficulty of creating a DAP unweighting system either from scratch or via an add-on kit in the field.

Although the description above contains many specifications, these should not be construed as limiting the scope of the invention but as merely providing illustrations of some of the presently preferred embodiments of this invention. Thus the scope of this invention should be determined by the appended claims and their legal equivalents, rather than by the examples given.

We claim:

1. A system for unweighting a user wearing a user seal, the unweighting system comprising:
    an exercise machine frame element located about a running surface portion of an exercise machine; and
    a substantially airtight chamber extending upward when inflated from a base region thereof to an opposite top region thereof, the substantially airtight chamber comprising:
        a base attached to the exercise machine frame element;
        a top opening defined through the top region;
        an upper chamber portion operable for attachment with the user seal at the top opening;
        a lower chamber portion below the upper chamber portion; and
        a removable sealing assembly securing the lower chamber portion to the upper chamber portion.

2. The unweighting system of claim 1, wherein the removable sealing assembly secures the lower chamber portion directly to the upper chamber portion.

3. The unweighting system of claim 1, wherein the lower chamber portion comprises the base.

4. The unweighting system of claim 1, wherein the removable sealing assembly is proximate the base.

5. The unweighting system of claim 1, wherein the removable sealing assembly comprises:
    a first joint member attached to the lower chamber portion;
    a second joint member attached to the upper chamber portion; and
    at least one seal retaining member adapted for securing the first joint member with the second joint member in a substantially airtight arrangement;
    wherein a substantially airtight seal is formed between the first chamber portion and the second chamber portion during use of the exercise machine.

6. The unweighting system of claim 5, wherein the at least one retaining member comprises at least one of a retaining strut, a rectangular tube, and a removable sealing fastener.

7. The unweighting system of claim 5, wherein for the removable sealing assembly:
    the first joint member comprises one of a perimeter region of the lower chamber portion and a first fabric attached to a perimeter region of the lower chamber portion; and
    the second joint member comprises one of a perimeter region of the upper chamber portion and a second fabric attached to a perimeter region of the upper chamber portion.

8. The unweighting system of claim 7, wherein:
    the removable sealing assembly further comprises at least one flexible member extending along a length of the removable sealing assembly and arranged to contact at least one of the first joint member and the second joint member during use of the exercise machine; and
    the at least one flexible member is biased against at least one of the first joint member and the second joint member during use of the exercise machine such that the substantially airtight seal is formed between the first and second chamber portions.

9. The unweighting system of claim 7, wherein:
    the first joint member comprises a first fabric;
    the second joint member comprises a second fabric; and
    the at least one retaining member comprises a separable fastener configured for selectively separating the first fabric from the second fabric and connecting the first fabric to the second fabric such that the separable fastener allows the upper chamber portion attached to the second fabric to be selectively removed from the system and attached to the system.

10. The unweighting system of claim 9, wherein the separable fastener comprises:
    an inside pair of separating fasteners having a first inside fastener attached to the first fabric and a second inside fastener attached to the second fabric, the first and second inside fasteners configured for fastening to each other; and
    an outside pair of separating fasteners having a first outside fastener attached to the first fabric and a second outside fastener attached to the second fabric, the first and second outside fasteners configured for fastening to each other.

11. The unweighting system of claim 10, wherein:
    the fastened inside pair of separating fasteners and the fastened outside pair of separating fasteners define a pocket retaining a flexible member;
    the first fabric and second fabric are configured to apply tensile forces in opposite directions away from the separable fastener;
    the pocket is configured to compress the flexible member between the inside pair of separating fasteners and the outside pair of separating fasteners; and
    the separable fastener and the flexible member form a bi-directional seal during use of the system;
    wherein the flexible member is configured to have a first shape prior to inflation and deform to a second shape upon inflation, the second shape forming an improved seal in response to inflation forces.

12. The unweighting system of claim 10, wherein:
    a mating end of one of the first and second inside fasteners includes a male zipper half;
    a mating end of the other one of the first and second inside fasteners includes a female zipper half;
    a mating end of one of the first and second outside fasteners includes a male zipper half; and
    a mating end of the other one of the first and second outside fasteners includes a female zipper half;
    wherein the mating ends of the first and second inside fasteners are configured to form an inside zipper fastener, and the mating ends of the first and second outside fasteners are configured to form an outside zipper fastener, the inside zipper fastener and the outside zipper fastener forming a bi-directional seal with the flexible member.

13. An exercise system for unweighting a user for an exercise session of the exercise system, the unweighting exercise system comprising:
    a treadmill exercise device comprising a treadmill frame and a rotatable belt adapted for user engagement for the exercise session, the rotatable belt having a belt width;
    an unweighting assembly adapted for applying upward, unweighting force to the user for the exercise session;
    a system frame retaining the treadmill exercise device and securing the unweighting assembly in an exercise arrangement with the treadmill exercise device while the unweighting assembly is in a pressurized state for the exercise session, the system frame comprising:
the treadmill frame;
a plurality of frame elements structurally attached to the treadmill frame; and
a top surface region adapted for user engagement during the exercise session, the top surface region having a surface width and a surface length, the top surface region comprising:
a movable running surface defined by the rotatable belt, the movable running surface extending a run length; and
a stationary deck extending about at least a portion of the movable running surface, the stationary deck defining a sealing surface having a maximum seal width greater than the belt width and less than the surface width; and
a substantially airtight chamber attached to the top surface region in a substantially sealed connection to the sealing surface.

14. The unweighting exercise system of claim 13 wherein the sealing surface extends over and across a portion of the movable belt.

15. The unweighting exercise system of claim 14 wherein the portion of the movable belt is one of a forward region of the movable belt and a rearward region of the movable belt.

16. The unweighting exercise system of claim 14 wherein:
the portion of the movable belt is a first portion of the movable belt; and
the sealing surface extends over and across the first portion of the movable belt and over and across a second portion of the movable belt.

17. The unweighting exercise system of claim 16 wherein:
the first portion is at a forward region of the system frame; and
the second portion is at an opposite rearward region of the system frame.

18. The unweighting exercise system of claim 13 wherein the sealing surface has a seal length less than the run length of the movable belt.

19. The unweighting exercise system of claim 13 wherein the system frame further comprises:
a seal frame adapted for limiting a vertical height of the substantially airtight chamber when inflated;
a first height adjustment post at a first side region of the treadmill exercise device; and
a second height adjustment post at an opposite second side region of the treadmill exercise device;
wherein the first height adjustment post and the second height adjustment post are adapted to support the seal frame at a vertical height limit during use of the unweighing exercise system.

20. The unweighting exercise system of claim 19 wherein the sealing surface is disposed between the pair of height adjustment posts.

* * * * *